US007998477B2

(12) United States Patent
Yakovlevsky et al.

(10) Patent No.: US 7,998,477 B2
(45) Date of Patent: Aug. 16, 2011

(54) SPHERICAL PROTEIN PARTICLES AND METHODS FOR MAKING AND USING THEM

(75) Inventors: Kirill Yakovlevsky, Cambridge, MA (US); Michael Shamashkin, Somerville, MA (US); Nazer Khalaf, Worcester, MA (US); Chandrika P. Govardhan, Lexington, MA (US); Chu W. Jung, Arlington, MA (US)

(73) Assignee: Althea Technologies Inc., San Diego, CA (US)

( * ) Notice: Subject to any disclaimer, the term of this patent is extended or adjusted under 35 U.S.C. 154(b) by 1 day.

(21) Appl. No.: 10/741,861

(22) Filed: Dec. 19, 2003

(65) Prior Publication Data

US 2004/0219224 A1 Nov. 4, 2004

Related U.S. Application Data

(63) Continuation of application No. PCT/US02/19870, filed on Jun. 21, 2002.

(60) Provisional application No. 60/299,989, filed on Jun. 21, 2001.

(51) Int. Cl.
*A61K 39/395* (2006.01)

(52) U.S. Cl. .............. 424/130.1; 530/387.1; 530/418; 977/904

(58) Field of Classification Search .............. 424/489, 424/490, 491, 130.1; 530/387.1, 418, 350, 530/324; 514/2; 977/904
See application file for complete search history.

(56) References Cited

U.S. PATENT DOCUMENTS

| 4,334,024 | A | | 6/1982 | Johal |
| 4,959,351 | A | | 9/1990 | Grau |
| 5,510,118 | A | | 4/1996 | Bosch et al. |
| 5,751,453 | A | * | 5/1998 | Baur .................. 349/12 |
| 5,780,599 | A | | 7/1998 | Junker et al. |
| 5,849,296 | A | | 12/1998 | Navia et al. |
| 5,904,935 | A | | 5/1999 | Eckenhoff et al. |
| 5,972,331 | A | | 10/1999 | Reichert et al. |
| 6,011,001 | A | | 1/2000 | Navia et al. |
| 6,042,824 | A | | 3/2000 | Khalaf |
| 6,063,910 | A | | 5/2000 | Debenedetti et al. |
| 6,140,475 | A | | 10/2000 | Margolin et al. |
| 6,143,211 | A | | 11/2000 | Mathiowitz et al. |
| 6,310,038 | B1 | | 10/2001 | Havelund |
| 6,458,387 | B1 | * | 10/2002 | Scott et al. .............. 424/489 |
| 6,555,110 | B1 | * | 4/2003 | D'Souza .............. 424/130.1 |
| 6,562,952 | B1 | * | 5/2003 | Rajewski et al. .......... 530/418 |
| 6,630,121 | B1 | * | 10/2003 | Sievers et al. .............. 424/1.13 |
| 6,652,837 | B1 | * | 11/2003 | Edwards et al. .............. 424/45 |
| 6,727,278 | B1 | * | 4/2004 | Averback .............. 514/456 |
| 6,756,062 | B2 | * | 6/2004 | Johnston et al. .............. 424/489 |
| 6,794,357 | B1 | * | 9/2004 | Edman et al. .............. 514/2 |
| 6,821,429 | B2 | * | 11/2004 | Perrut .............. 210/634 |
| 6,835,396 | B2 | * | 12/2004 | Brynjelsen et al. .............. 424/450 |
| 6,860,907 | B1 | * | 3/2005 | Hanna et al. .............. 23/300 |
| 6,942,868 | B2 | * | 9/2005 | Edwards et al. .............. 424/400 |
| 6,956,021 | B1 | * | 10/2005 | Edwards et al. .............. 514/2 |
| 2002/0136719 | A1 | * | 9/2002 | Shenoy et al. .............. 424/130.1 |
| 2004/0219224 | A1 | | 11/2004 | Yakovlevsky et al. |

FOREIGN PATENT DOCUMENTS

| EP | 0166 233 A2 | 1/1986 |
| WO | WO 9109943 | 7/1991 |
| WO | WO 9640049 | 12/1996 |
| WO | WO 9708300 | 3/1997 |
| WO | WO 9744445 | 11/1997 |
| WO | WO 9846732 | 10/1998 |
| WO | WO 9955310 | 11/1999 |
| WO | WO 0052150 | 8/2000 |
| WO | WO 0077281 | 12/2000 |

OTHER PUBLICATIONS

Rembaum, Alan (Chemtech 8(3), 182-90, 1978).*
Truong, Vu L. (Drug Delivery 2(3/4), 166-74, 1995).*
Rembaum, A. (Science 208(4442), 364-8, 1980).*
Rembaum, Alan (Pure and Applied Chemistry 52(5), 1275-78, 1980).*
Holubar, K. (International Archives of Allergy and Applied Immunology 44(4), 489-499, 1973).*
Harris L. J. (Proteins 23(2), 285-289, 1995).*
Gross M., (Nature 373(6510), 105-106, 1995).*
Kovari L. C. (Structure [London, England : 1993] 3(12), 1291-1293, 1995).*
Edmundson A. B. (Immunotechnology : an international journal of immunological engineering 3(4), 309-317, 1998).*
Patenaude S. I. (Acta crystallographica. Section D, Biological crystallography, D54, 1456-59, 1998).*
English Abstract of Matsuura, Crystallization of Proteins, vol. 12, No. 1-2, 108, 1985.*
Abstract of Blanco, Eur J Pharm Biopharm 45(3) 285-94, 1998.*
Abstract of Kuttner, Mol Immunol 35(3) 189-94, 1998.*

(Continued)

*Primary Examiner* — David Lukton
(74) *Attorney, Agent, or Firm* — Wilson Sonsini Goodrich & Rosati

(57) ABSTRACT

This invention relates to SPPs, spherical nanocrystalline composite particles or crystalline SPPs of biologically active proteins or compositions, including formulations, comprising such SPPs, spherical nanocrystalline composite particles or crystalline SPPs.

More particularly, methods are provided for the production of SPPs, spherical nanocrystalline composite particles or crystalline SPPs of high concentrations of biologically active proteins, and for the preparation of stabilized SPPs, spherical nanocrystalline composite particles or crystalline SPPs for use alone, or in dry or slurry compositions. This invention also relates to methods for stabilization, storage and delivery of biologically active proteins using SPPs, spherical nanocrystalline composite particles or crystalline SPPs.

The present invention further relates to methods using SPPs, spherical nanocrystalline composite particles or crystalline SPPs, or compositions or formulations comprising such SPPs, spherical nanocrystalline composite particles or crystalline SPPs, for biomedical applications, including biological delivery to humans and animals.

25 Claims, 16 Drawing Sheets

OTHER PUBLICATIONS

Babay, D., et al., "Design and release kinetic pattern evaluation of indomethacin microspheres intended for oral administration," *Biomaterials* 9:482-488 (1988).

Baselga, J., et al., "Recombinant humanized anti-HER2 antibody (Herceptin) enhances the antitumor activity of paclitaxel and doxorubicin against HER2/neu overexpressing human breast cancer xenografts," *Cancer Res.* 58:2825-2831 (1998); Erratum in: *Cancer Res.* 59:2020 (1999).

Bustami, R.T., et al., "Generation of micro-particles of proteins for aerosol delivery using high pressure modified carbon dioxide," *Pharm. Res.* 17:1360-1366 (2000).

Dong, A., et al., "Infrared spectroscopic studies of lyophilization- and temperature-induced protein aggregation," *J Pharm Sci.* 84:415-424 (1995).

Dong, A., et al., "Secondary structure of the pentraxin female protein in water determined by infrared spectroscopy: effects of calcium and phosphorylcholine," Biochemistry 31:9364-9370 (1992).

Giegé, R., et al., "An introduction to the crystallogeneis of biological macromolecules", *Crystallization of Nucleic Acids and Proteins, a Practical Approach* Oxford University Press, $2^{nd}$ ed., 1-16 (1999).

Gilding, D.K., et al., "Biodegrabale polymers for use in surgery-polyglycolic/poly(actic acid) homo- and copolymers:1," *Polymer* 20:1459-1464 (1981).

Gombotz W.R., et al., "Biodegradable polymers for protein and peptide drug delivery," *Bioconjug. Chem.* 6:332-351 (1995).

Heller, J., et al., "Theory and Practice of Controlled Drug Delivery from Biodegradable Polymers," *Controlled Release of Bioactive Materials Academic Press*, 1-17 (1980).

Lehmann, K.O.R., et al., "Controlled Drug Release from Small Particles Encapsulated with Acrylic Resins," *Polymeric Delivery Systems.* 111-119 (1979).

Morita, T., et al., "Formation and Isolation of spherical fine protein microparticles through lyophilization of protein-poly(ethylene glycol) aqueous mixture," *Pharm. Res.* 17:1367-1373 (2000).

Pekarek, K.J., et al., "Double-walled polymer microspheres for controlled drug release," *Nature* 367:258-260 (1994).

Pietras, R.J., et al., "Monoclonal antibody to HER-2/neureceptor modulates repair of radiation-induced DNA damage and enhances radiosensitivity of human breast cancer cells overexpressing this oncogene," *Cancer Res.* 59:1347-1355 (1999).

Ramadan, E.M., et al., "Effect of encapsulation of mefenamic acid with cationic Eudragit E on its bioavailability and gastric ulcerogenic activity in rabbits," *Journal of Microencapsulation* 4:125-132 (1987).

Ruth, L., et al., "alpha-L-iduronidase forms semi-crystalline spherulites with amyloid-like properties," *Acta. Crystallogr. D. Biol. Crystallogr.* 56:524-528 (2000).

Kuznetsov, Yu G et al., "Chimeric Human-Simian Anti-CD4 Antibodies Form Crystalline High Symmetry Particles" Journal of Structural Biology vol. 131, pp. 108-115 (2000).

Thompson et al. "Purification of Eukaryotic RNA Polymerase II by Immunoaffinity Chromatography", vol. 265, No. 12, pp. 7069-7077, Apr. 1990.

Adams, et al., (1999) "Generating improved single-chain Fv molecules for tumor targeting," Journal of Immunological Methods, v. 231, pp. 249-260.

Bertolini, et al., (2000) "Endostatin, an antiangiogenic drug, induces tumor stabilization after chemotherapy or anti-CD20 therapy in a NOD/SCID mouse model of human high-grade non-Hodgkin lymphoma," Neoplasia, v. 96, pp. 282-287.

Blanco, et al., (1998) "Protein encapsulation and release from poly(lactide-co-glycolide) microspheres: effect of the protein and polymer properties and of the co-encapsulation of surfactants," Eur. J. Pharm. Biopharm. v. 45, pp. 285-294.

Boehm, et al., (2000) "Crystal structure of the anti-(cacinoembryonic antigen) single-chain Fv antibody MFE-23 and a model for antigen binding based on intermolecular contacts," The Biochemical Journal, v. 346, pp. 519-528.

Braden, et al., (2000) "X-ray crystal structure of an anti-Buckminsterfullerene antibody Fab fragment: Biomolecular recognition of C.sub.60," Proc. Natl. Acad. Sci. USA, v. 97, pp. 12193-12197.

Brange, et al., (1992) "Chemical Stability of Insulin. 1. Hydrolytic Degradation During Storage of Pharmaceutical Preparations,") Pharm. Res., v. 9, pp. 715-726.

Chayen (2004), "Turning protein crystallisation from an art into a science", Current Opinion in Structural Biology, v. 14, pp. 577-583.

Chayen, et al., (1999) "Recent Advances in Methodology for Crystallization of Biological Macromolecules, " Journal of Crystal Growth, v. 198-199, pp. 649-655.

Cheetham, et al. (1998) "Crystal Structures of a Rat Anti-CD52 (CAMPATH-1) Therapeutic Antibody Fab Fragment and its Humanized Counterpart". Journal of Molecular Biology., v. 284, pp. 85-99.

Covaceuszach, et al., (2001) "Purification, crystallization and preliminary X-ray analysis of the Fab fragment from MNAC13, a novel antagonistic anti-tyrosine kinase A receptor monoclonal antibody" Acta. Crystallogr. D. Biol. Crystallogr., v. 57, pp. 1307-1309.

Creighton, T. E. (1993) Proteins: Structures and Molecular Properties, 2nd Ed., W. H. Freeman and Company, pp. 202-203 Only.

Cudney, (1999) "Protein Crystallization and Dumb Luck," Rigaku Journal, v. 16(1), pp. 1-7.

Ely, et al., (1978) "Mobile Fc Region in the Zie IgG2 Cryoglobulin: Comparison of Crystals of the F(ab')2 Fragment and the Intact Immunoglobulin. Biochemistry., v. 17(5), pp. 820-823.

Essig, et al., (1993) "Crystallization of single-chain Fv proteins," Journal of Molecular Biology, 234(3), pp. 897-901.

European Application EP07003574.6 (ALTH-006/02EP) Office Action mailed Nov. 10, 2010.

Hainsworth, et al., (2000) "Monoclonal antibody therapy in lymphoid malignancies," The Oncologist, v. 5(5), pp. 376-384.

Hampton Crystal Screen, 2000-2002, pp. 1-4, Hampton Research, 27632 El Lazo Road, Suite 100, Laguna Nigel, California, 92677-3913.

Harris, et al., "Comparison of the conformations of two intact monoclonal antibodies with hinges," Immunol. Rev., vol. 163, pp. 35-43 (1998).

Harris, et al., (1998) "Crystallographic Structure of an Intact IgG1 Monoclonal Antibody," J. Mol. Biol., v. 275, pp. 861-872.

Hoedemaeker, et al., (1997) "A single chain Fv fragment of P-glycoprotein-specific monoclonal antibody C219: design, expression, and crystal structure at 2.4 resolution," J. Biol. Chem., v. 272, pp. 29784-29789.

Ito, et al., (2001) "Crystallization and preliminary X-ray crystallographic studies on a Fab fragment of the mouse anti-human Fas monoclonal antibody HFE7A," Acta. Crystallogr. D. Biol. Crystallogr., v. D57, pp. 1700-1702.

Japan Application 2002-571549 (ALTH-006/01JP) Office Action dated Nov. 12, 2009.

Jen et al. (Nov. 2001) "Diamonds in the Rough: Protein Crystals from a Formulation Perspective," Pharmaceutical Research, v. 18(11), pp. 1483-1488.

Kim et al., (2000) "Gene therapy for established murine collagen-induced arthritis by local and systemic adenovirus-mediated delivery of interleukin-4," Arthritis Res., v. 2, pp. 293-302.

Klyushnicenko, V. (2003) "Protein crystallization: From HTS to kilogram-scale," Current Opinion in Drug Discovery and Development., v. 6,(6), pp. 848-854.

Kundrot, et al. (2004)"Which Strategy for a Protein Crystallization Project," Cellular and Molecular Life Sciences, v. 61, pp. 525-536.

Malfait, et al., (2001) "Chronic Relapsing Homologous Collagen-Induced Arthritis in DBA/1 Mice as a Model for Testing Disease-Modifying and Remission-Inducing Therapies," Arthritis Rheum., v. 44, pp. 1215-1224.

Matthey, et al., (2000) "Recombinant immunotoxins for the treatment of Hodgkin's Disease (review)," International Journal of Molecular Medicine, 6(5), pp. 509-514.

McPherson et al. (1990) "Current Approaches to Macromolecular Crystallization," Eur. J. Biochem. v. 189, pp. 1-23.

McPherson, (1989) "Preliminary Analysis: Mounting and aligning procedures in Preparation and Analysis of Protein Crystals," John Wiley & Sons Publishing, pp. 214-227.

McPherson, et al., (1985) "Crystallization of Macromolecules: General Principles," Methods in Enzymology v. 114, pp. 112-120.

Messner, et al., (1993) "Reversible cross-linking of crystalline bacterial surface layer glycoproteins through their glycan chains." Applied Microbiology and Biotechnology, v. 40, pp. 7-11.

Morita, et al., (2000) "Formation and isolation of spherical fine protein microparticles through lyophilization of protein-poly(ethylene glycol) aqueous mixture," Pharm. Res., v. 17, pp. 1367-1373.

Pichla, et al. (1997) "The Crystal Structure of a Fab Fragment to the Melanoma-Associated GD2 Ganglioside," J. Struct. Biol., v. 119, pp. 6-16.

Pikal, et al., (1978) "Quantitative Crystallinity Determinations for beta.-Lactam Antibiotics by Solution Calorimetry: Correlations with Stability," J. Pharm. Sci., v. 67, pp. 767-773.

Pikal, et al., (1997) "The Stability of Insulin in Crystalline and Amorphous Solids: Observation of Greater Stability for the Amorphous Form," Pharm. Res., v. 14, pp. 1379-1387.

Pollock, et al., (1999), "Transgenic milk as a method for the production of recumbinant antibodies," J. Immunol. Methods, v. 231(1-2), pp. 147-157.

Remicade Package Insert, Aug. 1998.

Rodgers, (1997) "Practical Cryocrystallography," Methods in Enzymology, v. 276, pp. 183-203.

Saphire, et al., (2001) "Crystallization and Preliminary Structure Determination of an Intact Human Immunoglobulin, b12: An Antibody that Broadly Neutralizes Primary Isolates of HIV-1," Acta Cryst., v. D57, pp. 168-171.

Saul, et al., (2000) "Structure of the Fab fragment from F124, a monoclonal antibody specific for hepatitis B surface antigen," Acta. Crystallogr. D. Biol. Crystallogr., v. D56, pp. 945-951.

Schwarz, et al., (2000) "Anti-TNF-Alpha Therapy as Clinical Intervention for Periprosthetic Osteolysis," Arthritis Research, v. 2, pp. 165-168.

Shenoy, et al., (2001) "Stability of crystalline proteins," Biotechnology and Bioengineering, v. 73, pp. 358-369.

Sohi, et al., (1994) "Crystallization and Preliminary X-ray Analysis of the Fab Fragment of a Human Monoclonal IgM Rheumatoid Factor (2A2)," J. Mol. Biol., v. 242, pp. 706-708.

Sullivan, et al., (1998) "Sustained release of progesterone and estradiol from the SABER.TM. delivery system: in vitro and in vivo release rates," Proceed. Intl. Symp. Control. Rel. Bioact. Mater., v. 25, pp. 653-654.

Van Assche et al., (2000) "Anti-TNF agents in Crohn's Disease," Expert Opinion in Investigational Drugs, v. 9(1), pp. 103-111.

Weber (1997). "Overview of Crystallization Methods," Methods in Enzymology, v. 276, pp. 13-22.

Yang et al., (Jun., 2003) Crystalline monoclonal antibodies for subcutaneous delivery, PNAS, v. 100, pp. 6934-6939.

Yoshino, (1998) "Treatment with an Anti-IL-4 Monoclonal Antibody Blocks Suppression of Collagen-Induced Arthritis in Mice by Oral Administration of Type II Collagen," J. Immunol., v. 160, pp. 3067-3071.

* cited by examiner

FIGURE 1: MORPHOLOGY OF MONOCLONAL ANTIBODY SPPs
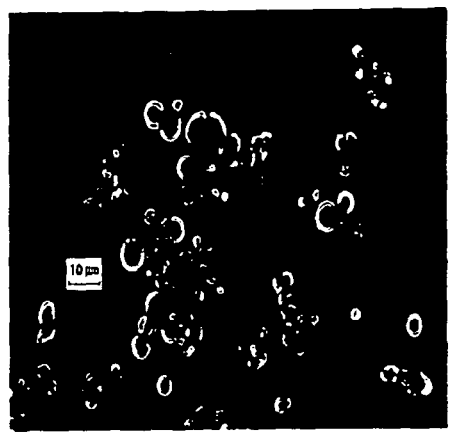
A. Infliximab (Remicade™) SPPs
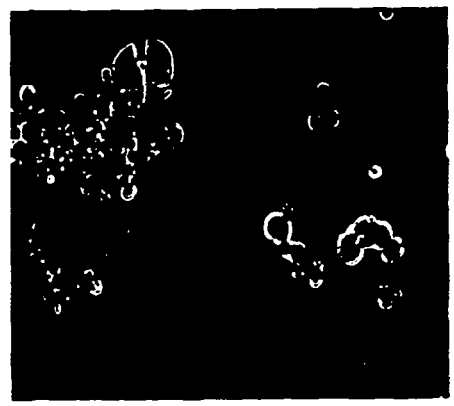
B. Rituximab (Rituxan™) SPPs
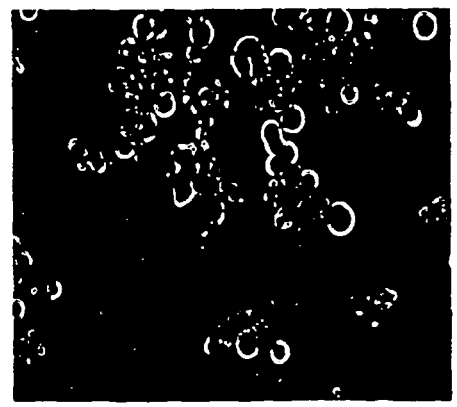
C. Trastuzumab (Herceptin™) SPPs

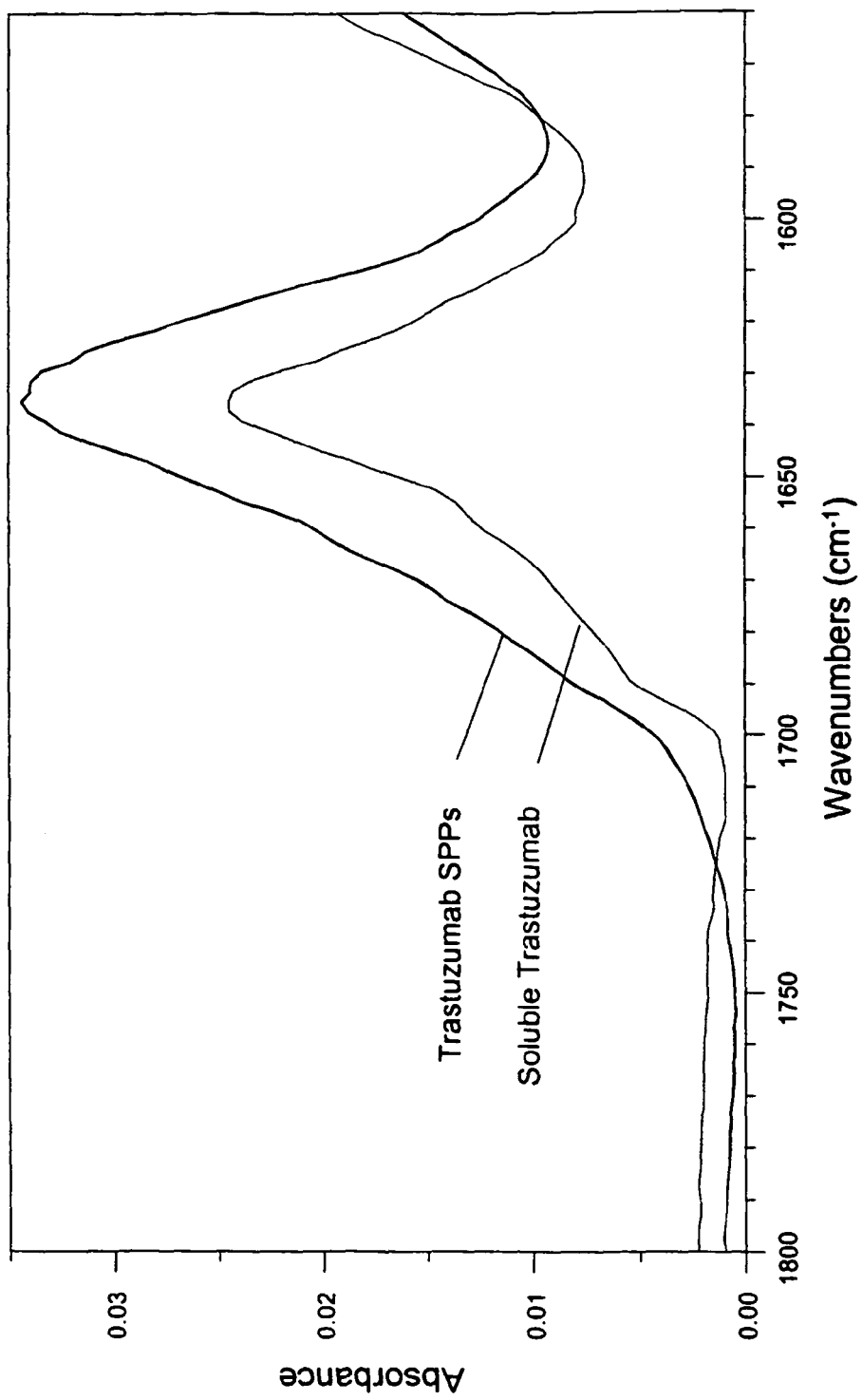
FIGURE 2: FTIR ANALYSIS OF TRASTUZUMAB SPPs AND NATIVE, SOLUBLE TRASTUZUMAB

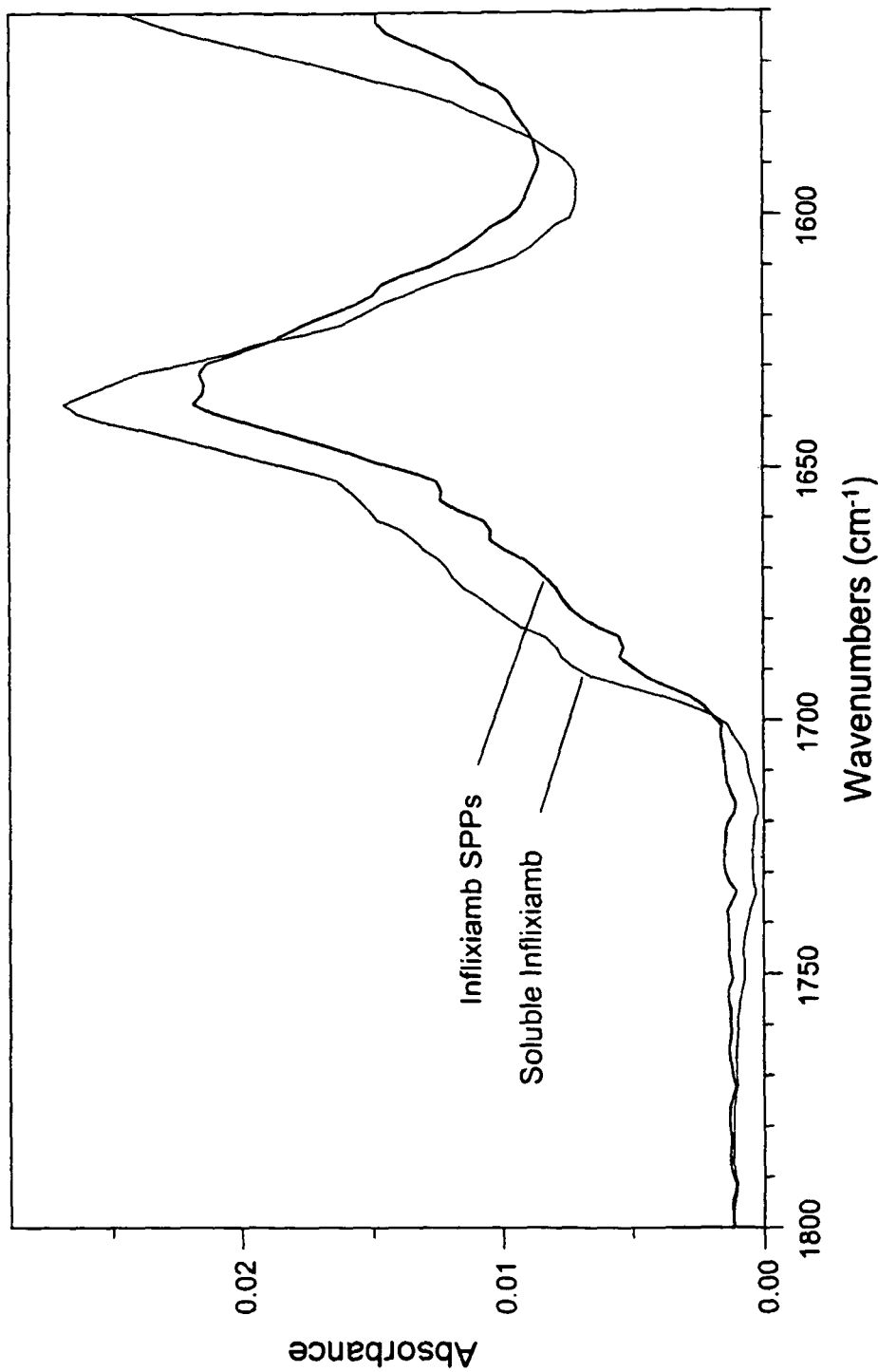
FIGURE 3: FTIR ANALYSIS OF INFLIXIMAB SPPs AND NATIVE, SOLUBLE INFLIXIMAB

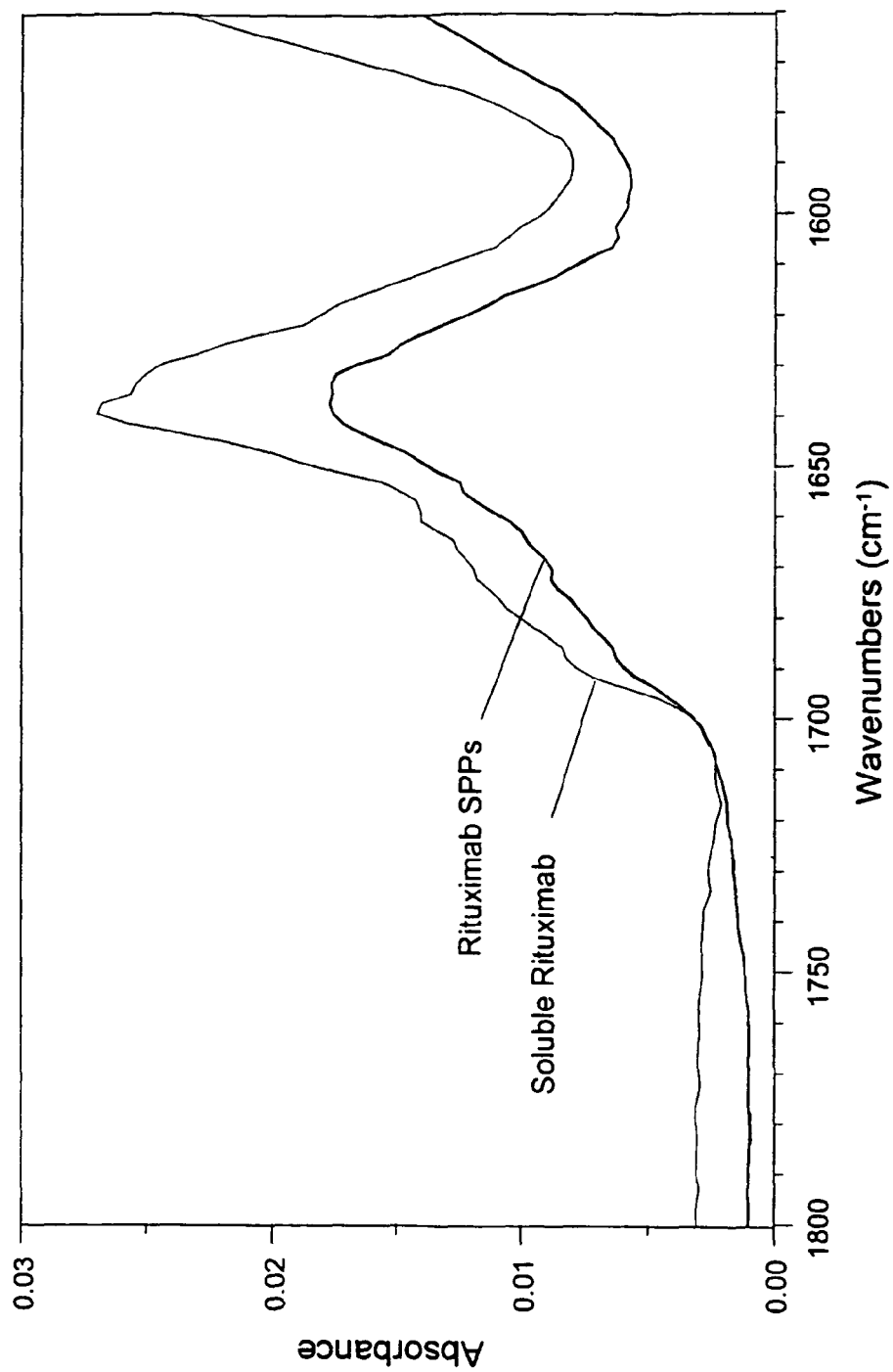
FIGURE 4: FTIR ANALYSIS OF RITUXIMAB SPPs AND NATIVE, SOLUBLE RITUXIMAB

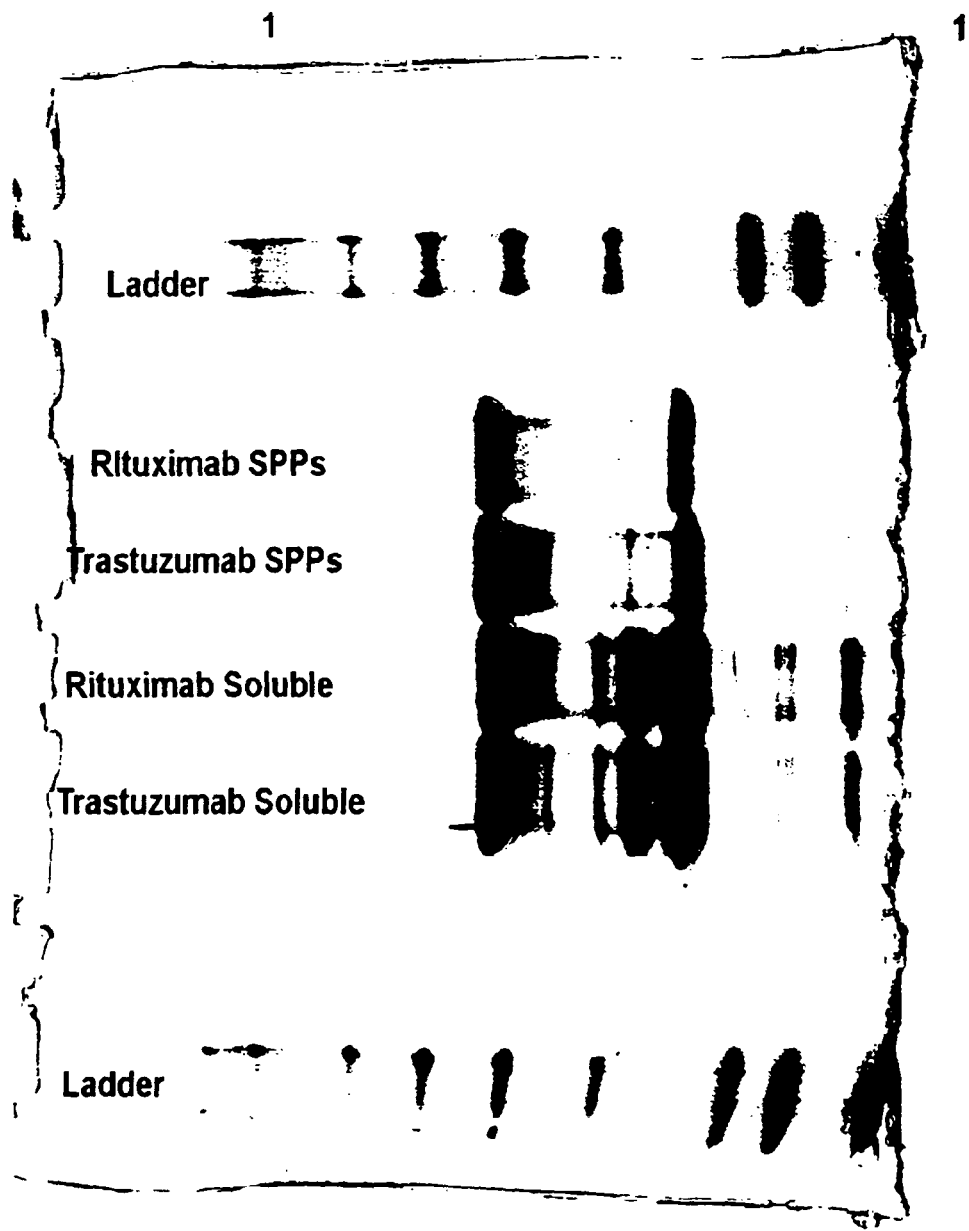
FIGURE 7: Comparison of the Stability of Dissolved Rituximab and Trastuzumab SPPs with the Stability of Native, Soluble Rituximab and Trastuzumab

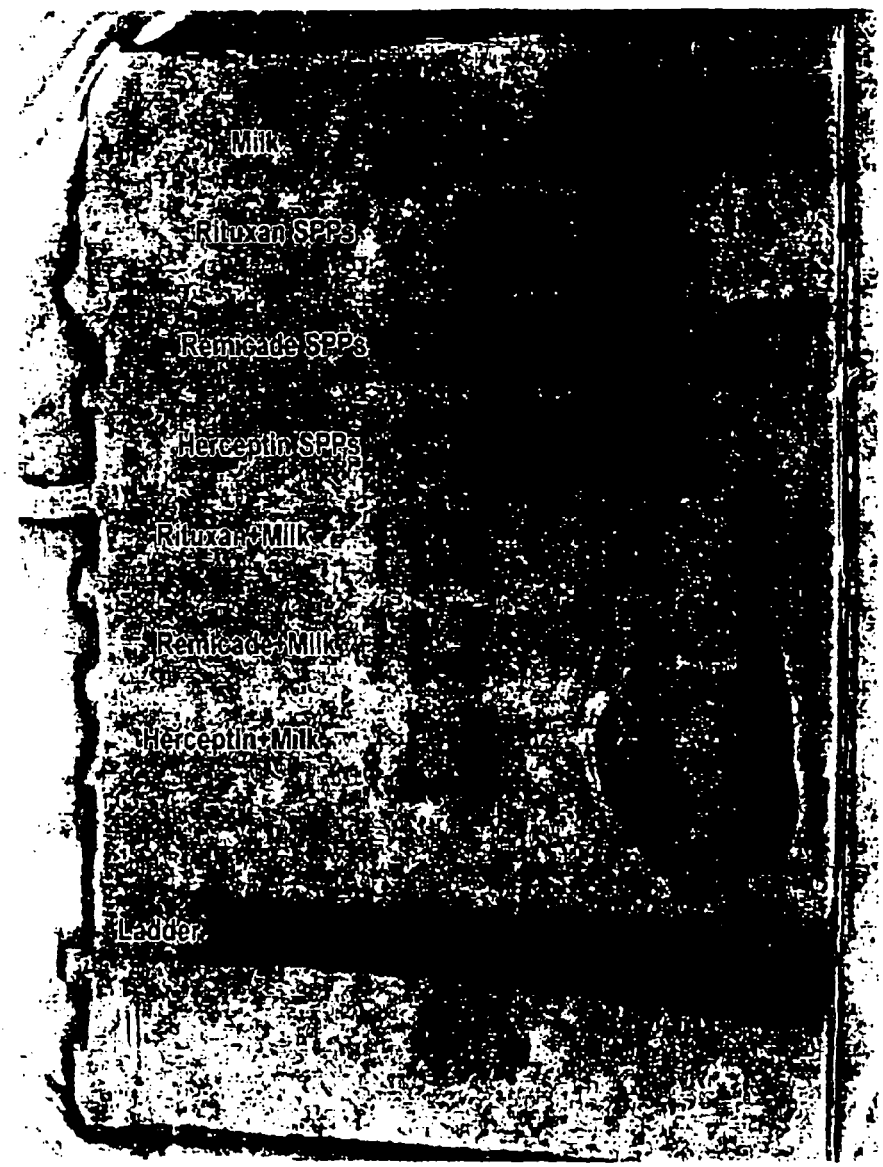
Figure 8: Selective fractionation/purification of Infliximab (Remicade™), Rituximab (Rituxan™) and Trastuzumab (Herceptin™) from milk proteins by preparation of SPPs

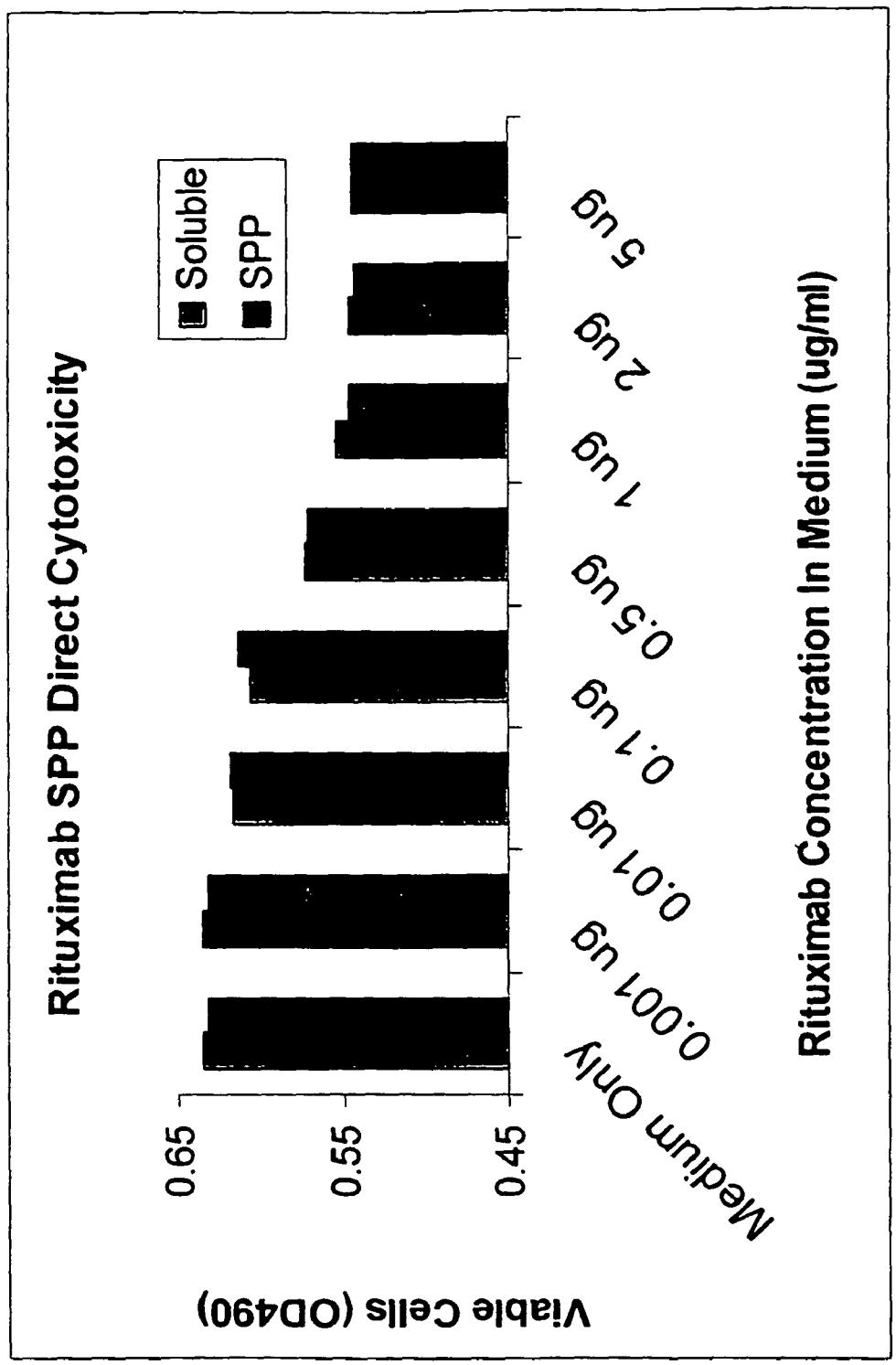
Figure 9: Rituximab SPP-Induced Direct Cytotoxicity

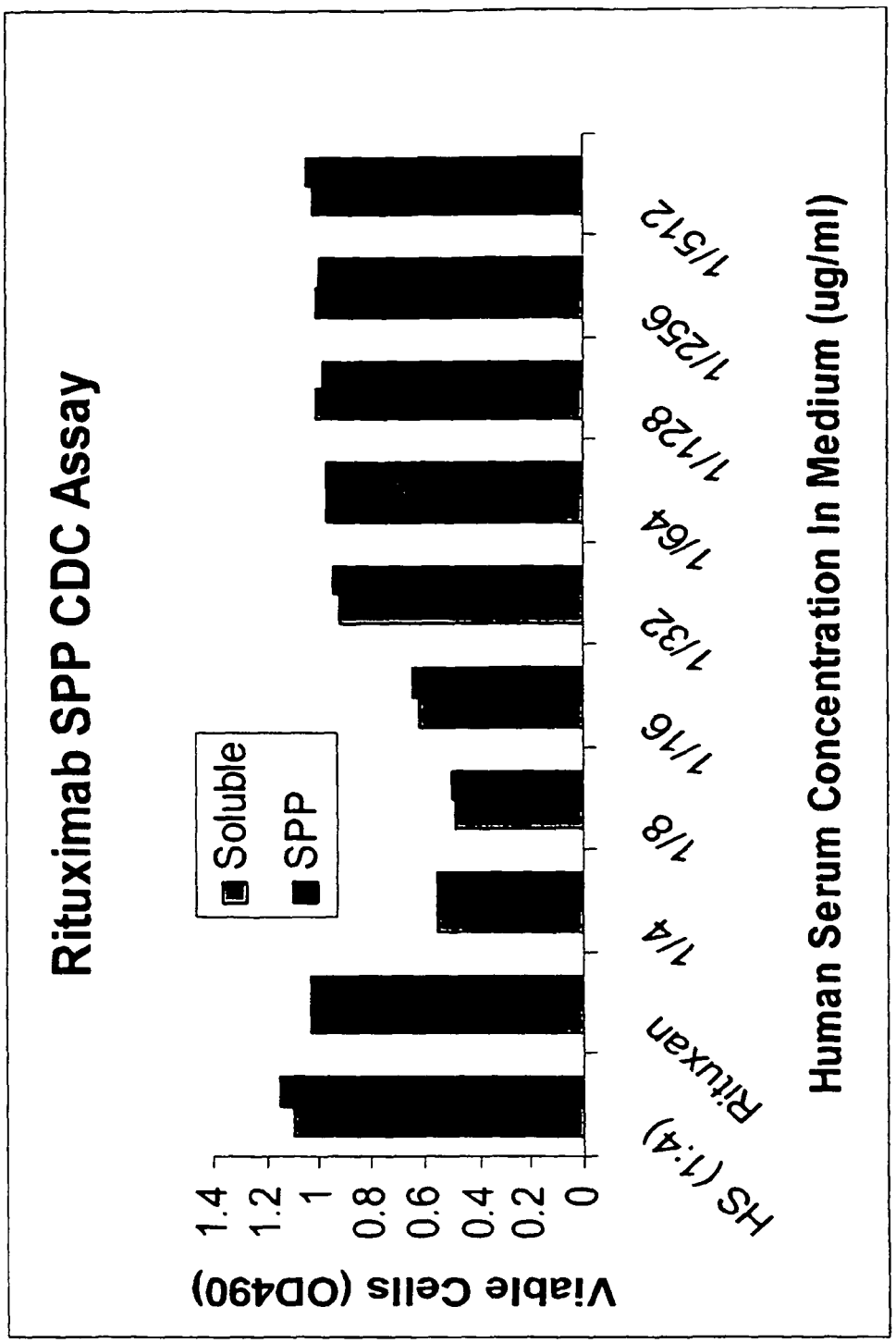
Figure 10: Rituximab SPP-Induced Complement Dependent Cytotoxicity

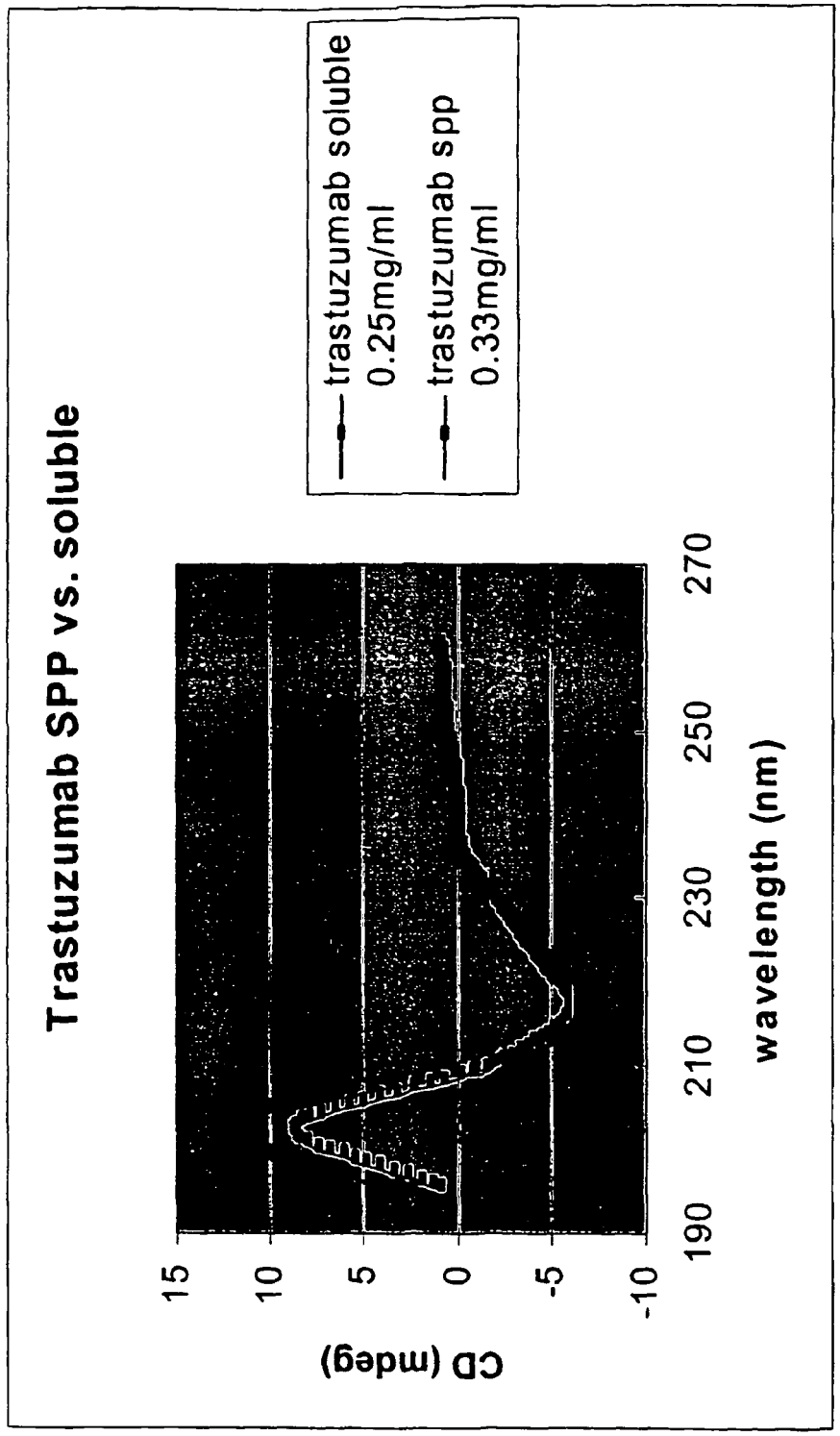
Figure 11: Circular Dichroism (CD) Spectra of Trastuzumab SPPs Compared to Native, Soluble Trastuzumab

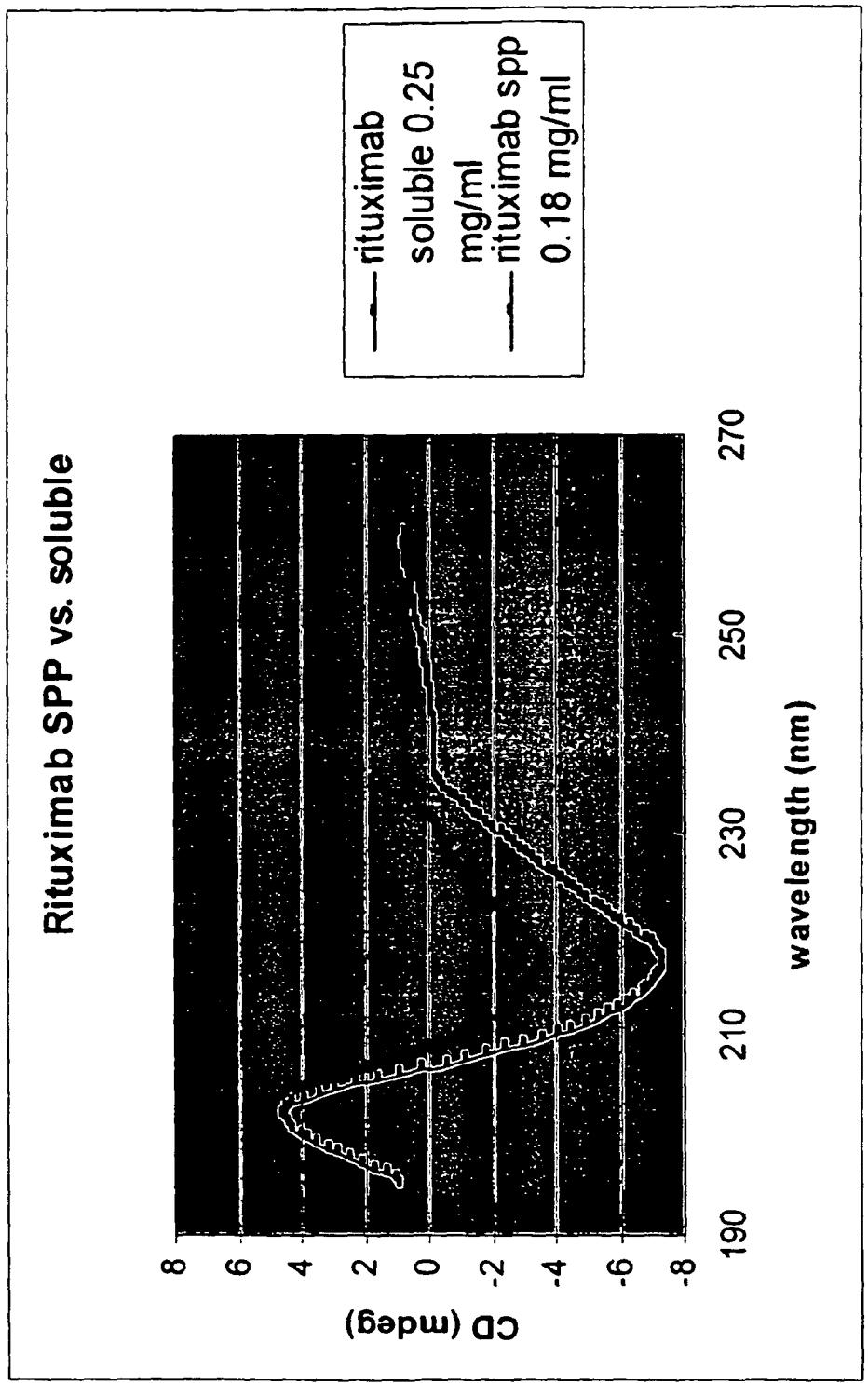
Figure 12: Circular Dichroism (CD) Spectra of Rituximab SPPs Compared to Native, Soluble Rituximab

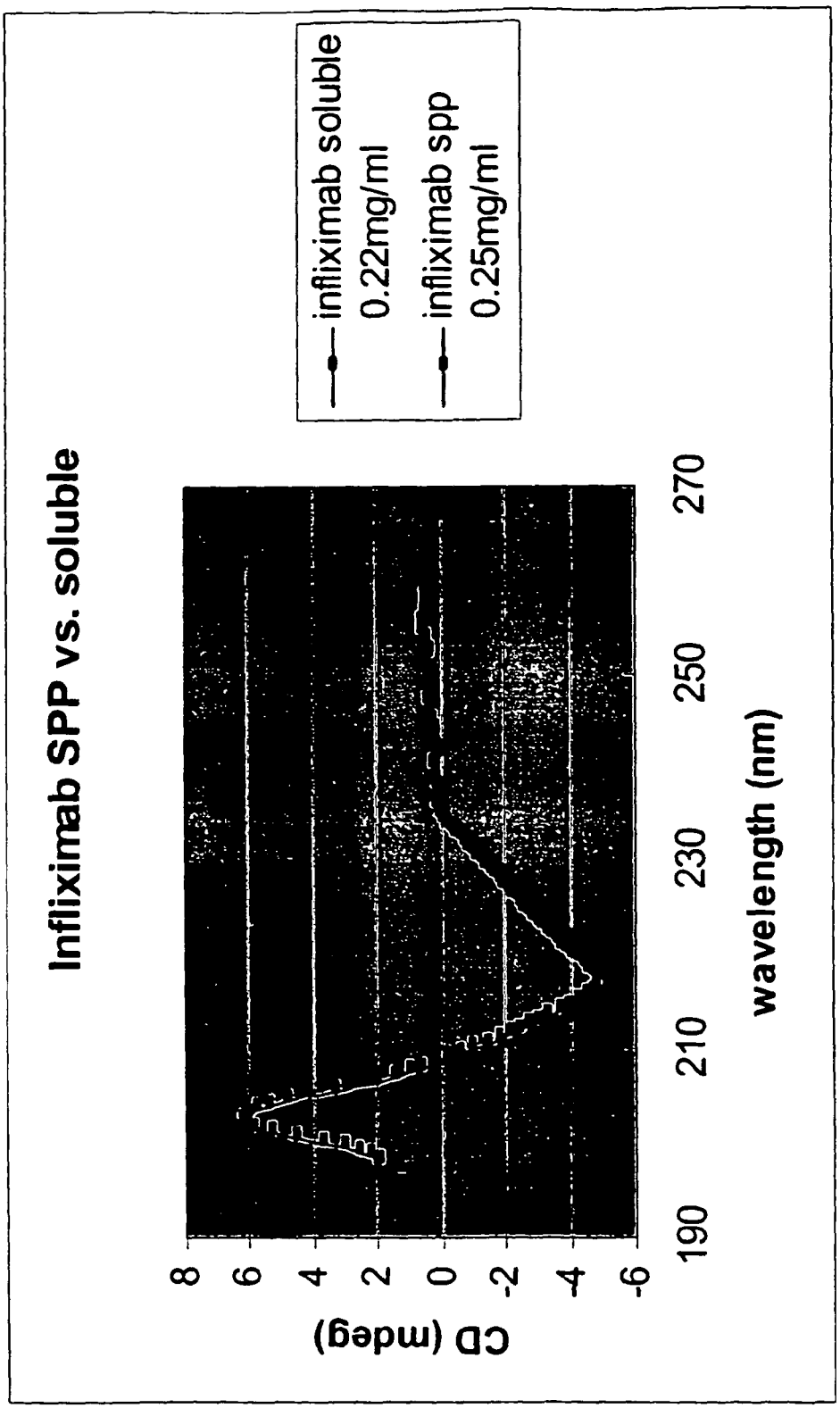
Figure 13: Circular Dichroism (CD) Spectra of Infliximab SPPs Compared to Native, Soluble Infliximab

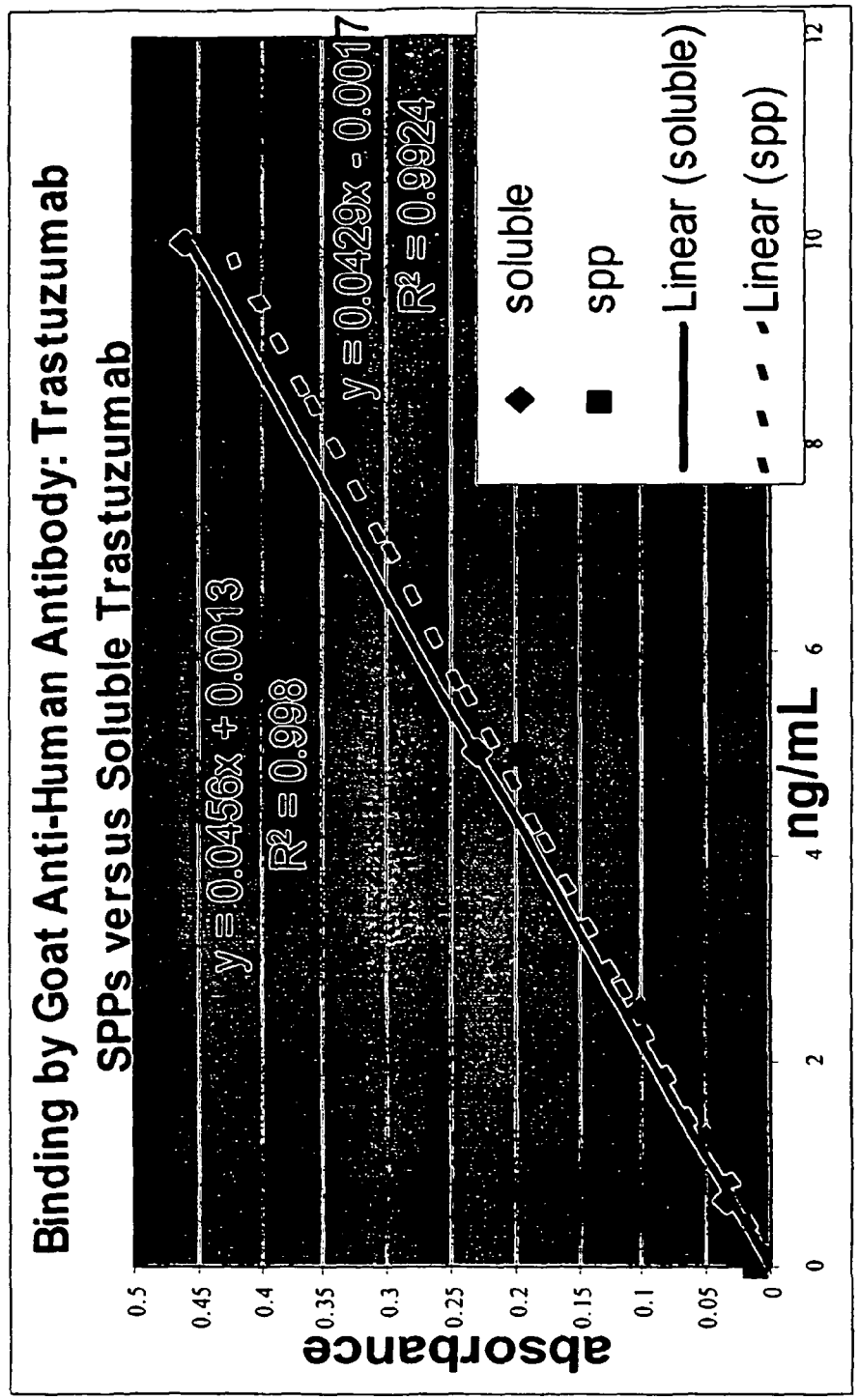
Figure 14: ELISA to Measure the Ability of Trastuzumab Obtained from Dissolving SPPs and Native, Soluble Trastuzumab to Bind Anti-Human Antibodies

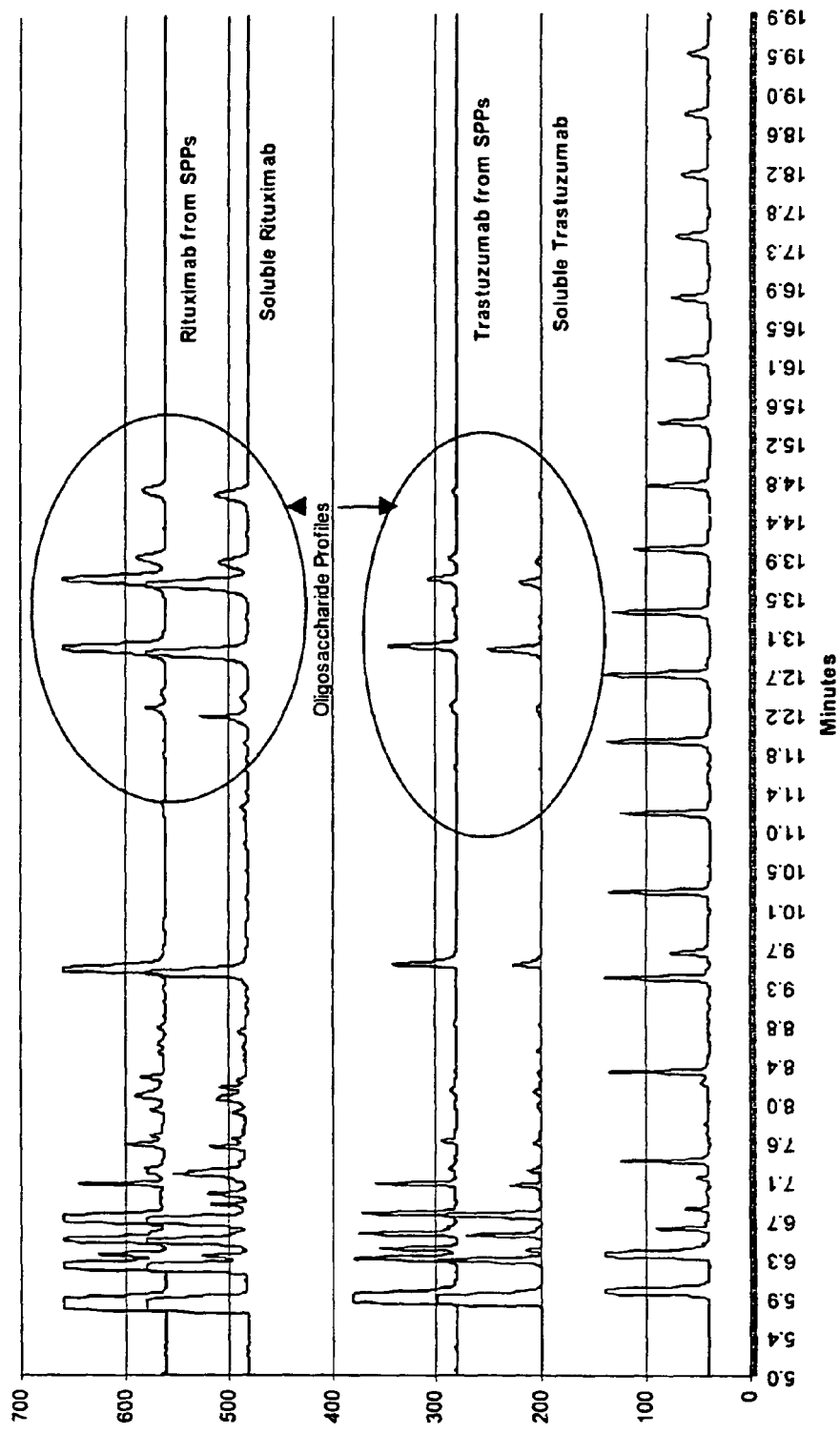
Figure 15: Profiles Comparing the Carbohydrate Constituents of Rituximab (top profile) and Trastuzumab (bottom profile) Obtained from Dissolving SPPs with their Native, Soluble Counterparts

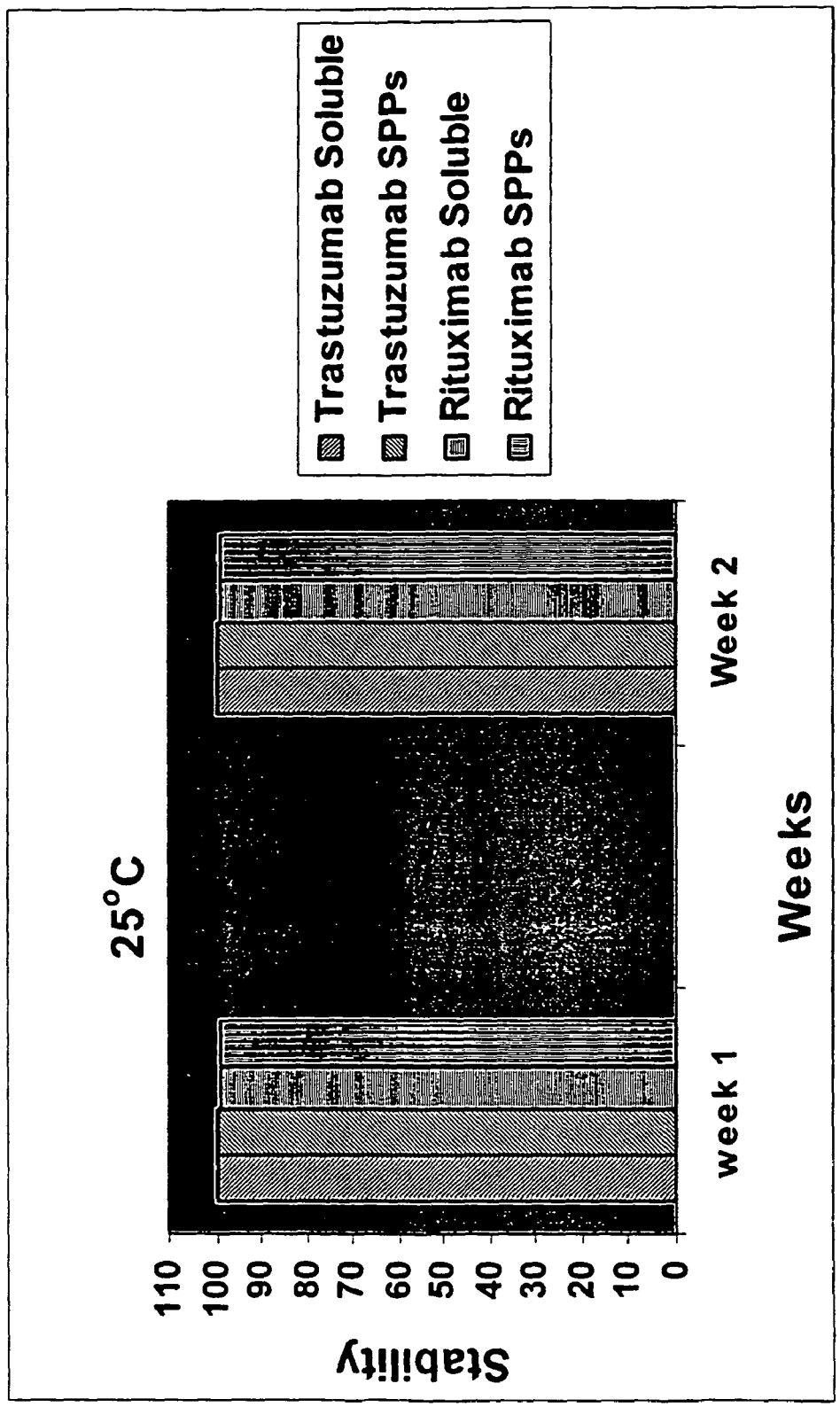
Figure 16: Stability of Rituximab and Trastuzumab SPPs

US 7,998,477 B2

SPHERICAL PROTEIN PARTICLES AND METHODS FOR MAKING AND USING THEM

This application is a continuation of PCT/US02/19870, filed Jun. 21, 2002, which claims priority from provisional application 60/299,989, filed Jun. 21, 2001.

TECHNICAL FIELD OF THE INVENTION

This invention relates to spherical protein particles ("SPPs"), spherical nanocrystalline composite particles and crystalline SPPs, methods for producing them and methods and compositions, including formulations, for using them.

More particularly, the present invention further relates to methods using SPPs, spherical nanocrystalline composite particles and crystalline SPPs for biological delivery to humans and animals. More specifically, the SPPs, spherical nanocrystalline composite particles and crystalline SPPs of this invention can be used to provide alternative dosage/delivery forms, e.g., aerosol, needleless injection, for delivery of biologically active pharmaceutical proteins.

The present invention further relates to methods using SPPs, spherical nanocrystalline composite particles or crystalline SPPs, or compositions, including formulations, containing them, for biomedical applications, including more particularly, highly concentrated SPP, spherical nanocrystalline composite particle or crystalline SPP compositions, including formulations, that are useful for delivery of large amounts of proteins in a small volume to a subject, when and where they are needed. According to one embodiment of this invention, SPPs, spherical nanocrystalline composite particles or crystalline SPPs are used as a carrier-free delivery system which can slowly release biologically active protein to a subject, where and when they are needed. According to an alternate embodiment of this invention, pharmaceutical ingredients or excipients can be added to SPPs, spherical nanocrystalline composite particles or crystalline SPPs to make compositions comprising SPPs, spherical nanocrystalline composite particles or crystalline SPPs. One embodiment of a composition according to this invention is a formulation. A formulation comprises SPPs, spherical nanocrystalline composite particles or crystalline SPPs that are encapsulated in a biocompatible polymeric carrier. In another embodiment, SPPs, spherical nanocrystalline composite particles or crystalline SPPs, and compositions and formulations comprising them, are used for biomedical applications, including delivery of therapeutic proteins and vaccines.

Methods are also provided for preparing stabilized compositions, including formulations, of SPPs, spherical nanocrystalline composite particles or crystalline SPPs, and using such SPPs, spherical nanocrystalline composite particles or crystalline SPPs for biomedical applications, including delivery of therapeutic proteins and vaccines.

Methods are also provided for using SPPs, spherical nanocrystalline composite particles and crystalline SPPs to extract a desired protein of interest from a complex mixture of proteins such as, when the protein is expressed in plant, goat milk, cow milk, cell culture, tissue culture and eggs.

BACKGROUND OF THE INVENTION

Protein drugs are generally formulated for parenteral administration, i.e., injection or infusion, because of their extremely poor bioavailability. Parenteral administration of protein drugs usually requires a visit to the doctor or, in some cases, a hospital. As a result, medical care for patients who require parenteral administration of protein drugs is often expensive and time-consuming. Furthermore, patient compliance is often problematic, especially for those patients who require long-term treatment.

To address this problem, needleless injection technologies, e.g., needleless sub-cutaneous administration, and alternative drug dosage and delivery methods and forms, e.g., dry powder inhalation, skin electroporation, and sustained or controlled release drugs, have been employed.

For use in needleless injection technologies and alternative drug dosage and delivery methods and forms, protein drugs must be manufactured as solid particles to achieve the necessary stability. For many applications, the protein particles to be used must have a well-defined narrow size and morphology. For example, for delivery of a protein drug via inhalation, the diameter of the protein particles to be inhaled must be approximately 2-3 microns, if the main site of action, the alveoli, is to be reached. A number of methods have been employed to prepare micron-sized protein particles, including spray-drying, lyophilization and jet milling. These methods are problematic because they typically denature proteins by heat and mechanical stress. Therefore, there is a need for alternative methods of preparing micron-sized or nanometer-sized protein particles without losing biological activity of the protein. The SPPs, spherical nanocrystalline composite particles and crystalline SPPs according to this invention solve this problem, as well as the problems discussed below.

Ruth et al., Acta Crystallographica D56:524-28 (2000) ("Ruth"), which refers to α-L-iduronidase semi-crystalline spherulites that were made using the hanging drop method of crystallization. The α-L-iduronidase spherulites formed when crystallization solutions at pH 3.0-8.5 were used in the presence of calcium or zinc salts. However, during the process of forming spherulites, the α-L-iduronidase protein underwent a conformational change, possibly due to partial denaturation or unfolding of the α-L-iduronidase protein. The methods of the present invention avoid any change of conformation or resulting loss of biological activity.

U.S. Pat. No. 6,063,910 (the '910 patent), refers to a method of preparing protein microparticles by supercritical fluid precipitation. That method has a number of shortcomings that are overcome by the present invention. The method disclosed in the '910 patent requires suspending the protein of interest in 90% organic solvent, which is not suitable for a number of proteins. Furthermore, the method disclosed in the '910 patent yields particles that are precipitates, unlike the methods of the present invention, which, in some embodiments, could yield SPPs that are crystalline in nature. In addition, the particles resulting from the method of the '910 patent have a diameter of less than 5 microns, while the SPPs, spherical nanocrystalline composite particles or crystalline SPPs of the present invention form particles that range in diameter from about 0.04 to about 200 microns and possibly even larger.

Additional methods of preparing protein particles have also been disclosed, e.g., Bustami R. T. et al., Pharmaceutical Research 17:1360-66 (2000) ("Bustami"). Bustami refers to a method of forming spherical microparticles of proteins using high pressure modified carbon dioxide. The particles formed using the Bustami method are only about 0.1-0.5 microns in diameter, while the method of producing SPPs, spherical nanocrystalline composite particles or crystalline SPPs of the present invention leads to particles that range in diameter from about 0.04 to about 300 microns. Furthermore, in Bustami, the proteins that were formed into microparticles lost up to 60% (for recombinant human deoxyribonuclease (rhDNase)) of their biological activity as a result. Using the methods of the present invention, no loss of biological activity is expected. Finally, the method of Bustami apparently induces protein aggregation, while the method of the present invention does not.

In principle, dried SPPs, spherical nanocrystalline composite particles or crystalline SPPs may also be prepared by lyophilization. See, e.g. Morita T. et al., Pharmaceutical Research 17:1367-73 (2000) ("Morita"). Morita refers to a method of forming spherical fine protein microparticles through lyophilization of a protein-polyethylene glycol (PEG) aqueous mixture. The method in Morita relies on phase separation (unlike the methods herein) followed by lyophilization to yield spheres that have a diameter of 2-3 microns. The methods of the present invention invention lead to the formation of distinct particles that can be isolated by centrifugation, filtration or lyophilization. Also, the SPPs, spherical nanocrystalline composite particles or crystalline SPPs of the present invention form particles that range in diameter from about 0.04 to about 300 microns. Furthermore, the method disclosed in Morita requires the addition of organic solvents, e.g., methylene chloride, to remove the PEG used in a previous step, which, as stated above, is not suitable for a number of proteins. In addition, the SPPs, spherical nanocrystalline composite particles or crystalline SPPs of the present invention are suitable for transfer out of the mother liquor used in their formation and into other solvents, e.g. aqueous isopropyl alcohol. Also, the method disclosed in Morita requires the use of PEG, which may or may not stabilize the protein being used. In contrast, the methods of this invention allow for the use of reagents other than PEG, that may be more capable of stabilizing the protein of interest. For example, the methods of this invention may utilize ammonium sulfate, which generally stabilizes proteins, and which cannot be used in the method disclosed in Morita.

Another limitation of the Morita method is that the disclosed technique involves rapid cooling of the material and can be applied only to freeze stable products. The aqueous solution is first frozen to between −40 and −50° C. Then, the ice is removed under vacuum. Ice formation is usually destructive to the protein crystal lattice, which destabilizes the protein molecule, and sometimes leads to the formation of amorphous precipitate. The methods of the present invention avoid this problem.

SUMMARY OF THE INVENTION

The present invention overcomes the above-described obstacles.

More particularly, the present invention relates to a simple, efficient, high yield method of making SPPs, spherical nanocrystalline composite particles and crystalline SPPs that range in size from about 0.5 to about 50 microns in diameter, more preferably from about 0.04 to about 300 microns in diameter. The SPPs, spherical nanocrystalline composite particles and crystalline SPPs can be made in batches enabling downstream processing of proteins, the extraction of a protein of interest and removal of aggregates. Buffers, e.g., glycine, sodium acetate, phosphate, citrate, Tris, borate, and protein crystallizing agents, e.g., precipitants such as ammonium sulfate, polyethylene glycol (PEG), PEG monomethyl ether, sodium formate, and sometimes other additives, e.g., propylene or ethylene glycol, appear to be important to the successful formation of SPPs, spherical nanocrystalline composite particles and crystalline SPPs according to this invention. These reagents are added slowly to bring about a very gradual increase in the concentration of the precipitating agents. Although dialysis is particularly suited for this purpose, direct addition in a controlled manner will also yield SPPs, spherical nanocrystalline composite particles and crystalline SPPs according to this invention.

In the methods of this invention, reagents such as ammonium sulfate, polyethylene glycol (PEG), PEG monomethyl ether (PEG MME) and sodium formate, that tend to cause immediate precipitation if they are directly applied to protein solutions, are instead allowed to equilibrate slowly over time by dialysis. In essence, a more concentrated crystallization buffer is allowed to pass slowly through a dialysis membrane, where it equilibrates with a less concentrated solution that contains the protein of interest. Over time, this process raises the effective concentration of the protein of interest, thereby causing a slow precipitation that leads to the formation of SPPs, spherical nanocrystalline composite particles and crystalline SPPs.

An important element of this process is that the protein be in a buffer that can support pH at a particular level, e.g. sodium acetate at pH 5.5. Furthermore, certain additives, e.g. propylene glycol, appear to be important for the successful formation of SPPs, spherical nanocrystalline composite particles and crystalline SPPs. The methods of this invention are applicable to a broad range of proteins having wide ranges of molecular weight (MW), isoelectric point (pI) and purity. Proteins suitable for this method include, but are not limited to, antibodies and antibody fragments, glycoproteins, enzymes, protein hormones, viruses and viral proteins, receptors, diagnostic proteins and peptides. The methods of this invention permit production of SPPs, spherical nanocrystalline composite particles and crystalline SPPs for a number of monoclonal antibodies and heavily glycosylated glycoproteins with pI's that vary from about 4.0 to about 10.0. SPPs, spherical nanocrystalline composite particles and crystalline SPPs of the present invention are quite stable and retain full solubility, even in dilute buffer systems.

A further embodiment of this invention relates to a method whereby specific proteins may be purified away from complex protein mixtures, e.g., when protein is expressed in cells including, inter alia, bacteria, eggs, goat and cow's milk, plants, cell and tissue culture etc.

A further embodiment relates to a method of removing aggregated proteins from solutions containing aggregated and non-aggregated proteins.

A further embodiment of this invention includes crosslinked and/or encapsulated SPPs, spherical nanocrystalline composite particles and crystalline SPPs.

This invention also relates to SPPs, spherical nanocrystalline composite particles or crystalline SPPs of biologically active proteins, or compositions, including formulations, comprising SPPs, spherical nanocrystalline composite particles or crystalline SPPs of biologically active proteins.

BRIEF DESCRIPTION OF THE DRAWINGS

FIG. 1 depicts the morphology of monoclonal antibody (Mab) SPPs, prepared as described.
A: Infliximab (Remicade™) SPPs (see Example 1);
B: Rituximab (Rituxan™) SPPs (see Example 2);
C: Trastuzumab (Herceptin™) SPPs (see Example 3).

FIG. 2 depicts a comparison between the Fourier Transform Infrared Spectra (FTIR) of Trastuzumab (Herceptin™) antibody SPPs suspended in mother liquor and FTIR of the native, soluble Trastuzumab counterpart. The Trastuzumab component of the SPPs had about the same secondary structure as its native, soluble counterpart, indicating that the process of forming Trastuzumab SPPs did not harm the integrity of the intact antibody or alter its native structure. See Example 14.

FIG. 3 depicts a comparison between the Fourier Transform Infrared Spectra (FTIR) of Infliximab (Remicade™) antibody SPPs suspended in mother liquor and FTIR of the native, soluble Infliximab counterpart. The Infliximab component of the SPPs had about the same secondary structure as its native, soluble counterpart, indicating that the process of forming Infliximab SPPs did not harm the integrity of the intact antibody or alter its native structure. See Example 14.

FIG. 4 depicts a comparison between the Fourier Transform Infrared Spectra (FTIR) of Rituximab (Rituxan™) antibody SPPs suspended in mother liquor and FTIR of the native, soluble Rituximab counterpart. The Rituximab component of the SPPs had about the same secondary structure as its native, soluble counterpart, indicating that the process of forming Rituximab SPPs did not harm the integrity of the intact antibody or alter its native structure. See Example 14.

FIG. 7 shows an SDS-PAGE gel comparing the stability of Rituximab (Rituxan™) and Trastuzumab (Herceptin™) obtained from dissolved SPPs with the stability of their native, soluble Rituximab and Herceptin counterparts. See Example 20.

FIG. 8 shows an SDS-PAGE gel depicting the selective fractionation/purification of Infliximab (Remicade™), Rituximab (Rituxan™) and Trastuzumab (Herceptin™) from milk proteins by preparation of SPPs. See Example 11.

FIG. 9 is a plot showing that Rituximab obtained from dissolving Rituximab SPPs (made according to the method of Example 2) according to Example 19 induced Direct Cytotoxicity of RAJI lymphoma cells that was comparable to that of its native, soluble Rituximab counterpart assayed under identical conditions. See Example 16.

FIG. 10 is a plot showing that Rituximab obtained from dissolving Rituximab SPPs (made according to the method of Example 2) according to Example 19 induced Complement Dependent Cytotoxicity (CDC) of RAJI lymphoma cells that was comparable to that of its native, soluble Rituximab counterpart assayed under identical conditions. See Example 17.

FIG. 11: CD spectra of Trastuzumab. See Example 47.

FIG. 12: CD spectra of Rituximab. See Example 47.

FIG. 13: CD spectra of Infliximab. See Example 47.

FIG. 14: A plot showing the results of an ELISA comparing the ability of Trastuzumab obtained from dissolving SPPs to bind anti-human antibodies with that of its soluble counterpart (native, soluble Trastuzumab). The results demonstrate that the process of forming Trastuzumab SPPs did not alter the conformation of the native Trastuzumab antibody. See Example 48.

FIG. 15: Carbohydrate profiles comparing the carbohydrate constituents of Rituximab (top profile) and Trastuzumab (bottom profile), obtained from dissolving SPPs, versus their native, soluble counterparts. The results show that the antibodies obtained from dissolving antibody SPPs have the same carbohydrate content as their native, soluble counterparts, demonstrating that the process of forming Rituximab and Trastuzumab SPPs did not alter the carbohydrate content of the native Rituximab and Trastuzumab antibodies. See Example 50.

FIG. 16 shows a plot comparing the stability of Rituximab and Trastuzumab SPPs resuspended in solutions according to Example 25 with that of their native, soluble counterparts.

DETAILED DESCRIPTION OF THE INVENTION

Figure 5:
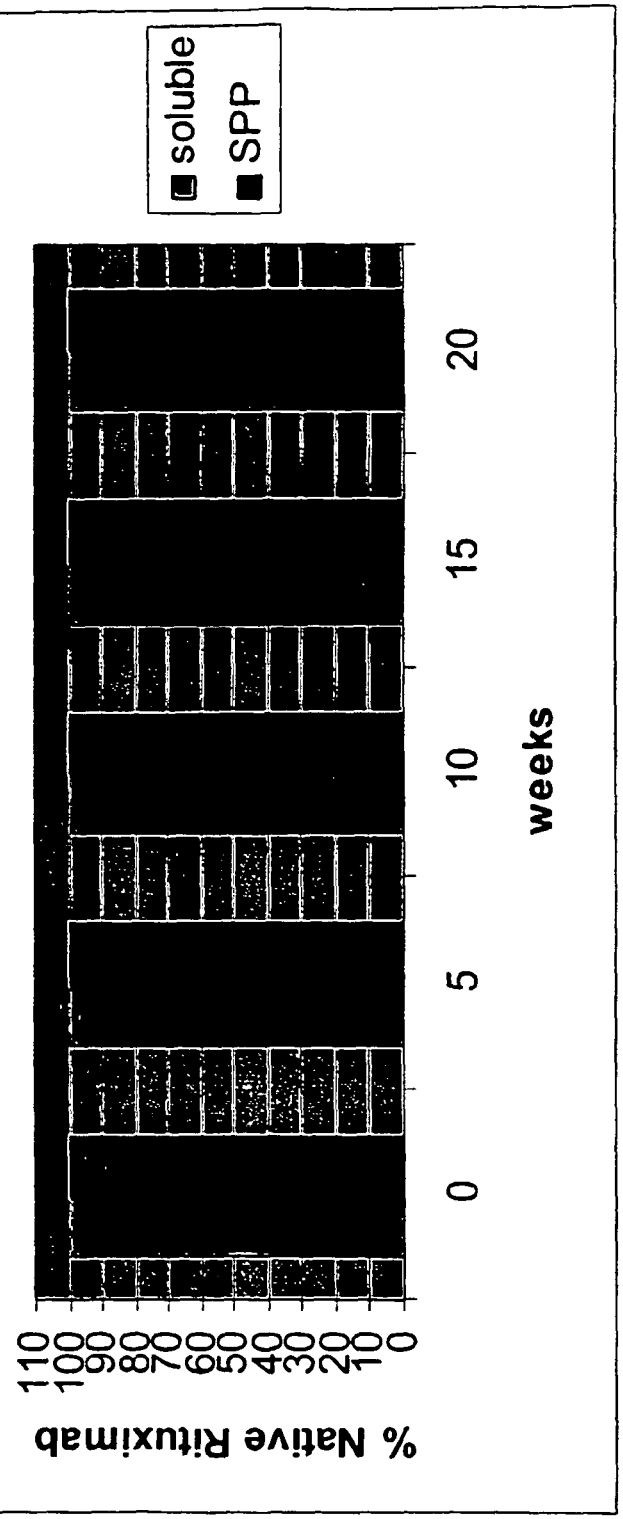
FIG. 5 depicts the results of an analysis of the stability of Rituximab (Rituxan™) obtained from dissolved Rituximab SPPs compared with the stability of native, soluble Rituximab at 4° Centigrade. See Example 20.

In order that the invention herein described may be more fully understood, the following detailed description is set forth. In the description, the following terms are employed:

Amorphous solid—a non-crystalline solid form of protein, sometimes referred to as amorphous precipitate, which has no molecular lattice structure characteristic of the crystalline solid state.

Antibody—a glycoprotein of approximate MW 150 kD that is produced by the so-called humoral arm of the immune system of vertebrates in response to the presence of foreign molecules in the body. Antibodies are essential for the prevention and resolution of infection by microorganisms, e.g. parasites, bacteria and viruses. Antibodies perform this function by recognizing and binding, in a highly specific manner, protein (or, sometimes, other organic molecules including polysaccharides, glycoproteins, lipids, or nucleic acids) configurations called antigens (or epitopes) on invading microorganisms and their products. Antibodies bind their target antigens through highly specific interactions between hypervariable domains, called antigen-binding sites, on the antibody, and the epitope itself. Upon binding to the antigen, antibodies activate one or more of the many effector systems of the immune system that contribute to the neutralization, destruction and elimination of the infecting microorganism.

Antibodies are also used for the treatment of cancer, inflammation, cardiovascular disease, and transplant rejection, by their specific binding and subsequent neutralization of the cellular targets, which are involved in disease states. For example, the monoclonal antibody Infliximab binds to tumor necrosis factor and neutralizes its role in inflammation by blocking its interaction with cell surface receptor; while Rituximab targets malignant B lymphocytes by binding to their cell surface CD20 antigen.

Examples of specific antibodies that may be incorporated into SPPs, spherical nanocrystalline composite particles or crystalline SPPs, or compositions, including formulations, comprising them, according to this invention include, inter alia, anti-TNF antibodies, anti-CD3 antibodies, anti-CD20 antibodies, anti-CD25 antibodies, anti-CD33 antibodies, anti-CD40 antibodies anti-HER2 antibodies, anti-HBV antibodies, anti-HAV antibodies, anti-HCV antibodies, anti-GPIIb/IIIa receptor antibodies, anti-RSV antibodies, anti-HIV antibodies, anti-HSV antibodies and anti-EBV antibodies.

A single antibody molecule has a structure composed of two identical heavy chains (each of approximate MW 50 kD) covalently bound to each other, and two identical light chains (each of approximate MW 25 kD), each covalently bound to one of the heavy chains. The four chains are arranged in a classic "Y" motif. The bottom "leg" of the "Y" is called the Fc region ("c" stands for "crystallizable") and is used to anchor the antibody within cell membranes, and also to bind macrophage cells and activate complement. The two "arms" at the top of the "Y" are called Fab regions (the "ab" stands for "antigen-binding"). Each Fab region contains a constant region (at the juncture of the Fab and the Fc regions) and a variable region (which extends to the tip of the "Y"). Each variable region contains identical antigen-binding sites (at regions within the variable regions called "hypervariable" regions) at each tip of the "Y". Thus, each Fab region has one antigen-binding site, and the complete antibody molecule therefore has two antigen-binding sites (i.e., is "bispecific"). The two antigen-binding sites on a naturally occurring antibody are identical to each other, and therefore the antibody is specific for one antigen (i.e., is "mono-specific"). A number of molecular fragments of antibody molecules have been isolated to date. These do not occur naturally, but are engineered from one or more complete antibody molecules. These fragments include Fab fragments (a single Fab that is isolated form a complete antibody by digestion with the enzyme papain), and F(ab')$_2$ fragments (two Fabs covalently-bound to each other, produced by digesting the antibody with the enzyme pepsin). Fab fragments are monospecific, while F(ab')$_2$ fragments are bispecific. Recently, a number of engineered antibody fragments have been introduced. These include double-stranded Fv (dsFv) fragments and single-chain Fv (scFv) fragments (the "v" stands for "variable" in both cases). A dsFv fragment consists of an Fab fragment minus the constant regions, i.e., consisting only of the variable regions of a heavy and light chain covalently bound to each other. A scFv fragment is a single polypeptide chain, consisting the variable region of a heavy chain linked via a peptide linker to the variable region of a light chain. Classically, both the dsFv and the scFv are monovalent (and thus mono-specific). However, two dsFv fragments or two scFv fragments can themselves be linked to form a bispecific fragment (which would be analogous to an F(ab')$_2$ fragment without the constant regions). Furthermore, it is possible to link two dsFv fragments or scFv fragments with different antigen-binding sites (i.e., different specificities), to form a bi-specific fragment. Such fragments may be used as either research tools or therapeutic or diagnostic reagents.

There are five classes of antibodies (also called immunoglobulins) in humans: IgG, IgM, IgA, IgD, and IgE, each with its own unique characteristics and function. IgG, IgD, and IgE are all made up of one antibody molecule, while IgA can be made up of one, two or three such molecules and IgM consists of five. Furthermore, in humans, there are four subclasses of IgG (IgG1, IgG2, IgG3, or IgG4), and two subclasses each of IgM and IgA (1 and 2, respectively). For example, the monoclonal antibody Rituximab (Rituxan™) is an IgG1 antibody.

Though naturally occurring antibodies are derived from a single species, engineered antibodies and antibody fragments may be derived from more than one species of animal, i.e., may be chimeric. To date, mouse (murine)/human chimeric antibodies have been generated, though other species combination are possible. Chimeric antibodies have been further broken down into two subtypes: chimeric and humanized. Chimeric murine/human antibodies contain approximately 75% human and 25% mouse amino acid sequences, respectively. The human sequences represent the constant regions of the antibody while the mouse sequences represent the variable regions (and thus contain the antigen-binding sites) of the antibody. The rationale for using such chimeras is to retain the antigen specificity of the mouse antibody but reduce the immunogenicity of the mouse antibody (a murine antibody would cause an immune response against it in species other than the mouse) and thus be able to employ the chimera in human therapies. Chimeric antibodies also include those which comprise CDR regions from different human antibodies.

Alternatively, chimeric antibodies comprise framework regions from one antibody and CDR regions from another antibody. Chimeric antibodies also include those which comprise CDR regions from at least two different human antibodies. Humanized antibodies contain approximately 90% (or more) human amino acid sequences. The only murine sequences present are those for the hypervariable region (that are the actual antigen-binding sites contained within the variable region). Humanized antibodies have minimal mouse immunogenicity as compared with chimeric antibodies.

Engineered antibodies and antibody fragments also include, inter alia, non-glycosylated antibodies and antibody fragments.

There are generally two types of antibodies that can be distinguished by their specificities: polyclonal antibodies and monoclonal antibodies. Polyclonal antibodies are those that are found as the immunoglobulin fraction of blood, and are essentially a polyclonal mixture of many different types of antibodies specific for the different antigens the individual has been exposed to (i.e., they originate from many different clones of B lymphocytes (or B cells), the cell that produces antibodies).

Monoclonal antibodies are antibodies of a single specificity, i.e., that are derived from a single clone of B lymphocytes (B cells). These antibodies have exquisite specificity for their target antigens and also can be produced in high amounts (i.e., high titres). They are useful as markers for specific antigens (e.g., cancer antigens), as diagnostic agents (e.g., in assays to detect viruses like HIV-1), and as therapeutic agents. Intact monoclonal antibodies are those that have a classic molecular structure that includes two complete heavy chains and two complete light chains. This is distinguished from antibody fragments, such as Fab, F(ab')$_2$, Fc fragments, dsFv fragments, and scFv fragments.

Traditionally, monoclonal antibodies have been produced by fusing the antibody-producing B cell with an immortal hybridoma cell to generate B cell hybridomas, which continually produce monoclonal antibodies in cell culture. Currently, however, monoclonal antibodies may be produced in vivo in large quantities in genetically-modified animals, such as cows and goats (Genzyme Transgenics), pigs and rabbits (Pharmingen, PPL Therapeutics), chickens (Tranxenogen), and in plants, such as tobacco and corn (Epicyte, Integrated Protein Technologies, Meristem Croptech, and others). For example, large amounts of monoclonal antibodies can be found in the milk of goats (Genzyme Transgenics). Antibodies from all such sources may be used to prepare SPPs, spherical nanocrystalline composite particles and crystalline SPPs according to this invention. Furthermore, as a result of transgenics, mice have been modified to contain and express the entire human B cell genome (which encodes human antibodies). Therefore, such transgenic mice (Abgenix) are a source of human antibodies according to this invention. It should be noted that glycosylation is specific to the animal that is producing the antibodies. For example, this means that human antibodies from sources other than humans will have subtly different glycosylation profiles. Therefore, the intact antibodies or single-chain Fv fragments useful in this invention may display modified glycosylation or be deglycosylated. Antibody SPPs, spherical nanocrystalline composite antibody particles and crystalline antibody SPPs which may be generated according to this invention also include derivatized antibodies. Such antibodies include those derivatized with polyethylene glycol or at least one carbohydrate moiety or least one methyl or ethyl group.

Clinically relevant antibodies may also be classified according to the therapeutic area in which they are to be employed. Such antibodies include, for example, those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. Such antibodies also include antibodies for radioimmunotherapy. Antibodies which may be crystallized according to the present invention include, for example, Abciximab, Palivizumab, Murumonab-CD3, Gemtuzumab, Trastuzumab, Basiliximab, Daclizumab, Etanercept and Zevalin.

Antibody activity release rate—the quantity of intact antibody dissolved per unit time. The quantity of single chain Fv antibody fragment dissolved per unit time is the "single-chain Fv antibody fragment release rate".

Antibody SPP—an SPP, spherical nanocrystalline composite particle or crystalline SPP that is formed by the slow, controlled precipitation of an antibody or a combination of antibodies. Antibody SPPs, spherical nanocrystalline composite antibody particles or crystalline antibody SPPs may be combined with any other pharmaceutically or diagnostically acceptable second component to form a composition. Alternatively, antibody SPPs, spherical nanocrystalline composite antibody particles or crystalline antibody SPPs may encapsulated within a polymeric carrier to form coated particles (a formulation, which is one embodiment of a composition).

Alternatively, antibody SPPs, spherical nanocrystalline composite antibody particles, crystalline antibody SPPs, or compositions or formulations thereof, may be formed from antibody fragments including, inter alia, single-chain Fv antibody fragments.

Antibody SPPs, spherical nanocrystalline composite antibody particles or crystalline antibody SPPs have a spherical morphology and have a size range of from about 0.04 to about 300 microns in diameter.

Antigen—any substance or material that is specifically recognized by an antibody. Antigens are typically small pieces of proteins (peptides) found on the surfaces of cells or invading microorganisms. Antibodies are thought to specifically recognize antigens as small as four amino acids in length, and the substitution of only one amino acid can abolish antibody recognition of that particular antigen.

Antigenicity—the ability of an antigen to be bound by an antibody that has been raised previously against that antigen. An antigen is said to be in its antigenic conformation when it can be bound by the antibody targeted to it. This is different from immunogenicity, which is the ability of an antigen to elicit the production of antibodies that will in turn neutralize the microorganism displaying that antigen in its native conformation.

Anti-idiotypic antibody—antibodies having specificity for the antigen-binding sites of other antibodies. Anti-idiotypic antibodies are generated in the following manner: an antigen elicits the production of antibodies (called Ab-1 or idiotypes) that are specific for that antigen. These antibodies (idiotypes) are then used as immunogens themselves to elicit a second generation of antibodies that are specific for Ab-1. These second generation antibodies (Ab-2) are called anti-idiotypic antibodies (or anti-idiotypes), and either mimic, or are closely related to, the initial antigen used to generate Ab-1. Such reactions also occur naturally in vivo, in response to antigenic stimulation, and by means of these antibody-antibody interactions, the immune system is able to, in essence, interact with itself. It has been postulated that by exploiting this capability, anti-idiotypic antibodies can be used to prevent certain infections, and treat some kinds of cancers and various immune and autoimmune diseases.

Antibody half-life—for antibodies in vivo, the time in which a given amount of antibodies are reduced to 50% of its initial concentration. IgG typically has a half-life of about 21 days (though IgG3 has a half-life of only 7 days), while IgM, A, D, and E have typical half-lives of 10 days, 6 days, 3 days, and 2 days, respectively. The time in which a given amount of a single chain Fv antibody fragment is reduced to 50% of its initial concentration is "the single chain Fv antibody fragment half-life".

Antibody loading—the antibody content of compositions, including formulations, of antibody SPPs, spherical nanocrystalline composite antibody particles or crystalline SPPs, as calculated as a percentage by weight of antibody relative to the weight of the dry composition. A typical range of antibody loading is from about 1% to about 80%. The single chain Fv antibody fragment content of compositions, including formulations, of Fv antibody fragment SPPs, spherical nanocrystalline composite Fv antibody fragment particles or crystalline Fv antibody fragment SPPs, as calculated as a percentage by weight of the fragment relative to the weight of the dry composition is "the single chain Fv antibody fragment loading."

Antibody release—the release of active protein from a polymeric carrier, as controlled by one or more of the following factors: (1) degradation of the polymer matrix; (2) rate of crystal dissolution within the polymer matrix; (3) diffusion of dissolved protein through the polymer matrix; (4) protein loading; and (5) diffusion of biological medium into the antibody crystal/polymer matrix.

Biocompatible Polymers—polymers that are non-antigenic (when not used as an adjuvant), non-carcinogenic, non-toxic and which are not otherwise inherently incompatible with living organisms. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutryate), poly (caprolactone) and poly (dioxanone); poly (ethylene glycol), poly (hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Biodegradable polymers—polymers that degrade by hydrolysis or solubilization. Degradation can be heterogenous—occurring primarily at the particle surface, or homogenous—degrading evenly throughout the polymer matrix, or a combination of such processes.

Bioimmunoassay for the Determination of Biological Activity of Antibodies—Any immunoassay that may be used to determine the biological activity of an antibody, including, inter alia, direct cytotoxicity, complement dependent cytotoxicity (CDC), and antibody-dependent cell-mediated cytotoxicity (ADCC). See Examples 15-18 and FIGS. 9 and 10.

Biological macromolecule—biological polymers such as proteins, deoxyribonucleic acids (DNA) and ribonucleic acids (RNA). For the purposes of this application, biological macromolecules are also referred to as macromolecules.

Complement—the collective term for about 20 enzymes, proenzymes and other proteins that form one of the principal effector mechanisms of immunity. Although antigen-nonspecific in itself, the complement system is a final effector mechanism of highly specific antibody-mediated immune responses.

Composition—A mixture of different components sustained in a defined ratio. An SPP composition, spherical nanocrystalline composite particle composition or crystalline SPP composition comprises an SPP, spherical nanocrystalline composite particle or crystalline SPP in combination with one or more pharmaceutically or diagnostically acceptable ingredient or excipients, including sugars and biocompatible polymers. One embodiment of a composition is a formulation, which is an SPP, spherical nanocrystalline composite particle or crystalline SPP according to this invention, which has been encapsulated within a polymeric carrier to form coated particles (i.e., a composition wherein at least one of the ingredients added to an SPP, spherical nanocrystalline composite particle or crystalline SPP is a polymer). Examples of excipients are described in the *Handbook of Pharmaceutical Excipients*, published jointly by the American Pharmaceutical Association and the Pharmaceutical Society of Great Britain. A "formulation-for-decontamination" is a formulation selected from the group consisting of: formulations for decontamination of chemical wastes, herbicides, insecticides, pesticides and environmental hazards.

Controlled dissolution—dissolution of a SPP, spherical nanocrystalline composite particle or crystalline SPP of a protein, including, inter alia, an intact antibody or a single chain Fv antibody fragment, or of a composition or formulation comprising such SPPs, spherical nanocrystalline composite particles or crystalline SPPs, in a controlled manner. Dissolution is controlled by a factor selected from the group consisting of the following: the surface area of said SPP, spherical nanocrystalline composite particle or crystalline SPP; the size of said SPP, spherical nanocrystalline composite particle or crystalline SPP; the shape of said SPP, spherical nanocrystalline composite particle or crystalline SPP, the concentration of the excipient component of an SPP, spherical nanocrystalline composite particle or crystalline SPP composition or formulation; the number and nature of excipient components; the molecular weight of the excipient components, the nature of polymeric carriers, and combinations thereof.

Co-polymer—a polymer made with more than one monomer species.

Crystal—crystals, e.g., crystalline SPPs or nanocrystals (single nanocrystals or aggregates of nanocrystals form spherical nanocrystalline composite particles), are one form of the solid state of matter, which is distinct from a second form—the amorphous solid state, which exists essentially as an unorganized solid. Crystals are regular three-dimensional arrays of atoms, ions, molecules (e.g., proteins such as antibodies), or molecular assemblies (e.g., antigen/antibody complexes). Crystals are lattice arrays of building blocks called asymmetric units (which consist of the substance to be crystallized) that are arranged according to well-defined symmetries into unit cells that are repeated in three-dimensions. See Giegé, R. and Ducruix, A. Barrett, *Crystallization of Nucleic Acids and Proteins, a Practical approach*, 2nd ed., pp. 1-16, Oxford University Press, New York, N.Y., (1999).

Diagnostically effective amount—an amount of an SPP, spherical nanocrystalline composite particle or crystalline SPP, or a composition or formulation thereof, which is effective to diagnose an infection by a microorganism, in a living organism to whom it is administered over some period of time.

Drying of SPPs, Spherical Nanocrystalline Composite Particles or Crystalline SPPs—removal of water, organic solvent or liquid polymer by means including drying with $N_2$, air or inert gases, vacuum oven drying, lyophilization, washing with a volatile organic solvent followed by evaporation of the solvent, or evaporation in a fume hood. Typically, drying is achieved when the SPPs, spherical nanocrystalline composite particles or crystalline SPPs become a free flowing powder. Drying may be carried out by passing a stream of gas over wet SPPs, spherical nanocrystalline composite particles or crystalline SPPs. The gas may be selected from the group consisting of: nitrogen, argon, helium, carbon dioxide, air or combinations thereof.

Effective amount—an amount of an SPP, spherical nanocrystalline composite particle or crystalline SPP or a composition or formulation thereof, which is effective to treat, immunize, boost, protect, repair or detoxify the subject or area to which it is administered over some period of time.

Emulsifier—a surface active agent which reduces interfacial tension between SPPs, spherical nanocrystalline composite particles or crystalline SPPs and a solution. Alternatively, an emulsifier would reduce interfacial tension between polymer-coated SPPs, spherical nanocrystalline composite particles or crystalline SPPs and a solution.

Glycoprotein—a protein or peptide covalently linked to a carbohydrate. The carbohydrate may be monomeric or composed of oligosaccharides.

Homo-Polymer—a polymer made with a single monomer species.

Immunotherapeutic proteins—a protein is immunotherapeutic when it has the activity of inducing protective immunity to a tumor cell, virus, or bacteria or stimulating the immune system to reduce or eliminate said tumor cell, virus or bacteria.

Insoluble and stable form—a form of SPP, spherical nanocrystalline composite particle or crystalline SPP which is insoluble in aqueous solvents, organic solvents or aqueous-organic solvent mixtures and which displays greater stability than the soluble form of the protein component of the SPP, spherical nanocrystalline composite particle or crystalline SPP. In any embodiment, SPPs, spherical nanocrystalline composite particles or crystalline SPPs may be active in insoluble form. And in one embodiment, SPPs, spherical nanocrystalline composite particles or crystalline SPPs may be active in insoluble form, then dissolve or are removed or digested once their function is complete.

Label—incorporation of a label to an SPP, spherical nanocrystalline composite particle or crystalline SPP. Labels may be selected from the group consisting of radiolabels, enzyme labels, toxins, magnetic agents or drug conjugates.

Liquid polymer—pure liquid phase synthetic polymers, such as poly-ethylene glycol (PEG), in the absence of aqueous or organic solvents.

Macromolecules—proteins, glycoproteins, peptides, therapeutic proteins, DNA or RNA molecules.

Method of Administration—SPPs, spherical nanocrystalline composite particles or crystalline SPPs, or compositions or formulations comprising them, may be appropriate for a variety of modes of administration. These include oral and parenteral administration. Examples of parenteral administration include, but are not limited to, subcutaneous, intravenous, transdermal, intramuscular, pulmonary inhalation, intralesional, topical administration, needleless injection, sub-cutaneous injection, needleless sub-cutaneous administration, or aerosol delivery.

Mother Liquor—the preparation buffer used to make SPPs, spherical nanocrystalline composite particles or crystalline SPPs of macromolecules, e.g., proteins, nucleic acids.

Organic solvents—any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

Peptide—a polypeptide of small to intermediate molecular weight, usually 3 to 35 amino acid residues and frequently but not necessarily representing a fragment of a larger protein.

Pharmaceutically effective amount—an amount of an SPP, spherical nanocrystalline composite particle or crystalline SPP, or a composition or formulation thereof, which is effective to treat a condition in an living organism to whom it is administered over some period of time.

Prophylactically effective amount—an amount of a SPP, spherical nanocrystalline composite particle or crystalline SPP, or a composition or formulation thereof, which is effective to prevent an infection in an individual to whom it is administered over some period of time.

Ingredients—any excipient or excipients, including pharmaceutical ingredients or excipients. Excipients include, for example, the following:

Acidifying Agents
 acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid Aerosol Propellants
 butane, dichlorodifluoromethane, dichlorotetrafluoroethane, isobutane, propane, trichloromonofluoromethane Air Displacements
 carbon dioxide, nitrogen Alcohol Denaturants
 denatonium benzoate, methyl isobutyl ketone, sucrose octacetate Alkalizing Agents
 strong ammonia solution, ammonium carbonate, diethanolamine, diisopropanolamine, potassium hydroxide, sodium bicarbonate, sodium borate, sodium carbonate, sodium hydroxide, trolamine Anticaking Agents (See Glidant)

Antifoaming Agents
 dimethicone, simethicone

Antimicrobial Preservatives
 benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol Antioxidants
 ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient Buffering Agents
 acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate Capsule Lubricants (See Tablet and Capsule Lubricant)

Chelating Agents
 edetate disodium, ethylenediaminetetraacetic acid and salts, edetic acid Coating Agents
 sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein Colors
 caramel, red, yellow, black or blends, ferric oxide Complexing Agents
 ethylenediaminetetraacetic acid and salts (EDTA), edetic acid, gentisic acid ethanolamide, oxyquinoline sulfate Desiccants
 calcium chloride, calcium sulfate, silicon dioxide Emulsifying and/or Solubilizing Agents
 acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax Filtering Aids
 powdered cellulose, purified siliceous earth Flavors and Perfumes
 anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin Glidant and/or Anticaking Agents
 calcium silicate, magnesium silicate, colloidal silicon dioxide, talc Humectants
 glycerin, hexylene glycol, propylene glycol, sorbitol Ointment Bases
 lanolin, anhydrous lanolin, hydrophilic ointment, white ointment, yellow ointment, polyethylene glycol ointment, petrolatum, hydrophilic petrolatum, white petrolatum, rose water ointment, squalane Plasticizers
 castor oil, diacetylated monoglycerides, diethyl phthalate, glycerin, mono- and di-acetylated monoglycerides, polyethylene glycol, propylene glycol, triacetin, triethyl citrate Polymer Membranes
 cellulose acetate Solvents
 acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water Sorbents
 powdered cellulose, charcoal, purified siliceous earth Carbon Dioxide Sorbents
 barium hydroxide lime, soda lime Stiffening Agents
 hydrogenated castor oil, cetostearyl alcohol, cetyl alcohol, cetyl esters wax, hard fat, paraffin, polyethylene excipient, stearyl alcohol, emulsifying wax, white wax, yellow wax Suppository Bases
  cocoa butter, hard fat, polyethylene glycol
Suspending and/or Viscosity-Increasing Agents
  acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum
Sweetening Agents
  aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup
Tablet Binders
  acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup
Tablet and/or Capsule Diluents
  calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar
Table Disintegrants
  alginic acid, microcrystalline cellulose, croscarmellose sodium, corspovidone, polacrilin potassium, sodium starch glycolate, starch, pregelatinized starch
Tablet and/or Capsule Lubricants
  calcium stearate, glyceryl behenate, magnesium stearate, light mineral oil, polyethylene glycol, sodium stearyl fumarate, stearic acid, purified stearic acid, talc, hydrogenated vegetable oil, zinc stearate
Tonicity Agent
  dextrose, glycerin, mannitol, potassium chloride, sodium chloride
Vehicle: Flavored and/or Sweetened
  aromatic elixir, compound benzaldehyde elixir, iso-alcoholic elixir, peppermint water, sorbitol solution, syrup, tolu balsam syrup.
Vehicle: Oleaginous
  almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane
Vehicle: Solid Carrier
  sugar spheres
Vehicle: Sterile
  Bacteriostatic water for injection, bacteriostatic sodium chloride injection
Viscosity-Increasing (See Suspending Agent)
Water Repelling Agent
  cyclomethicone, dimethicone, simethicone
Wetting and/or Solubilizing Agent
  benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol Preferred ingredients or excipients include: Salts of 1) amino acids such as glycine, arginine, aspartic acid, glutamic acid, lysine, asparagine, glutamine, proline, 2) carbohydrates, e.g. monosaccharides such as glucose, fructose, galactose, mannose, arabinose, xylose, ribose and 3) disaccharides, such as lactose, trehalose, maltose, sucrose and 4) polysaccharides, such as maltodextrins, dextrans, starch, glycogen and 5) alditols, such as mannitol, xylitol, lactitol, sorbitol 6) glucuronic acid, galacturonic acid, 7) cyclodextrins, such as methyl cyclodextrin, hydroxypropyl-β-cyclodextrin and alike 8) inorganic salts, such as sodium chloride, potassium chloride, magnesium chloride, phosphates of sodium and potassium, boric acid ammonium carbonate and ammonium phosphate, and 9) organic salts, such as acetates, citrate, ascorbate, lactate 10) emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. A further preferred group of excipients or ingredients includes sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

Polymer—a large molecule built up by the repetition of small, simple chemical units. The repeating units may be linear or branched to form interconnected networks. The repeat unit is usually equivalent or nearly equivalent to the monomer.

Polymeric carriers—polymers used for encapsulation of SPPs, spherical nanocrystalline composite particles or crystalline SPPs for delivery of their protein components, including biological delivery. Such polymers include biocompatible and biodegradable polymers. The polymeric carrier may be a single polymer type or it may be composed of a mixture of polymer types. Polymers useful as the polymeric carrier, include for example, poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (B-hydroxybutryate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, modified starches such as amylose starch, amylopectin starch, hydroxyethyl starch, methacryalate starch, and other starches, and any conventional material that is capable of encapsulating protein SPPs, spherical nanocrystalline composite particles or crystalline SPPs.

Protein—a complex high polymer containing carbon, hydrogen, oxygen, nitrogen and usually sulfur and composed of chains of amino acids connected by peptide linkages. The molecular weight range for proteins includes peptides of 1000 Daltons to glycoproteins of 600 to 1000 kiloDaltons.

Protein delivery system—method or means for administering one or more of an SPP, spherical nanocrystalline composite particle or crystalline SPP of a protein, or a composition or formulation thereof, to a biological entity.

Prophylactically effective amount—an amount of an SPP, spherical nanocrystalline composite particle or crystalline SPP, or a composition or formulation thereof, which is effective to prevent an infection by a microorganism, in a living organism to whom it is administered over some period of time.

Radiolabel—incorporation of a radiolabel to an SPP, spherical nanocrystalline composite particle or crystalline SPP. In situations where the radiolabel has a short half-life, as with $^{131}$I or $^{90}$Y, the radiolabel can also be therapeutic, e.g., used in radioimmunotherapies against cancers. Various methods of labeling polypeptides and glycoproteins are known in the art and may be used. Examples of labels include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, and $^{131}$I.

Reconstitution—dissolution of SPPs, spherical nanocrystalline composite particles or crystalline SPPs or compositions or formulations thereof, in an appropriate buffer or pharmaceutical excipient or ingredient.

Loss of Shelf Stability—the loss of specific activity and/or changes in secondary or tertiary structure of the protein component of an SPP, spherical nanocrystalline composite particle or crystalline SPP, as compared with the soluble protein counterpart over time incubated under specified conditions.

Spherical Protein Particle (SPP)—a discrete protein particle with a morphology that is roughly spherical in nature, and that can be isolated by methods such as centrifugation and filtration. One embodiment of an SPP or a crystalline SPP is a so-called "spherical nanocrystalline composite particle." Spherical nanocrystalline composite particles are protein particles having overall dimensions of about 1 to about 300 micrometers (μm) in diameter. Spherical nanocrystalline composite particles comprise protein crystals, called "nanocrystals", having diameters of from about 40 to about 999 nanometers (nm). These protein nanocrystals may be arranged uniformly throughout the larger spherical nanocrystalline composite particle, or arranged in a layered, shell structure. Furthermore, the nanocrystals may be arranged within the spherical nanocrystalline composite particle in such a way as to form pores and channels with openings that are about 1 nm to about 100 nm across (from edge to edge).

Crystalline Spherical Protein Particle (SPP)—an SPP wherein the protein is in a crystalline form, or is crystalline in nature. A crystalline SPP having a diameter ranging from about 40 nm to about 999 nm would be a "nanocrystalline" SPP.

Loss of Stability—the loss of specific activity and/or changes in the secondary or tertiary structure of the protein component of an SPP, spherical nanocrystalline composite particle or crystalline SPP as compared with the soluble protein counterpart over time while in solution under specified conditions.

Stabilization—the process of preventing aggregation, the loss of specific activity and/or changes in secondary or tertiary structure of the protein component an SPP, spherical nanocrystalline composite particle or a crystalline SPP as compared with the soluble protein counterpart, by preparing compositions or formulations of SPPs, spherical nanocrystalline composite particles or crystalline SPPs with excipients or ingredients.

Therapeutic SPP, Therapeutic Spherical Nanocrystalline Composite Particle or Therapeutic Crystalline SPP—an SPP, spherical nanocrystalline composite particle or crystalline SPP as described above, which is administered to a living organism in a composition or formulation or a pharmaceutical composition or formulation.

Vaccine SPP or Vaccine Spherical Nanocrystalline Composite Particle or Vaccine Crystalline SPP—an SPP, spherical nanocrystalline composite particle or crystalline SPP, the protein component of which is an antigen derived from a pathogenic agent such as a virus, parasite, bacteria or tumor cell. The protein activity of such vaccine SPPs, spherical nanocrystalline composite particles or crystalline SPPs is the induction of protective immune responses specific for a pathogenic agent or tumor.

Preparation of SPPs According to the Methods of this Invention

The SPPs, spherical nanocrystalline composite particles or crystalline SPPs of this invention can be made by slow addition of protein crystallizing/precipitation agents to bring about a very gradual increase in the concentration of the precipitating agents. Dialysis may be used for effecting such a slow change. However, direct addition in a controlled manner is a method that may also yield SPPs, spherical nanocrystalline composite particles or crystalline SPPs. In dialysis, the macromolecule of interest (e.g., enzyme, antibody, hormone) is in low ionic-strength solution. The macromolecule solution is encased in a membrane casing or in a container having a semi-permeable membrane partition. During dialysis, the dialysis membrane selectively allows the passage of small molecules and ions, but pore size prevents passage of the larger macromolecules. The vessel or dialysis tube containing the protein is submerged in a larger volume of liquid that has the desired properties of pH, ionic strength, ligand concentration, etc. The protein solution gradually acquires the desired properties and components. Dialysis is the preferred method of this invention.

Alternatively, SPPs, spherical nanocrystalline composite particles or crystalline SPPs may be generated by direct addition of the precipitants/buffers in a controlled manner (See Example 6).

Production of SPPs, Spherical Nanocrystalline Composite Particles or Crystalline SPPs of Biologically Active Proteins, or Compositions or Formulations Comprising them:

Dialysis Method:

Dialysis is a way of modifying the components and degree of saturation of a protein solution. The macromolecule (e.g., enzyme, antibody or hormone) solution is enclosed in a membrane casing or in a container having a semipermeable membrane partition. The membrane selectively allows the passage of small molecules and ions, but pore size prevents passage of the larger macromolecules. The vessel or dialysis tube containing the protein is submerged in a larger volume of liquid that has the desired properties of pH, ionic strength, ligand concentration, etc. The protein solution gradually acquires the desired properties and components.

Dialysis Using a Slide-A-Lyzer:

A. This dialysis method employs a device called a Slide-A-Lyzer (Pierce Chemicals, Catalog #69570). The Slide-A-Lyzer used herein has a molecular weight cut-off point at 10 kD.

B. Procedure:
1. Take Slide-A-Lyzer units and soak in distilled water overnight.
2. Take another tube such as the lower part of a small Centricon device (Amicon, Catalog #420.8) and fill with 3.8-3.9 ml of, e.g.:

2.05 M ammonium sulfate (calculated assuming saturated ammonium sulfate is a 4.1 M solution at room temperature), 0.1 M buffer (acetate, phosphate, Tris), and 1.5% propylene glycol.

Add the reagents in the following order: 1) water, 2) buffer, 3) propylene glycol, and 4) saturated Ammonium sulfate.

3. Place a 3.5 mm×3.5 mm stirring bar in the lower part of the device. Ensure that it is stirring steadily (no clinging to the wall) in the middle.
4. Place 150-410 µl of the desired protein solution, at a protein concentration approximately equal to 10-20 mg/ml, in the Slide-A-Lyzer. Immerse the membrane such that it is a millimeter or two below the level of the buffer/propylene glycol/ammonium sulfate solution.
5. Put the cap on the Slide-A-Lyzer, tight enough to prevent evaporation. Dialyze for the appropriate time at the appropriate temperature.
6. After dialysis, check the results of the dialysis using HPLC and microscopy, and determine the protein content of the supernatant by measuring absorbance at an Optical Density of 280 nm. Check and harvest whenever appropriate, but not long after the layer of liquid disappeared above the sediment. This is crucial for the following reasons:
a) If the protein has aggregate in it, the aggregate tends to form spheres first, leaving the desired protein as a monomer in the supernatant. At this juncture, the supernatant can be harvested and transferred to another membrane and let dialysis proceed until spheres form.
b) If the antibody has been spiked into clarified non-transgenic milk, the milk proteins tend to form spheres last and therefore it is crucial to stop the dialysis at the right time to achieve efficient fractionation of the desired protein.

Non-Dialysis Method:

A further method of producing SPPs, spherical nanocrystalline composite particles or crystalline SPPs according to this invention does not involve dialysis. Instead, precipitating reagents, e.g. ammonium sulfate, can be slowly added at increments, thereby increasing the concentration of the protein solution in a stepwise manner. The protein solution mixtures are allowed to equilibrate for one hour at each concentration. Samples are periodically analyzed by microscopy to determine sphere formation. Protein content, yield, and the amount of protein remaining in the supernatant are measured by spectroscopy at optical density (OD) of 280 nm and HPLC.

Preparation of SPP, Spherical Nanocrystalline Composite Particles and Crystalline SPP Compositions or Formulations:

According to one embodiment of this invention, SPPs, spherical nanocrystalline composite particles or crystalline SPPs of biologically active proteins, or compositions or formulations comprising them, are prepared by the following process.

First, SPPs, spherical nanocrystalline composite particles or crystalline SPPs of a biologically active protein of interest are generated. Next, excipients or ingredients selected from sugars, sugar alcohols, viscosity increasing agents, wetting or solubilizing agents, buffer salts, emulsifying agents, antimicrobial agents, antioxidants, and coating agents are added directly to the SPP, spherical nanocrystalline composite particle or crystalline SPP preparation. The excipient concentration is typically between about 0.01 to 30% W/W; most preferably between about 0.1 to 10%. The ingredient concentration is between about 0.01 to 90%. The SPP, spherical nanocrystalline composite particle or crystalline SPP concentration is between about 0.01 to 99%.

The preparation buffer is then removed from the SPP, spherical nanocrystalline composite particle or crystalline SPP solution either by filtration or by centrifugation. Subsequently, the SPPs, spherical nanocrystalline composite particles or crystalline SPPs are washed, optionally with solutions of about 50 to about 100% of one or more organic solvents such as, for example, ethanol, methanol, isopropanol or ethyl acetate, either at room temperature or at temperatures between about −20° C. to about 25° C.

The SPPs, spherical nanocrystalline composite particles or crystalline SPPs are then dried either by passing a stream of nitrogen, air, or inert gas over the SPPs, spherical nanocrystalline composite particles or crystalline SPPs. Alternatively, the SPPs, spherical nanocrystalline composite particles or crystalline SPPs are dried by air drying, spray drying, lyophilization or vacuum drying. The drying is carried out for a minimum of about 1 hour to a maximum of about 72 hours after washing, until the moisture content of the final product is below about 10% by weight, most preferably below about 5%. Finally, micronizing (reducing the size) of the SPPs, spherical nanocrystalline composite particles or crystalline SPPs can be performed if desired.

According to one embodiment of this invention, when preparing SPPs, spherical nanocrystalline composite particles or crystalline SPPs of biologically active proteins, or compositions or formulations comprising them, enhancers, such as surfactants, are not added during preparation. Excipients or ingredients are added to the preparation buffer after the SPPs, spherical nanocrystalline composite particles or crystalline SPPs have been prepared, at a concentration of between about 1-10% W/W, alternatively at a concentration of between about 0.1-25% W/W, alternatively at a concentration of between about 0.1-50% W/W. The excipient or ingredient is incubated with the SPPs, spherical nanocrystalline composite particles or crystalline SPPs in the preparation buffer for about 0.1-3 hrs, alternatively the incubation is carried out for 0.1-12 hrs, alternatively the incubation is carried out for 0.1-24 hrs.

In another embodiment of this invention, the ingredient or excipient is dissolved in a solution other than the preparation buffer, and the SPPs, spherical nanocrystalline composite particles or crystalline SPPs are removed from the preparation buffer and suspended in the excipient or ingredient solution. The ingredient or excipient concentrations and the incubation times are the same as those described above.

According to another embodiment of this invention, the protein component of the SPP, spherical nanocrystalline composite particle or crystalline SPP is a protein other than one of the following: α-L-iduronidase or lysozyme or albumin or insulin or human (rh) deoxyribonuclease (DNase) or catalase.

According to another embodiment of this invention, the protein component of the SPP, spherical nanocrystalline composite particle or crystalline SPP is a protein other than all of the following: α-L-iduronidase, lysozyme, albumin, insulin, human (rh) deoxyribonuclease (DNase) and catalase.

Uses for the SPPs, Spherical Nanocrystalline Composite Particles and Crystalline SPPs of this Invention The present invention advantageously provides SPPs, spherical nanocrystalline composite particles or crystalline SPPs of biologically active proteins, or compositions or formulations comprising them. It is desirable to produce SPPs, spherical nanocrystalline composite particles or crystalline SPPs that are pure and stable under storage conditions at ambient or extreme temperatures. Such SPPs, spherical nanocrystalline composite particles or crystalline SPPs constitute a particularly advantageous form for dosage preparations of therapeutics and vaccines. The present invention also provides compositions or formulations for storage of SPPs, spherical nanocrystalline composite particles or crystalline SPPs, as either solid particles or dispersed in a non-aqueous solvent. Furthermore, the invention may be applied to the storage of a single biologically active protein or a mixture of proteins that may, or may not interact with each other.

Also, solid SPP, spherical nanocrystalline composite particle or crystalline SPP preparations can be easily reconstituted to generate ready to use parenteral compositions and formulations having very high protein concentrations. Such protein concentrations are considered to be particularly useful where the formulation is intended for subcutaneous administration. For subcutaneous administration, injection volumes of about 1.5 ml or less are well tolerated. Thus, for proteins that are dosed at about 1 mg/kg on a weekly basis a protein concentration of at least about 50 mg/ml is required and about 100-200 mg/ml is preferred. A most preferred embodiment is an SPP, spherical nanocrystalline composite particle or crystalline SPP composition or formulation having a protein concentration of up to about 400 mg/ml. These concentrations are difficult to achieve in liquid formulations, due to the aggregation problems. They can easily be achieved in the SPP, spherical nanocrystalline composite particle or crystalline SPP preparations, and compositions and formulations thereof, of this invention.

In another embodiment, this invention provides a method for generating SPPs, spherical nanocrystalline composite particles or crystalline SPPs of antibodies, including monoclonal antibodies, and also single-chain Fv (scFv) fragments of antibodies, and using such SPPs, spherical nanocrystalline composite particles or crystalline SPPs in various biomedical applications. Such scfv fragments are constructed by linking the variable region of an antibody heavy chain to a variable region of an antibody light chain through the use of a linker peptide. Due to their small size, scFv fragments allow tissue penetration more readily than do intact antibodies, and therefore may have valuable therapeutic applications for particular indications.

This invention includes the production of SPPs, spherical nanocrystalline composite particles or crystalline SPPs of all of the immunoglobulin classes IgG, IgM, IgA, IgD, IgE, and serum IgA (sIgA) as well as the subclasses IgG1, IgG2, IgG3 and IgG4, IgM1 and IgM2, and IgA1 and IgA2, as well as scfv fragments from all the immunoglobulin classes and subclasses.

In another embodiment, this invention provides a method for rendering biologically active SPPs, spherical nanocrystalline composite particles or crystalline SPPs suitable for storage.

In yet another embodiment of this invention, an aqueous preparation of SPPs, spherical nanocrystalline composite particles or crystalline SPPs can be rendered solid by spinning out the first solvent and washing the remaining SPP, spherical nanocrystalline composite particle or crystalline SPP solid using a second organic solvent to remove water, followed by evaporation of the non-aqueous solvent.

Non-aqueous preparations of SPPs, spherical nanocrystalline composite particles or crystalline SPPs of biologically active proteins are especially useful for parenteral administration, including, e.g., subcutaneous delivery and intramuscular delivery, while solid compositions or formulations are ideally suited for pulmonary administration. As will be appreciated by those of skill in the art, pulmonary delivery is particularly useful for biological macromolecules which are difficult to deliver by other routes of administration.

In another embodiment, SPPs, spherical nanocrystalline composite particles or crystalline SPPs of proteins, including intact antibodies, and SPPs, spherical nanocrystalline composite particles or crystalline SPPs of single chain antibody fragments according to this invention are useful in diagnostic methods and kits. For example, such SPPs, spherical nanocrystalline composite particles or crystalline SPPs may be used in a kit for diagnosing the presence a target antigen or antibody in a sample from a patient or another specimen. Such a kit may comprise a container and, optionally, instructions for use. The SPPs, spherical nanocrystalline composite particles or crystalline SPPs in the kit may be labelled with a detectable label. Methods for detecting a target antigen or antibody in a sample, such as a blood, tumor, cell, or tissue sample, may be carried out by mixing the sample with SPPs, spherical nanocrystalline composite particles or crystalline SPPs of proteins or intact antibodies or single chain antibody fragments according to this invention and determining whether the sample binds to the protein, antibody or fragment. The SPPs, spherical nanocrystalline composite particles or crystalline SPPs used in such methods may be labelled with a detectable label.

Alternatively, SPPs, spherical nanocrystalline composite particles or crystalline SPPs of proteins, such as intact antibodies or single chain antibody fragments according to this invention, are useful in chromatography and purification methods, such as affinity chromatography. For example, affinity matrix purification of a protein may be carried out by:
(a) mixing with a binding buffer SPPs, spherical nanocrystalline composite particles or crystalline SPPs of an intact antibody or SPPs, spherical nanocrystalline composite particles or crystalline SPPs of a single chain Fv antibody fragment, wherein such antibody or antibody fragment has affinity for the protein to be purified;
(b) adding a protein solution containing the protein to be purified to the crystal/buffer mixture;
(c) incubating the entire mixture for a time and at a temperature sufficient to permit binding of the protein to the antibody or antibody fragment;
(d) washing the mixture with a wash buffer; and
(e) eluting the protein with an elution buffer.

Administration and Biological Delivery:

To date, therapeutic proteins, e.g., intact antibodies, have generally been administered by frequent injection or infusion, due to their characteristic negligible oral bioavailability and short plasma life. SPPs, spherical nanocrystalline composite particles and crystalline SPPs, as well as compositions or formulations comprising them (which include microparticulate-based sustained release systems for biologically active proteins), advantageously permit improved patient compliance and convenience, more stable blood levels and potential dose reduction. The slow and constant release capabilities afforded thereby advantageously permit reduced dosages, due to more efficient delivery of active protein. Significant cost savings may be achieved by using the SPPs, spherical nanocrystalline composite particles, crystalline SPPs and compositions or formulations described herein.

The SPPs, spherical nanocrystalline composite particles or crystalline SPPs and compositions or formulations of the present invention enhance preservation of the native biologically active secondary or tertiary structure of the biologically active proteins. The biological activity and conformation of the protein component of the SPP, spherical nanocrystalline composite particle or crystalline SPP can be measured and compared with its native, soluble counterpart using a number of methods, including, inter alia:

1. Fourier Transform Infrared (FTIR) Spectroscopy to measure secondary structure:

FTIR Spectroscopy is a useful method for measuring the secondary structural characteristics of the protein component of an SPP, spherical nanocrystalline composite particle or crystalline SPP and comparing it with that of its native, soluble counterpart. More particularly, FTIR Spectroscopy can measure the α-helical or β-sheet content of a protein derived from an SPP, spherical nanocrystalline composite particle or crystalline SPP and compare it with the α-helical or β-sheet content of its native, soluble counterpart. See Example 13.

2. Fourier Transform Infrared (FTIR) Spectroscopy to measure tertiary structure:

FTIR Spectroscopy is also useful for measuring the tertiary structural characteristics of the protein component of an SPP, spherical nanocrystalline composite particle or crystalline SPP and comparing it with that of its native, soluble counterpart. See Example 46.

3. Circular Dichroism (CD) Spectroscopy:

CD Spectroscopy is a useful method for the rapid determination of a molecule's structural features. CD spectra allow characterization of the secondary structure of a protein, including, inter alia, the β-sheet content, the α-helical content, the β-turn content and the random coil content of a protein being assayed. CD spectra further allow characterization of the type of structure of a nucleic acid including, inter alia, whether the nucleic acid molecule is A-form (A-DNA or A-RNA), B-form (B-DNA) or Z-form (Z-DNA). In this way, the secondary structure of proteins or nucleic acids derived from dissolving SPPs, spherical nanocrystalline composite particles or crystalline SPPs or spherical nucleic acid particles, spherical nanocrystalline composite nucleic acid particles or crystalline spherical nucleic acid particles may be compared to their soluble counterparts. See Example 44.

4. ELISAs to measure specific binding of a monoclonal antibody to its antigen:

Enzyme-Linked Immunosorbent Assays may be used to compare the antigenic conformation of a protein derived from an SPP, spherical nanocrystalline composite particle or a crystalline SPP with that of its native, soluble counterpart, by using a monoclonal antibody which specifically binds the native, soluble counterpart. See Example 45.

5. Bioimmunoassays for the Determination of Biological Activity of Antibodies:

Alternatively, the biological activity of the protein component of antibody SPPs, antibody spherical nanocrystalline composite particles or antibody crystalline SPPs may be determined by bioimmunoassays. Bioimmunoassays are useful for measuring the biological activity of an antibody. Bioimmunoassays for measuring the biological activity of an antibody include, inter alia, direct cytotoxicity, complement dependent cytotoxicity (CDC), and antibody-dependent cell-mediated cytotoxicity (ADCC), described below. These assays are useful for comparing the residual biological activity of antibodies derived from antibody SPPs, antibody spherical nanocrystalline composite particles or antibody crystalline SPPs with that of their soluble antibody counterparts. In this way, the effects of making SPPs, spherical nanocrystalline composite particles or crystalline SPPs from antibodies, short- or long-term storage, drying, and forming and subsequently dissolving SPP, spherical nanocrystalline composite particle and crystalline SPP compositions or formulations, may be determined and compared to the soluble counterpart of the antibody in question.

The cytotoxicity of an antibody on its antigen bearing target cells can be characterized by three assays, e.g. direct cytotoxicity, complement dependent cytotoxicity (CDC), and antibody-dependent cell-mediated cytotoxicity (ADCC). The target cells for Rituxan are the cells that overexpress CD-20 antigen on their surface, which include Raji, Daudi, JOKI and WT100. The specific antigen for Herceptin is HER2 (human epidermal growth factor receptor 2 protein), which is overexpressed in human breast adenocarcinoma cell lines including SK-BR-3, BT474, and MCF/HER2.

The SPPs, spherical nanocrystalline composite particles or crystalline SPPs and compositions and formulations thereof of the present invention create a reservoir which can slowly release active protein to a subject where and when they are needed. The biologically active protein is subsequently released in a controlled manner over a period of time, as determined by the particular encapsulation technique, polymer formulation, SPP, spherical nanocrystalline composite particle or crystalline SPP size, SPP, spherical nanocrystalline composite particle or crystalline SPP solubility, and the presence and nature of any excipients used. The SPPs, spherical nanocrystalline composite particles or crystalline SPPs and compositions and formulations thereof of this invention may be reconstituted with a diluent for the parenteral administration of biologically active proteins.

One embodiment of a composition according to this invention is a formulation. Formulations comprising SPPs, spherical nanocrystalline composite particles or crystalline SPPs of biologically active proteins in polymeric delivery carriers according to this invention may also comprise any conventional carrier or adjuvant used in vaccines, pharmaceuticals, personal care formulations or compositions, veterinary formulations or compositions, or oral enzyme supplementation. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

According to one embodiment of this invention, SPPs, spherical nanocrystalline composite particles or crystalline SPPs of biologically active proteins, including intact antibodies or single chain Fv antibody fragments, may be combined with any conventional materials used for controlled release administration, including pharmaceutical controlled release administration and carrier-free pharmaceutical controlled release administration. Such materials include, for example, coatings, shells and films, such as enteric coatings and polymer coatings and films.

Compositions, including formulations, comprising SPPs, spherical nanocrystalline composite particles or crystalline SPPs, may be delivered to humans, animals, or plants at the desired site of delivery according to this invention. Such delivery may include parenteral administration, including, e.g., subcutaneous, intravenous, or intramuscular injection, or the use of devices, such as implant-capable devices, or may involve other delivery systems, e.g., oral, pulmonary inhalation, transdermal, needleless injection and needleless subcutaneous administration.

In one embodiment of this invention, SPPs, spherical nanocrystalline composite particles or crystalline SPPs of a biologically active protein have a diameter between about 0.04 μm and about 300 μm. In another embodiment of this invention, SPPs, spherical nanocrystalline composite particles or crystalline SPPs of a biologically active protein have a diameter between about 0.04 µm and about 200 µm. In another embodiment of this invention, SPPs, spherical nanocrystalline composite particles or crystalline SPPs of a biologically active protein have a diameter between about 0.04 µm and about 100 µm. In another embodiment of this invention, SPPs, spherical nanocrystalline composite particles or crystalline SPPs of a biologically active protein have a diameter between about 0.04 µm and about 10 µm. In a most preferred embodiment of this invention, SPPs, spherical nanocrystalline composite particles or crystalline SPPs of a biologically active protein have a diameter between about 0.04 µm and about 5 µm. In another embodiment of this invention, SPPs, spherical nanocrystalline composite particles or crystalline SPPs of a biologically active protein have a diameter between about 0.04 µm and about 1 µm. In another embodiment of this invention, SPPs, spherical nanocrystalline composite particles or crystalline SPPs of a biologically active protein have a diameter between about 0.04 µm and about 999 nm. In another embodiment of this invention, SPPs, spherical nanocrystalline composite particles or crystalline SPPs of a biologically active protein have a diameter between about 0.04 µm and about 499 nm.

In a preferred embodiment of the spherical nanocrystalline composite particles according to this invention, the particles are from about 1 µm to about 300 µm in diameter, and comprise protein nanocrystals having a diameter between about 40 nm and about 999 nm. A most preferred embodiment of the spherical nanocrystalline composite particles according to this invention is that the spherical nanocrystalline composite particles are from about 1 µm to about 300 µm in diameter, and comprise protein nanocrystals having a diameter between about 40 nm and about 499 nm.

In one embodiment of this invention compositions, including formulations, comprising SPPs, spherical nanocrystalline composite particles or crystalline SPPs have a protein concentration in solution greater than about 1 mg/ml. Alternatively, compositions, including formulations, of the present invention have protein concentration in solution greater than about 10 mg/ml. Alternatively, compositions, including formulations, of the present invention have a protein concentration in solution greater than about 20 mg/ml. Alternatively, compositions, including formulations, of the present invention have a protein concentration in solution greater than about 50 mg/ml. Alternatively, compositions, including formulations, of the present invention have a protein concentration in solution greater than about 100 mg/ml. Alternatively, compositions, including formulations, of the present invention have a protein concentration in solution greater than about 120 mg/ml. Alternatively, compositions, including formulations, of the present invention have a protein concentration in solution greater than about 200 mg/ml. Alternatively, compositions, including formulations, of the present invention have a protein concentration in solution greater than about 400 mg/ml.

According to this invention, any individual, including humans, animals and plants, may be treated in a pharmaceutically acceptable manner with a pharmaceutically effective amount of SPPs, spherical nanocrystalline composite particles or crystalline SPPs of a biologically active protein, or compositions or formulations comprising such SPPs, spherical nanocrystalline composite particles or crystalline SPPs, for a period of time sufficient to treat a condition in the individual to whom they are administered over some period of time. Alternatively, individuals may receive a prophylactically effective amount of biologically active SPPs, spherical nanocrystalline composite particles or crystalline SPPs, or compositions or formulations comprising such SPPs, spherical nanocrystalline composite particles or crystalline SPPs which is effective to prevent a condition in the individual to whom they are administered over some period of time.

SPPs, spherical nanocrystalline composite particles or crystalline SPPs of biologically active proteins, or compositions or formulations comprising them, may be administered alone, as part of a pharmaceutical, personal care or veterinary preparation, or as part of a prophylactic preparation, with or without adjuvant. They may be administered by parenteral or oral routes. For example, they may be administered by oral, pulmonary, nasal, aural, anal, dermal and transdermal, ocular, intravenous, intramuscular, intraarterial, intraperitoneal, mucosal, sublingual, subcutaneous, transdermally, or intracranial route. In either pharmaceutical, personal care or veterinary applications, SPPs, spherical nanocrystalline composite particles or crystalline SPPs, or compositions or formulations thereof, may be topically administered to any epithelial surface. Such epithelial surfaces include oral, ocular, aural, anal and nasal surfaces, which may be treated, protected, repaired or detoxified by application of SPPs, spherical nanocrystalline composite particles or crystalline SPPs of biologically active proteins, or compositions or formulations thereof.

Pharmaceutical, veterinary or prophylactic compositions or formulations comprising SPPs, spherical nanocrystalline composite particles or crystalline SPPs of biologically active proteins or compositions or formulations comprising them may also be selected from the group consisting of tablets, liposomes, granules, spheres, microparticles, microspheres, aerosols and capsules.

For such uses, as well as other uses according to this invention, SPPs, spherical nanocrystalline composite particles or crystalline SPPs of biologically active proteins, or compositions or formulations comprising them, may be formulated into tablets. Such tablets constitute a liquid-free, dust-free form for storage of SPPs, spherical nanocrystalline composite particles or crystalline SPPs of biologically active proteins, or compositions or formulations comprising them, which are easily handled and retain acceptable levels of activity or potency.

Alternatively, SPPs, spherical nanocrystalline composite particles or crystalline SPPs of biologically active proteins, or compositions or formulations comprising them, may be in a variety of conventional forms employed for administration to provide reactive compositions or formulations. These include, for example, solid, semi-solid and liquid dosage forms, such as liquid solutions or suspensions, slurries, gels, creams, balms, emulsions, lotions, powders, sprays, foams, pastes, ointments, salves, balms and drops.

SPPs, spherical nanocrystalline composite particles or crystalline SPPs of biologically active proteins, or compositions or formulations comprising them, may also comprise any conventional carrier or adjuvant used in pharmaceuticals, personal care compositions or formulations or veterinary compositions or formulations. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

The most effective mode of administration and dosage regimen of SPPs, spherical nanocrystalline composite particles or crystalline SPPs of biologically active proteins, or compositions or formulations comprising them, will depend on the effect desired, the outcome of SPP, spherical nanocrystalline composite particles or crystalline SPP administration, previous therapy, if any, the individual's health status or status of the condition itself and response to the SPPs, spherical nanocrystalline composite particles or crystalline SPPs of biologically active proteins or compositions or formulations comprising them and the judgment of the treating physician or clinician. The SPPs, spherical nanocrystalline composite particles or crystalline SPPs or compositions or formulations comprising them may be administered in any dosage form acceptable for pharmaceuticals, immunotherapy, or veterinary compositions or formulations, at one time or over a series of treatments.

The amount of SPPs, spherical nanocrystalline composite particles or crystalline SPPs of biologically active proteins, or compositions or formulations comprising them, which provides a single dosage will vary depending upon the particular mode of administration, the particular type of SPP, spherical nanocrystalline composite particle or crystalline SPP or composition or formulation thereof, and the dose level or dose frequency. A typical preparation will contain between about 0.01% and about 99%, preferably between about 1% and about 50%, SPPs, spherical nanocrystalline composite particles or crystalline SPPs of biologically active proteins (w/w). Alternatively, a preparation will contain between about 0.01% and about 80% SPPs, spherical nanocrystalline composite particles or crystalline SPPs, preferably between about 1% and about 50%, SPPs, spherical nanocrystalline composite particles or crystalline SPPs of biologically active proteins (w/w).

Upon improvement of the individual's condition, a maintenance dose of SPPs, spherical nanocrystalline composite particles or crystalline SPPs of biologically active proteins, or compositions or formulation comprising them, may be administered, if necessary. Subsequently, the dosage or frequency of administration, or both, may be reduced as a function of the symptoms, to a level at which the improved condition is retained. When the condition has been alleviated to the desired level, treatment should cease. Individuals may, however, require intermittent treatment on a long-term basis upon any recurrence of the condition or symptoms thereof.

The present invention may also utilize other slow release methodologies, such as silicon based rings or rods which have been preloaded with SPPs, spherical nanocrystalline composite particles or crystalline SPPs or compositions or formulations comprising them, and which can therefore act as implants for delivery. The purpose of this technique is to provide a constant level of protein to the bloodstream over a period of weeks or months. Such implants can be inserted intradermally and can be safely removed and replaced when needed.

Other compositions or formulations according to this invention include vaccine compositions or formulations comprising SPPs, spherical nanocrystalline composite particles or crystalline SPPs of antigenic proteins, adjuvant, and, optionally, encapsulating polymer(s). In one embodiment of this invention, an intact anti-idiotypic antibody is itself the immunogen, and thus the goal is that the intact antibody SPPs, spherical nanocrystalline composite particles or crystalline SPPs, or compositions or formulations comprising them, would elicit a response to the antigen that the anti-idiotype mimics or is closely related to. Therefore, the anti-idiotypic antibody can act as a type of vaccine or therapy against cancers and autoimmune diseases, e.g., allergies, as well as viruses like hepatitis B virus.

One embodiment of such compositions or formulations involves a single vaccine injection containing microspheres having three or more different release profiles. In this way, SPPs, spherical nanocrystalline composite particles or crystalline SPPs of protein antigens, or anti-idiotypic antibodies that act like antigens, may be released over a sustained period sufficient to generate lasting immunity. By virtue of this composition or formulation, multiple antigen boosts may be possible in single unit form. One advantage of such a system is that by using SPPs, spherical nanocrystalline composite particles or crystalline SPPs of antigenic proteins, or anti-idiotypic antibodies that act like antigens, the native three-dimensional structures of the antigens are maintained and presented to the immune system in their native form.

Once the immune system is primed, there may be less need for an adjuvant effect. Therefore, in the slower degrading inoculations, a less immunogenic adjuvant may be included and possibly no adjuvant may be required in the slowest degrading microspheres of compositions or formulations. In this way, patient populations in remote areas need not have to be treated multiple times in order to provide protection against infectious diseases. One of skill in the art of biological delivery of protein antigens, or anti-idiotypic antibodies that act like antigens, will appreciate that many variations on this theme are feasible.

Another advantage of the present invention is that SPPs, spherical nanocrystalline composite particles or crystalline SPPs of biologically active proteins, or compositions or formulations comprising them, can be dried by lyophilization (see Example 26, Method 3). Lyophilization, or freeze-drying allows water to be separated from the composition or formulation. The SPPs, spherical nanocrystalline composite particles or crystalline SPPs, or compositions or formulations comprising them, are first frozen and then placed in a high vacuum. In a vacuum, the crystalline $H_2O$ sublimes, leaving behind the intact SPP, spherical nanocrystalline composite particle or crystalline SPP, or composition or formulation thereof, containing only the tightly bound water. Such processing further stabilizes the SPP, spherical nanocrystalline composite particle or crystalline SPP, or composition or formulation thereof, and allows for easier storage and transportation at typically encountered ambient temperatures.

The SPPs, spherical nanocrystalline composite particles or crystalline SPPs of this invention may also be spray-dried (see Example 26, Method 6). Spray drying allows water to be separated from the SPP, spherical nanocrystalline composite particle or crystalline SPP, or composition or formulation thereof. It is highly suited for the continuous production of dry solids in either powder, granulate or agglomerate form from liquid feedstocks as solutions, emulsions, and pumpable suspensions. Spray drying involves the atomization of a liquid feedstock into a spray of droplets and contacting the droplets with hot air in a drying chamber. The sprays are produced by either rotary (wheel) or by nozzle atomizers. Evaporation of moisture from the droplets and formation of dry particles proceed under controlled temperature and airflow conditions. Relatively high temperatures are needed for spray drying operations. However, heat damage to products is generally only slight, because of an evaporative cooling effect during the critical drying period and because the subsequent time of exposure to high temperatures of the dry material may be vary short. Powder is discharged continuously from the drying chamber. Operating conditions and dryer design are selected according to the drying characteristics of the product and the powder specification. Spray drying is an ideal process where the end product must comply with precise quality standards regarding particle size distribution, residual moisture content, bulk density and particle shape.

This feature is especially desirable for therapeutic proteins and protein vaccines, including anti-idiotypic antibodies, which can be dispensed into single dose sterile containers ("ampules") or alternatively, any desired increment of a single dose as a slurry, in a composition or formulation. The ampules containing the dispensed slurries or compositions or formulations can then be capped, batch frozen and lyophilized under sterile conditions. Such sterile containers can be transported throughout the world and stored at ambient temperatures. Such a system is useful for providing sterile vaccines and therapeutic proteins to remote and undeveloped parts of the world. At the point of use, the ampule is rehydrated with the sterile solvent or buffer of choice and dispensed. For such preparations, minimal or no refrigeration is required.

The SPPs, spherical nanocrystalline composite particles or crystalline SPPs of this invention may also be nitrogen-dried (see Example 26, Method 1), air-dried (see Example 26, Method 5), air-dried after addition of organic solvents (see Example 26, Method 4), or vacuum oven-dried (see Example 26, Method 2).

In another embodiment of this invention, SPPs, spherical nanocrystalline composite particles or crystalline SPPs of biologically active proteins according to this invention may be crosslinked for additional stability. This allows for the use of such SPPs, spherical nanocrystalline composite particles or crystalline SPPs, or compositions or formulations comprising them, in areas of pH extremes, such as the gastrointestinal tract of humans and animals. For example, SPPs, spherical nanocrystalline composite particles or crystalline SPPs of biologically active proteins or vaccines, e.g., monoclonal antibody or anti-idiotypic antibody SPPs, spherical nanocrystalline composite particles or crystalline SPPs, may be crosslinked using one of a variety of crosslinkers, including, but not limited to, Dimethyl 3,3'-dithiobispropionimidate-.HCl (DTBP), Dithiobis (succinimidylpropionate) (DSP), Bis maleimido-hexane (BMH), Bis[Sulfosuccinimidyl]suberate (BS), 1,5-Difluoro-2,4-dinitrobenzene (DFDNB), Dimethylsuberimidate.2 HCl (DMS), Disuccinimidyl glutarate (DSG), Disulfosuccinimidyl tartarate (Sulfo-DST), 1-Ethyl-3-[3-Dimethylaminopropyl]carbodiimide hydrochloride (EDC), Ethylene glycolbis[sulfosuccinimidylsuccinate] (Sulfo-EGS), N-[g-maleimidobutyryloxy]succinimide ester (GMBS), N-hydroxysulfosuccinimidyl-4-azidobenzoate (Sulfo-HSAB), Sulfosuccinimidyl-6-[a-methyl-a-(2-pyridyldithio)toluamido]hexanoate (Sulfo-LC-SMPT), Bis-[b-(4-azidosalicylamido)ethyl]disulfide (BASED) and glutaraldehyde (GA).

In a further embodiment of this invention, SPPs, spherical nanocrystalline composite particles or crystalline SPPs of a protein, such as an intact antibody or scFv fragment of an antibody, may be radiolabelled to be used in antibody radiation therapies. In such a therapy, for example, an SPP, spherical nanocrystalline composite particle or crystalline SPP containing a radiolabelled anti-cancer antibody or scFv fragment, or a composition or formulations comprising them, can be delivered according to this invention, to the site of the cancer. After delivery, the released antibody or scFv fragment binds to its targeted cancer antigen and delivers the radioisotope directly to the cancerous cells or tumor. The release of the antibody may be timed according to this invention. Theoretically, useful radiolabels include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$. Practically, however, in vivo use in radiotherapies would limit the radiolabel to $^{131}I$, $^{90}Y$, or any other radiolabels defined by a short half-life. For example, the monoclonal antibody Rituximab has been labelled with $^{90}Yttrium$ ($^{90}Y$), in order to be used for radioimmunotherapy in patients with non-Hodgkin's lymphomas. This compound is commercially available as Zevalin™ (IDEC Pharmaceuticals, (San Diego, Calif.)).

Encapsulation of SPPs, Spherical Nanocrystalline Composite Particles or Crystalline SPPs of Biologically Active Proteins in Polymeric Carriers:

According to one embodiment of this invention, formulations are produced when SPPs, spherical nanocrystalline composite particles or crystalline SPPs of biologically active proteins are encapsulated in at least one polymeric carrier to form microspheres by virtue of encapsulation within the matrix of the polymeric carrier to preserve their native and biologically active tertiary structure. The SPPs, spherical nanocrystalline composite particles or crystalline SPPs can be encapsulated using various biocompatible and/or biodegradable polymers having unique properties which are suitable for delivery to different biological environments or for effecting specific functions. The rate of dissolution and, therefore, delivery of active protein, is determined by the particular encapsulation technique, polymer composition, polymer crosslinking, polymer thickness, polymer solubility, and antibody crystal geometry.

SPPs, spherical nanocrystalline composite particles or crystalline SPPs of biologically active proteins to be encapsulated are suspended in a polymeric carrier which is dissolved in an organic solvent. The polymer solution must be concentrated enough to completely coat the SPPs, spherical nanocrystalline composite particles or crystalline SPPs after they are added to the solution. Such an amount is one which provides a weight ratio of SPPs, spherical nanocrystalline composite particles or crystalline SPPs to polymer between about 0.02 and about 20, preferably between about 0.1 and about 2. The SPPs, spherical nanocrystalline composite particles or crystalline SPPs are contacted with polymer in solution for a period of time between about 0.5 minutes and about 30 minutes, preferably between about 1 minutes and about 3 minutes. The SPPs, spherical nanocrystalline composite particles or crystalline SPPs should be kept suspended and not allowed to aggregate as they are coated by contact with the polymer.

Following that contact, the SPPs, spherical nanocrystalline composite particles or crystalline SPPs become coated and are referred to as nascent microspheres. The nascent microspheres increase in size while coating occurs. In a preferred embodiment of the invention, the suspended coated SPPs, spherical nanocrystalline composite particles or crystalline SPPs or nascent microspheres, along with the polymeric carrier and organic solvent, are transferred to a larger volume of an aqueous solution containing a surface active agent, known as an emulsifier. In the aqueous solution, the suspended nascent microspheres are immersed in the aqueous phase, where the organic solvent evaporates or diffuses away from the polymer. Eventually, a point is reached where the polymer is no longer soluble and forms a precipitated phase encapsulating the SPPs, spherical nanocrystalline composite particles or crystalline SPPs to form a formulation. This aspect of the process is referred to as hardening of the polymeric carrier or polymer. The emulsifier helps to reduce the interfacial surface tension between the various phases of matter in the system during the hardening phase of the process. Alternatively, if the coating polymer has some inherent surface activity, there may be no need for addition of a separate surface active agent.

Emulsifiers useful to prepare encapsulated SPPs, spherical nanocrystalline composite particles or crystalline SPPs of biologically active proteins according to this invention include poly(vinyl alcohol) as exemplified herein, surfactants and other surface active agents which can reduce the surface tension between the polymer coated SPPs, spherical nanocrystalline composite particles or crystalline SPPs and the solution.

In a preferred embodiment of this invention, crystallinity of the spherical nanocrystalline composite particles or crystalline SPPs is maintained during the encapsulation process. The crystallinity is maintained during the coating process by using an organic solvent in which the spherical nanocrystalline composite particles or crystalline SPPs are not soluble. Subsequently, once the coated spherical nanocrystalline composite particles or crystalline SPPs are transferred to the aqueous solvent, rapid hardening of the polymeric carrier and sufficient coating of the spherical nanocrystalline composite particles or crystalline SPPs in the previous step shields the crystalline material from dissolution.

The polymers used as polymeric carriers to coat the SPPs, spherical nanocrystalline composite particles or crystalline SPPs can be either homo-polymers or co-polymers. The rate of hydrolysis of the microspheres is largely determined by the hydrolysis rate of the individual polymer species. In general, the rate of hydrolysis decreases as follows: polycarbonates>polyesters>polyurethanes>polyorthoesters>polyamides. For a review of biodegradable and biocompatible polymers, see W. R. Gombotz and D. K. Pettit, "Biodegradable polymers for protein and peptide drug delivery", Bioconjugate Chemistry, vol. 6, pp. 332-351 (1995).

In a preferred embodiment of this invention, the polymeric carrier comprises a single polymer type such as PLGA. In a next preferred embodiment, the polymeric carrier can be a mixture of polymers, such as 50% PLGA and 50% albumin.

Other polymers useful as polymeric carriers to prepare encapsulated SPPs, spherical nanocrystalline composite particles or crystalline SPPs of biologically active proteins according to this invention include biocompatible/biodegradable polymers selected from the group consisting of poly (acrylic acid), poly (cyanoacrylates), poly (amino acids), poly (anhydrides), poly (depsipeptide), poly (esters), such as poly (lactic acid) or PLA, poly (b-hydroxybutryate), poly (caprolactone) and poly (dioxanone); poly (ethylene glycol), poly (hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, starch and its derivatives, collagen, fibrin, gelatin, hyaluronic acid, oligosaccharides, glycaminoglycans, sulfated polysaccharides, blends and copolymers thereof. Other useful polymers are described in J. Heller and R. W. Balar, "Theory and Practice of Controlled Drug Delivery from Biodegradable Polymers," Academic Press, New York, N.Y., (1980); K. O. R. Lehmann, H. M. Bossler and D. K. Dreher, Biol. Macromol. Monog. vol. 5, pp. 111-19 (1979); E. M. Ramadan, A. El-Helw and Y. El-Said, Journal of Microencapsulation, vol. 5, p. 125 (1988). The preferred polymer will depend upon the particular protein component of the SPPs, spherical nanocrystalline composite particles or crystalline SPPs used and the intended use of the encapsulated SPPs, spherical nanocrystalline composite particles or crystalline SPPs. Alternatively, the solvent evaporation technique may be used for encapsulating SPPs, spherical nanocrystalline composite particles or crystalline SPPs (see D. Babay, A. Hoffmann and S. Benita, Biomaterials vol. 9, pp. 482-488 (1988).

In a preferred embodiment of this invention, SPPs, spherical nanocrystalline composite particles or crystalline SPPs of biologically active proteins are encapsulated in at least one polymeric carrier using a double emulsion method, as illustrated herein, using a polymer, such as polylactic-co-glycolyic acid. In a most preferred embodiment of this invention, the polymer is Polylactic-co-glycolyic acid ("PLGA"). PLGA is a co-polymer prepared by polycondensation reactions with lactic acid ("L") and glycolic acid ("G"). Various ratios of L and G can be used to modulate the crystallinity and hydrophobicity of the PLGA polymer. Higher crystallinity of the polymer results in slower dissolution. PLGA polymers with 20-70% G content tend to be amorphous solids, while high levels of either G or L result in good polymer crystallinity. See D. K. Gilding and A. M. Reed, "Biodegradable polymers for use in surgery-poly(glycolic)/poly(lactic acid) homo and copolymers: 1., *Polymer* vol. 20, pp. 1459-1464 (1981). PLGA degrades after exposure to water by hydrolysis of the ester bond linkage to yield non-toxic monomers of lactic acid and glycolic acid.

Another embodiment of this invention includes double-walled polymer coated microspheres. Double-walled polymer coated microspheres may be produced by preparing two separate polymer solutions in methylene chloride or other solvent which can dissolve the polymers. The SPPs, spherical nanocrystalline composite particles or crystalline SPPs of biologically active proteins are added to one of the solutions and dispersed. Here, the SPPs, spherical nanocrystalline composite particles or crystalline SPPs become coated with the first polymer. Then, the solution containing the first polymer coated SPPs, spherical nanocrystalline composite particles or crystalline SPPs is combined with the second polymer solution. [See Pekarek, K. J.; Jacob, J. S. and Mathiowitz, E. Double-walled polymer microspheres for controlled drug release, Nature, 367, 258-260 (Jan. 20, 1994)]. As a result, the second polymer encapsulates the first polymer which is encapsulating the crystal. Ideally, this solution is then dripped into a larger volume of an aqueous solution containing a surface active agent or emulsifier. In the aqueous solution, the solvent evaporates from the two polymer solutions and the polymers are precipitated.

Compositions according to this invention comprise SPPs, spherical nanocrystalline composite particles or crystalline SPPs of biologically active proteins and at least one ingredient. Formulations according to this invention are compositions wherein at least one of the ingredients added to an SPP, spherical nanocrystalline composite particle or crystalline SPP is a polymer.

SPPs, spherical nanocrystalline composite particles or crystalline SPPs of biologically active proteins according to this invention may be characterized for secondary structure. More particularly, such SPPs, spherical nanocrystalline composite particles or crystalline SPPs of biologically active proteins may be characterized by β-sheet or α-helical structural content, as indicated by a correlation spectra as compared to the spectra of the soluble protein counterpart determined by Fourier transform infrared (FTIR) spectra that is between about 0.8 and 1.0. A correlation coefficient of less than about 0.8 indicates an protein sample that has become denatured to such en extent that its secondary structural content has changed, relative to the native, biologically active protein, by more than about 20%. This may result in protein aggregation and precipitation, or merely a loss of biological activity.

A correlation coefficient that is between about 0.8 and 1.0 indicates that the protein sample has a secondary structural content that is about 80% to about 100% identical with that of its native, soluble counterpart.

SPPs, spherical nanocrystalline composite particles or crystalline SPPs, or compositions or formulations comprising them, may be characterized by the loss of less than 20% α-helical structural content of the protein after storage for from about 4 days to about 180 days at from about 4° C. to about 50° C., wherein the soluble form of said protein loses more than 50% of its α-helical structural content after storage for 6 hours at 50° C., as measured by FTIR. Alternatively, they are characterized by the loss of less than 20% α-helical structural content of the protein after storage for 4 days at 50° C., wherein the soluble form of said protein loses more than 50% of its α-helical structural content after storage for 6 hours at 50° C., as measured by FTIR.

Alternatively, SPPs, spherical nanocrystalline composite particles and crystalline SPPs, and compositions or formulations comprising them, may be characterized by at least a 120-fold greater shelf life when stored at 50° C. than the soluble form of said protein in solution at 50° C., as measured by $T_{1/2}$. SPPs, spherical nanocrystalline composite particles and crystalline SPPs, and compositions or formulations comprising them, may alternatively be characterized by at least a 60-fold greater shelf life when stored at 50° C. than the soluble form of said protein in solution at 50° C., as measured by $T_{1/2}$. Alternatively, SPPs, spherical nanocrystalline composite particles and crystalline SPPs, and compositions or formulations comprising them, may be characterized by at least a 30-fold greater shelf life when stored at 50° C. than the soluble form of said protein in solution at 50° C., as measured by $T_{1/2}$. SPPs, spherical nanocrystalline composite particles and crystalline SPPs, and compositions or formulations comprising them, may alternatively be characterized by at least a 10-fold greater shelf life when stored at 50° C. than the soluble form of said protein in solution at 50° C., as measured by $T_{1/2}$. Alternatively, SPPs, spherical nanocrystalline composite particles and crystalline SPPs, and compositions or formulations comprising them, may be characterized by a greater shelf life when stored at 50° C. than the soluble form of said protein in solution at 50° C., as measured by $T_{1/2}$.

Alternatively, the biological activity of SPPs, crystalline SPPs or spherical nanocrystalline composite particles comprising an antibody may be determined by bioimmunoassays. Bioimmunoassays for measuring the biological activity of an antibody include, inter alia, direct cytotoxicity, complement dependent cytotoxicity (CDC), and antibody-dependent cell-mediated cytotoxicity (ADCC), described below. These assays are useful for comparing the residual biological activity of antibodies derived from antibody SPPs, spherical nanocrystalline composite particles or crystalline antibody SPPs with their soluble antibody counterparts. In this way, the effects of making SPPs, spherical nanocrystalline composite particles or crystalline SPPs from antibodies, short- or long-term storage, drying, and forming and subsequently dissolving SPP, spherical nanocrystalline composite particle and crystalline SPP compositions or formulations, may be determined and compared to the soluble counterpart of the antibody in question.

The cytotoxicity of an antibody on its antigen bearing target cells can be characterized by three assays, e.g. direct cytotoxicity, complement dependent cytotoxicity (CDC), and antibody-dependent cell-mediated cytotoxicity (ADCC). The target cells for Rituxan are the cells that overexpress CD-20 antigen on their surface, which include Raji, Daudi, JOK1 and WT100. The specific antigen for Herceptin is HER2 (human epidermal growth factor receptor 2 protein), which is overexpressed in human breast adenocarcinoma cell lines including SK-BR-3, BT474, and MCF/HER2.

Preferably, the protein antibody component derived from dissolving SPPs, crystalline SPPs or spherical nanocrystalline composite particles comprising an antibody, will have about 50% of the biological activity of its soluble antibody counterpart. More preferably, the protein antibody component derived from dissolving SPPs, crystalline SPPs or spherical nanocrystalline composite particles comprising an antibody, will have about 60% of the biological activity of its soluble antibody counterpart. More preferably, the protein antibody component derived from dissolving SPPs, crystalline SPPs or spherical nanocrystalline composite particles comprising an antibody, will have about 70% of the biological activity of its soluble antibody counterpart. More preferably, the protein antibody component derived from dissolving SPPs, crystalline SPPs or spherical nanocrystalline composite particles comprising an antibody, will have about 80% of the biological activity of its soluble antibody counterpart. More preferably, the protein antibody component derived from dissolving SPPs, crystalline SPPs or spherical nanocrystalline composite particles comprising an antibody, will have about 90% of the biological activity of its soluble antibody counterpart. Most preferably, the protein antibody component derived from dissolving SPPs, crystalline SPPs or spherical nanocrystalline composite particles comprising an antibody, will have about 100% of the biological activity of its soluble antibody counterpart.

Spherical Nucleic Acid Particles

In another embodiment of this invention, the methods disclosed herein are useful for forming spherical particles of nucleic acids, i.e., spherical nucleic acid particles ("SNAPs"). SNAPs may be useful as vaccine antigens for the development of DNA vaccines. SNAPs may also be useful for the delivery of genes in gene therapy strategies.

Stability of Encapsulated SPPs, Spherical Nanocrystalline Composite Particles or Crystalline SPPs of Biologically Active Proteins Those of skill in the art will appreciate that protein stability is one of the most important obstacles to successful formulation of polymer microparticulate delivery systems that control the release of proteins. Protein stability of SPPs, spherical nanocrystalline composite particles or crystalline SPPs of biologically active proteins encapsulated in polymeric carriers may be challenged at three separate stages: manufacture of the SPP, spherical nanocrystalline composite particle or crystalline SPP compositions or formulations, protein release from the resulting SPP, spherical nanocrystalline composite particle or crystalline SPP compositions or formulations, and in vivo stability after the protein release. During preparation of microparticles or microspheres containing soluble or amorphous proteins, the use of organic solvents and lyophilization are especially detrimental to protein stability. Subsequently, released proteins are susceptible to moisture-induced aggregation, thus resulting in permanent inactivation.

In order to achieve high protein stability during preparation of SPPs, spherical nanocrystalline composite particles or crystalline SPP compositions or formulations according to the present invention, it is necessary to restrict the mobility of individual biologically active protein molecules—a result achievable through the use of SPPs, spherical nanocrystalline composite particles or crystalline SPPs.

Maintaining the Morphology Crystallinity and Stability of SPPs Spherical Nanocrystalline Composite Particles or Crystalline SPPs when Making Formulations:

In order to use SPPs, spherical nanocrystalline composite particles or crystalline SPPs as the protein source for preparing protein formulations according to the present invention, the problem of SPP, spherical nanocrystalline composite particle or crystalline SPP dissolution outside the mother liquor used during the dialysis procedure had to be overcome. In order to maintain the morphology and/or crystallinity and/or stability of the SPPs, spherical nanocrystalline composite particles or crystalline SPPs used in the production of formulations, several approaches may be used:

1. Many compounds used in SPP, spherical nanocrystalline composite particle or crystalline SPP production according to this invention are compatible with polymer processing conditions, and may therefore be included when making formulations of SPPs, spherical nanocrystalline composite particles or crystalline SPPs. These include, inter alia, salts, organic solvents, metals and PEG.
2. Dried SPPs, spherical nanocrystalline composite particles or crystalline SPPs: The preparative buffer(s) (i.e., mother liquor) can be removed by filtration and the remaining "paste" can be dried by air, under vacuum, by washing with water-miscible organic solvents and/or by lyophilization or spray drying.
3. The SPP, spherical nanocrystalline composite particle or crystalline SPP size can be manipulated and controlled in the course of preparing formulations of SPPs, spherical nanocrystalline composite particles or crystalline SPPs. Thus, a range of sizes are available, each conferring different dissolution kinetics and subsequently different sustained release profiles when the SPP, spherical nanocrystalline composite particle or crystalline SPP formulations are used to deliver proteins to a subject.

Removal of Antibody Aggregates During Formation of Antibody SPPs, Spherical Nanocrystalline Composite Antibody Particles or Crystalline Antibody SPPs:

Aggregation is a serious problem often encountered with antibody preparations and can cause adverse effects in patients who receive such antibody preparations. In another embodiment of this invention, the process of formation of antibody SPPs, spherical nanocrystalline composite antibody particles or crystalline antibody SPPs removes antibody aggregates that may form during antibody preparation. (see Example 13).

EXAMPLES

In order that this invention may be better understood, the following examples are set forth. These examples are for the purpose of illustration only and are not to be construed as limiting the scope of the invention in any manner.

Example 1

Preparation of Spherical Protein Particles of Infliximab

Infliximab is a chimeric murine/human monoclonal antibody commercially available as Remicade™ (Centocor, Leiden, the Netherlands). This monoclonal antibody has been widely used to treat rheumatoid arthritis and Crohn's disease. Infliximab is a chimeric IgG1 kappa immunoglobulin that binds to the TNFα antigen. It is composed of murine light- and heavy-chain variable region sequences and a human constant region sequence. The Infliximab antibody has an approximate molecular weight (MWt) of 149 kD.

Infliximab SPP Preparation

Materials:

Infliximab antibody (each vial contains 100 mg Infliximab, 500 mg sucrose, 0.5 mg polysorbate 80, 2.2 mg monobasic sodium phosphate and 6.1 mg dibasic sodium phosphate) reconstituted in 10 ml water, pH approximately 7.2 (concentration equal to 10 mg/ml).

Procedure:

Infliximab SPPs were formed using a Slide-A-Lyzer (Pierce Chemicals, Catalog #69570), which was used as follows:

Dialysis Using a Slide-A-Lyzer:

A. The Slide-A-Lyzer used herein had a molecular weight cut-off point at 10 kD.

B. Procedure:
 1. Slide-A-Lyzer membrane units were soaked in distilled water overnight.
 2. The lower part of a small Centricon tube (Amicon, Catalog #4208) was filled with 3.8-3.9 ml of an appropriate buffer (for Infliximab, see below).
 3. A 3.5 mm×3.5 mm magnetic stirring bar was used to stir the solution in the lower part of the Centricon device.
 4. 150-410 µl of the desired protein solution (for this example, Infliximab), at a protein concentration approximately equal to 10-20 mg/ml, was added to the Slide-A-Lyzer apparatus. The appropriate membrane unit was placed in the Slide-A-Lyzer apparatus such that it was a millimeter or two below the level of the buffer solution, and the cap was placed on the Slide-A-Lyzer unit, tight enough so as to prevent evaporation.
 5. The buffer/protein mixture was then dialyzed for the appropriate time at the appropriate temperature.
 6. After dialysis, the presence or absence of SPPs was determined using HPLC and microscopy, the protein content of the supernatant was determined by measuring absorbance at an Optical Density of 280 nm ($OD_{280}$). SPPs were harvested at the appropriate time.

Formation of Infliximab SPPs:

150 µl of a 10 mg/ml solution of Infliximab was dialyzed against 3.9 ml of a solution consisting of 2.1 M ammonium sulfate, 0.1 M sodium acetate, pH 5.8, 1% propylene glycol. A 10,000 MW cut-off dialysis membrane (in a Slide-A-Lyzer) was used. The mixture was dialyzed at room temperature for 28 hours. Then the protein solution was washed twice in 800 µl of a solution consisting of 2.42 M ammonium sulfate, 1% propylene glycol, 0.1 M sodium acetate pH 5.8, centrifuged, and resuspended in approximately 200 µl of the same solution.

Results:

Infliximab SPPs formed after 28 hours. See FIG. 1A.

Example 2

Preparation of Spherical Protein Particles of Rituximab

Rituximab is a chimeric murine/human monoclonal antibody commercially available as Rituxan™ (Genentech, Inc., South San Francisco, Calif.). This monoclonal antibody has been widely used to treat non-Hodgkins lymphoma. Rituximab is a chimeric IgG1 kappa immunoglobulin that binds to the CD20 antigen on the surface of normal and malignant B-lymphocytes. It is composed of murine light- and heavy-chain variable region sequences and a human constant region sequence. The Rituximab antibody has an approximate molecular weight (MWt) of 145 kD.

Rituximab SPP Preparation
Materials:
Rituximab antibody (stored until use at 4° C., at 10 mg/ml in 9.0 mg/ml sodium chloride, 7.35 mg/ml sodium citrate anhydrate, 0.7 mg/ml Polysorbate 80 and sterile water, pH 6.5)
Procedure:
Rituximab SPPs were formed using a 10,000 MW cut-off Slide-A-Lyzer, according to the method described above for Infliximab (Example 1).
100 μl of a 5-10 mg/ml solution of Rituximab was dialyzed against 3.9 ml of a solution consisting of 2.1 M ammonium sulfate, 0.1 M sodium acetate pH 5.8, 1% propylene glycol. A 10,000 MW cut-off dialysis membrane was used. The mixture was dialyzed at room temperature for 28 hours. Then the protein solution was washed twice in 800 μl of a solution consisting of 2.42 M ammonium sulfate, 1% propylene glycol, 0.1 M sodium acetate, pH 5.8, centrifuged, and resuspended in approximately 200 μl of the same solution.
Results:
Rituximab SPPs formed after 28 hours. See FIG. 1B.

Example 3

Preparation of Spherical Protein Particles of Trastuzumab

Trastuzumab is a monoclonal antibody commercially available as Herceptin™ (Genentech, Inc., South San Francisco, Calif.).
Trastuzumab SPP Preparation
Materials:
Trastuzumab antibody (available as a lyophilized powder containing 22 mg Trastuzumab, 1 mg L-histidine HCl, 0.64 mg L-Histidine, 40 mg trehalose dihydrate, 0.18 mg polysorbate 20), reconstituted in 1 ml water (22 mg/ml), pH 6.
Procedure:
Trastuzumab SPPs were formed using a 10,000 MW cut-off Slide-A-Lyzer, according to the method described above for Example 1.
100 μl of a Trastuzumab solution (at 22 mg/ml Trastuzumab) was dialyzed against 3.9 ml of a solution consisting of 2.1 M ammonium sulfate, 0.1 M sodium acetate pH 5.8, 1% propylene glycol. A 10,000 MW cut-off dialysis membrane was used. The mixture was dialyzed at room temperature for 28 hours. Then the protein solution was washed twice in 800 μl of a solution consisting of 2.42 M ammonium sulfate, 1% propylene glycol, 0.1 M sodium acetate, pH 5.8, centrifuged, and resuspended in approximately 200 μl of the same solution.
Results:
Trastuzumab SPPs formed after 28 hours. See FIG. 1C.

Example 4

Preparation of Spherical Protein Particles of Etanercept

Etanercept is a commercially available monoclonal antibody available as Enbrel™ (Immunex, Seattle, Wash.).
Etanercept SPP Preparation
Materials:
Etanercept antibody (in a solution containing 40 mg mannitol, 10 mg sucrose and 1.2 mg tromethamine).
Procedure:
Entanercept SPPs were formed using a 10,000 MW cut-off Slide-A-Lyzer, according to the method described above for Example 1. A 200 μl aliquot of a 25 mg/ml Etanercept solution (containing 40 mg mannitol, 10 mg sucrose and 1.2 mg tromethamine) was dialyzed against 3.9 ml of a solution consisting of 2.31 M ammonium sulfate, 0.1 M sodium acetate, pH 5.8, 1% propylene glycol. A 10,000 MW cut-off dialysis membrane was used. The mixture was dialyzed at 4° C. for 28 hours. Then the protein solution was washed twice in 800 μl of a solution consisting of 2.62 M ammonium sulfate, 1% propylene glycol, 0.1 M sodium acetate, pH 5.8, centrifuged, and resuspended in approximately 200 μl of the same solution.
Results:
Etanercept SPPs formed after 28 hours.

Example 5

Preparation #2 of Spherical Protein Particles of Etanercept

Etanercept SPP Preparation, Method 2
Materials:
Etanercept SPPs were formed using a 10,000 MW cut-off Slide-A-Lyzer, according to the method described above for Example 1. Etanercept antibody (in a solution containing 40 mg mannitol, 10 mg sucrose and 1.2 mg tromethamine).
Procedure:
25 μl of a 25 mg/ml Etanercept solution was dialyzed against 3.9 ml of a solution consisting of 6 M sodium formate, pH 7.5. A 10,000 MW cut-off dialysis membrane was used. The mixture was dialyzed at 4° C. for 28 hours. Then the protein solution was washed twice in 800 μl of a solution consisting of 6.5 M ammonium sulfate, centrifuged, and resuspended in approximately 100 μl of the same solution.
Results:
Etanercept SPPs formed after 28 hours.

Example 6

Preparation #2 of Spherical Protein Particles of Rituximab: Non-Dialysis Method

Rituximab SPP Preparation
Materials:
Rituximab antibody (stored until use at 4° C., at 10 mg/ml in 9.0 mg/ml sodium chloride, 7.35 mg/ml sodium citrate anhydrate, 0.7 mg/ml Polysorbate 80 and sterile water, pH 6.5)
Procedure:
Aliquots of 4 M ammonium sulfate were added to 200 μl of a 10 mg/ml Rituximab solution, slowly increasing concentration stepwise by 0.2 M, starting with 0.5 M and increasing to 2.2 M. The mixtures were allowed to equilibrate for one hour at each concentration. Samples were periodically analyzed by microscopy to determine sphere formation. Protein content, yield, and the amount of protein remaining in the supernatant was measured by spectroscopy at optical density (OD) of 280 nm and HPLC.
Results:
Rituximab SPPs formed.

Example 7

Preparation of Albumin SPPs

Albumin SPPs were obtained from vapor diffusion hanging drops.
Method:
An aliquot of a 200 mg/ml stock solution of Albumin (in water) was mixed in a 1:1 ratio with a solution of 0.05 M potassium dyhydrogen phosphate, pH 5.5 and 20% (w/v) polyethylene glycol (PEG) 8000 and placed on a plastic coverslip. 1 ml of a reservoir solution containing 0.05 M potassium dyhydrogen phosphate, pH 5.5, 20% (w/v) PEG 8000 was placed in the well (reservoir) of a 24-well Linbro plate (ICN Biomedicals, Inc.). The coverslip was then inverted over the well (reservoir) of the Linbro plate and sealed with vacuum grease. Then the hanging drop solution was allowed to slowly equilibrate with the reservoir solution.

Results:

Albumin SPPs formed overnight in the hanging drops.

Example 8

Preparation of Spherical Protein Particles, Spherical Nanocrystalline Composite Particles or Crystalline SPPs Using Polyethylene Glycol (PEG)

This example illustrates a method of preparing SPPs, spherical nanocrystalline composite particles or crystalline SPPs of various proteins, including, inter alia, enzymes (e.g., urease, glucose oxidase), protein hormones (e.g., human growth hormone), viruses, viral proteins, antibodies e.g., Infliximab, Rituximab, Trastuzumab), antibody fragments, receptors, and peptides (e.g., calcitonin).

Procedure:

Aliquots of 40% PEG of MW 2000-8000 are added to 200 µl of a protein solution (at 5-20 mg protein per ml solution), slowly increasing concentration stepwise by 1%, starting at 4% PEG and increasing stepwise up to 16.5% PEG. The mixtures are allowed to equilibrate for one hour at each concentration. Samples are periodically analyzed by microscopy to determine sphere formation. Protein content, yield, and the amount of protein remaining in the supernatant is measured by spectroscopy at optical density (OD) of 280 nm and HPLC.

Example 9

Preparation of Spherical Protein Particles, Spherical Nanocrystalline Composite Particles or Crystalline SPPs Using PEG-Monomethyl Ether (PEG-ME)

This example illustrates a method of preparing SPPs, spherical nanocrystalline composite particles or crystalline SPPs of various proteins, including, inter alia, enzymes (e.g., urease, glucose oxidase), protein hormones (e.g., human growth hormone), viruses, viral proteins, antibodies (e.g., Infliximab, Rituximab, Trastuzumab), antibody fragments, receptors, and peptides (e.g., calcitonin).

Procedure:

Aliquots of 40% PEG monomethyl ether (PEG-ME) of MW 3350 are added to 200 µl of a protein solution (at 5-20 mg protein per ml solution), slowly increasing concentration stepwise by 1% beyond 4% up to 12% PEG. The mixtures are allowed to equilibrate for one hour at each concentration. Samples are periodically analyzed by microscopy to determine sphere formation. Protein content, yield, and the amount of protein remaining in the supernatant is measured by spectroscopy at optical density (OD) of 280 nm and HPLC.

Example 10

The SPP, spherical nanocrystalline composite particle or crystalline SPP preparation methods exemplified above may be carried out using buffers other than ammonium sulfate, sodium formate, PEG and PEG-ME, including, inter alia, lithium sulfate and MPD.

Example 11

Selective Fractionation/Purification of Infliximab, Rituximab, and Trastuzumab from Milk Proteins by Preparation of SPPs This example contains a method of fractionating/purifying Infliximab, Rituximab, and Trastuzumab, by preparation of SPPs. This method may be used to purify numerous other proteins, including, inter alia, enzymes (e.g., urease, glucose oxidase), protein hormones (e.g., human growth hormone), viruses, viral proteins, antibodies, antibody fragments, receptors, and peptides (e.g., calcitonin).

Materials:

Raw milk was purchased at a local farm (Crystal Brook Farm, Sterling, Mass.) and stored at 4° C.

Procedure:

A 100 ml aliquot of milk was transferred to two (50 ml each) 50 ml centrifuge tubes and de-fatted by centrifugation at 9500 rpm for 15 minutes at 4° C. The cream layer was punctured using a sharp pipette tip and the skim milk was decanted into a clean tube through the opening. The skim milk was then re-centrifuged (9500 rpm for 15 minutes at 4° C.) to remove any residual fat. The skim milk was then clarified by adding an equal volume of 250 mM EDTA. The milky appearance cleared, indicating the destruction of micellar structures and aggregates. Each 50 ml aliquot of EDTA-clarified skim milk was then dialyzed at 4° C. against 1 liter of phosphate-buffered saline (PBS) to remove the EDTA. The dialyzed solution was then centrifuged at 10,000 rpm for 20 minutes and then passed through a 0.2 µm filter and assayed for protein concentration. The milk had a final protein concentration of approximately 7 mg/ml. Three of the clarified milk aliquots were then spiked with an equal volume of stock Infliximab, Rituximab, or Trastuzumab solution, to a final concentration of approximately 5-12 mg/ml protein. The purification of the Infliximab, Rituximab, and Trastuzumab proteins that had been spiked into clarified milk was performed as follows:

200 µl of a protein/clarified milk solution was dialyzed against 3.9 ml of a buffer consisting of 1.8 M ammonium sulfate, 0.05 M sodium acetate, pH 5.8, and 0.5% propylene glycol at 4° C. for 18 hours, using a dialysis membrane with a 10,000 MW cut-off. After 18 hours, the protein solution was then washed twice in 800 µl of a solution containing of 1.8 M ammonium sulfate, 0.5% propylene glycol, and 0.05 M sodium acetate, pH 5.8, centrifuged, and resuspended in approximately 200 µl of the same solution.

Results:

Infliximab, Rituximab, and Trastuzumab were fractionated/purified away from the milk proteins. See FIG. 8.

In addition to using SPPs, the method according to this example may be used to fractionate/purify proteins by preparation of spherical nanocrystalline composite particles or crystalline SPPs.

Example 12

The SPP, spherical nanocrystalline composite particle or crystalline SPP preparation conditions exemplified above are useful for any clinically relevant protein. Clinically relevant proteins may be classified according to the therapeutic area in which they are to be employed. Such proteins include, but are not limited to, commercially available proteins, including antibodies, including, but not limited to:

(1) Abciximab (ReoPro™): (anti-GPIIB/IIIa receptor; for the treatment of cardiovascular disease) (Centocor, Leiden, The Netherlands),
(2) Palivizumab (Synagis™): (anti-F protein on RSV; respiratory disease) (manufactured by MedImmune (Gaithersburg, Md.))
(3) Murumonab-CD3 (Orthoclone™): (anti-CD3 antibody; for tissue transplant rejection) (OrthoBiotech, Raritan, N.J.),
(4) Gemtuzumab (Mylotarg™): (cancer) (Wyeth Labs, Philadelphia, Pa.),
(5) Basiliximab (Simulect™): (anti-CD25 antibody; for tissue transplant rejection) (Novartis, Basel, Switzerland),
(6) Daclizumab (ZenaDax™): (anti-CD25 antibody, for tissue transplant rejection) (Protein Design Labs, Fremont, Calif.),
(7) Zevalin: (radioimmunotherapy for cancer) (IDEC Pharmaceuticals, San Diego, Calif.),
(8) Mylotarg™: (anti-CD33 antibody).

Example 13

Removal of Antibody Aggregates During Formation of Antibody SPPs, Spherical Nanocrystalline Composite Antibody Particles or Crystalline Antibody SPPs This example illustrates a method for the removal of antibody aggregates from an antibody preparation. Precipitants including, inter alia, ammonium sulfate, formate and PEG, which are used to form SPPs also serve to remove protein aggregates at lower concentrations.

Procedure:

Obtain antibody solution (at 10 mg/ml antibody) that contains aggregates. Determine the extent of protein aggregation by size exclusion chromatography. In increments, add stock solutions of either 2 M ammonium sulfate, 40% PEG (to a final concentration up to 6.5% PEG, depending upon the protein in question) or 8 M formate (to a final concentration of approximately 0.9 M, again depending on the protein in question). The aggregated protein precipitates out first, leaving the non-aggregated protein in solution. Protein distribution between pellet and solution is followed by HPLC.

Example 14

Secondary Structure Characterization by FTIR

The following method is especially useful for measuring the secondary structure of proteins. Specifically, it can be used for measuring the β-sheet content or the α-helical content of a protein being assayed. In this way, the secondary structure of the protein component of SPPs, spherical nanocrystalline composite particles or crystalline SPPs maintained in mother liquor, or of proteins derived from dissolving SPPs, spherical nanocrystalline composite particles or crystalline SPPs, may be compared to their native, soluble counterparts. In this way, the effect of, e.g., 1) forming SPPs, spherical nanocrystalline composite particles or crystalline SPPs, 2) short- or long-term storage, and 3) generating compositions or formulations of SPPs, spherical nanocrystalline composite particles or crystalline SPPs, on the native, biologically active protein, may be determined.

The correlation coefficient is calculated using protein analysis software from Nicolet, which easily allows the determination of the correlation coefficient between the previously saved reference spectrum and that of the current protein spectrum (Garland, B, *FT-IR Studies of Protein Secondary Structure in Aqueous and Dried States*. Nicolet application note # AN 9479). The second derivative spectrum of the native aqueous protein is used as a reference spectrum and the dried SPPs, spherical nanocrystalline composite particles or crystalline SPPs and lyophilized solid protein can be used as samples. The proteins will have an increasingly similar secondary conformational structure as the correlation coefficient approaches unity. Denaturation is indicated by a correlation coefficient of less than 0.8, which indicates that 1) the β-sheet content of the native protein has either increased or decreased, or 2) the α-helical content of the native protein has decreased only (i.e., whereas the β-sheet content of a protein could increase or decrease upon denaturation, the α-helical content of a protein always decreases upon denaturation). Therefore, a correlation coefficient of less than 0.8 indicates a change of secondary structure due to denaturation of the protein being assayed, relative to the native, biologically active form of the protein.

A correlation constant of 0.8-1.0 means that the secondary structure (i.e., β-sheet content and/or α-helical content) of the protein being assayed is from about 80% to about 100% identical to that of the native, biologically active form of the protein.

Procedure:

The secondary structure of Trastuzumab SPPs made according to the method of Example 3, Infliximab SPPs made according to the method of Example 1, and Rituximab SPPs made according to the method of Example 2 maintained in suspension in their respective mother liquor was compared to the secondary structure of their native, soluble counterparts. The Fourier transform infrared (FTIR) spectra of the SPPs in suspension and of the native, soluble antibodies were collected on a Nicolet model 550 Magna series spectrometer as described by Dong et al. [Dong, A., Caughey, B., Caughey, W. S., Bhat, K. S. and Coe, J. E. *Biochemistry*, 1992; 31:9364-9370; Dong, A. Prestrelski, S. J., Allison, S. D. and Carpenter, J. F. *J. Pharm. Sci.*, 1995; 84: 415-424.]. The FTIR spectra of the SPPs in suspension was then compared to that of their respective native, soluble counterparts.

The correlation coefficient was calculated using protein analysis software from Nicolet which easily allows the determination of the correlation coefficient between the previously saved reference spectrum and that of the current protein spectrum (Garland, B, *FT-IR Studies of Protein Secondary Structure in Aqueous and Dried States*. Nicolet application note # AN 9479).

The FTIR spectra of 1 ml of each of the SPP solutions (maintained on suspension in mother liquor) at approximately 10 mg SPP per ml was analyzed using the attenuated total reflectance (ATR) mode. The spectra were collected and then processed using Grams 32 (from Galactic Software, Salem, N.H.) for the determination of relative areas of the individual components of secondary structure using second derivative and curve-fitting program under amide I region (1600-1700 cm$^{-1}$).

Results:

A correlation coefficient of greater than 0.8 was obtained for the Trastuzumab SPPs as compared to native, soluble Trastuzumab, indicating that the process of forming Trastuzumab SPPs did not harm the integrity of the intact antibody or alter its native structure by more than 20%. This is corroborated by the nearly identical spectra seen in FIG. 2.

A correlation coefficient of greater than 0.8 was obtained for the Infliximab SPPs as compared to native, soluble Infliximab, indicating that the process of forming Infliximab SPPs did not harm the integrity of the intact antibody or alter its native structure by more than 20%. This is corroborated by the nearly identical spectra seen in FIG. 3.

A correlation coefficient of greater than 0.8 was obtained for the Rituximab SPPs as compared to native, soluble Rituximab, indicating that the process of forming Rituximab SPPs did not harm the integrity of the intact antibody or alter its native structure by more than 20%. This is corroborated by the nearly identical spectra seen in FIG. 4.

FTIR analysis according to this example may be used to determine the secondary structure of any protein that exists as the protein component of an SPP, spherical nanocrystalline composite particle or crystalline SPP, wherein the SPP, spherical nanocrystalline composite particle or crystalline SPP is maintained in its mother liquor. FTIR analysis according to this example may be used for any protein obtained from dissolving SPPs, spherical nanocrystalline composite particles or crystalline SPPs, or for SPPs, spherical nanocrystalline composite particles or crystalline SPPs that have been dried into solid samples. For the solid samples, the diffuse reflectance mode is used instead of the attenuated total reflectance (ATR) mode used for proteins, SPPs, spherical nanocrystalline composite particles or crystalline SPPs in suspension. For solid samples, the protein is lightly ground with 350 mg of KBr powder and filled into small cups used for diffuse reflectance accessory.

Example 15

Bioimmunoassays for the Determination of Biological Activity of Antibodies

The biological activity of an antibody may be characterized and measured by so-called bioimmunoassays that include, inter alia, the three bioimmunoassays described below. These assays are useful for comparing the residual biological activity of antibodies derived from antibody SPPs, spherical nanocrystalline composite antibody particles or crystalline antibody SPPs with their soluble antibody counterparts. In this way, the effects of making SPPs, spherical nanocrystalline composite particles or crystalline SPPs from antibodies, short- or long-term storage, drying, and forming and subsequently dissolving SPP, spherical nanocrystalline composite particle and crystalline SPP compositions or formulations, may be determined and compared to the soluble counterpart of the antibody in question.

The cytotoxicity of an antibody on its antigen bearing target cells can be characterized by three assays, e.g. direct cytotoxicity, complement dependent cytotoxicity (CDC), and antibody-dependent cell-mediated cytotoxicity (ADCC). The target cells for Rituxan are the cells that overexpress CD-20 antigen on their surface, which include Raji, Daudi, JOK1 and WT100. The specific antigen for Herceptin is HER2 (human epidermal growth factor receptor 2 protein), which is overexpressed in human breast adenocarcinoma cell lines including SK-BR-3, BT474, and MCF/HER2.

Example 16

Direct Cytotoxicity Bioimmunoassays Comparing Rituximab from Dissolved Rituximab SPPs with Native, Soluble Rituximab Direct Cytotoxicity:
Direct cytotoxicity, as the name implies, measures the intrinsic toxic effect of an antibody on the target cell by co-incubating the target cells with different concentrations of antibody. Cell viability is counted after co-incubation with antibody.

Procedure:
1) RAJI lymphoma cells, (from American Type Cell Collection (ATCC), Manassas, Va., ATCC # CCL 86) were cultured in growth media and diluted to a final concentration of $0.5 \times 10^5$ cells/ml in the same growth media.
2) 5000 cells (100 μl) were transferred to each well of a 96-well assay plate.
3) In another 96-well plate, Rituximab obtained from dissolving Rituximab SPPs (made according to the method of Example 2) according to Example 18 and native, soluble Rituximab were serially diluted in cell culture media.
4) A 100 μl aliquot of the diluted antibody solution was transferred to each well of the assay plate containing the cells. This produced a final assay volume of 200 μl of antibody/cell solution per well. Wells that contained cells without antibodies (100 μl of growth media alone) were used as a control ("cells only" control). The plates were incubated at 37° C. for 3 days.
5) After 3 days, 20 μl of Promega Substrate Cell Titer 96 Aqueous One Solution Reagent were added to each well.
6) The optical density (OD) at 490 nm was then read at 37° C. The absorbance at 490 nm in the wells containing dissolved Rituximab or its native, soluble counterpart was compared to the "cells only" control. A decrease in absorption as compared to the "cells only" control was an indicator of RAJI lymphoma cell growth inhibition. The ability of Rituximab obtained from dissolving Rituximab SPPs to inhibit RAJI lymphoma cell growth was compared to that of native, soluble Rituximab.

Results:
Rituximab obtained from dissolving Rituximab SPPs according to Example 18 induced Direct Cytotoxicity of RAJI lymphoma cells that was comparable to that of its native, soluble Rituximab counterpart, assayed under identical conditions. See FIG. 9.

Example 17

Complement Dependent Cytotoxicity (CDC) Bioimmunoassays Comparing Rituximab from Dissolved Rituximab SPPs with Native, Soluble Rituximab Complement Dependent Cytotoxicity (CDC):
A complement-dependant cytotoxicity reaction occurs when an antibody binds to its cell surface antigen, and thereby induces target cell destruction by activating the complement system (a series of interacting proteins that lyse cells and trigger local inflammatory reactions).

Procedure:
1) RAJI lymphoma cells, (from American Type Cell Collection (ATCC), Manassas, Va., ATCC # CCL 86) were cultured in growth media and diluted to a final concentration of $0.5 \times 10^5$ cells/ml in the same growth media.
2) 5000 cells (100 μl) were transferred to each well of a 96-well assay plate, and cultured in the presence of either: Rituximab (at 25 μg/ml of cell culture media) obtained from dissolving Rituximab SPPs (made according to the method of Example 2) according to Example 19, or native, soluble Rituximab at 25 μg/ml of cell culture media, and various concentrations of human serum. Wells that contained cells without antibodies were used as a control ("cells only" control). The plates were incubated at 37° C. for 3 days.
3) After the 3 day incubation period, the number of viable RAJI lymphoma cells were counted in each well, using the CellTiter 96-Aqueous One Solution Proliferation Assay kit (Promega Corp. Madison, Wis.; Promega product no. G3580). The number of viable cells in the wells containing Rituximab obtained from dissolving Rituximab SPPs according to Example 18 was compared with the number of viable cells in wells containing native, soluble Rituximab and cells with no antibody (the "cells only" control).

Results:

See FIG. 10.

Example 18

Antibody-Dependent Cell-Mediated Cytotoxicity (ADCC) Bioimmunoassays

Antibody-Dependent Cell-Mediated Cytotoxicity (ADCC):

Similar to CDC, ADCC is one of the major mechanisms responsible for cytotoxicity of monoclonal antibodies. In contrast to CDC, the target cell destruction caused by ADCC is initiated by recruiting immune cells, which specifically attack tumor cells, after an antibody binds to its specific antigen on the target cell. The ADCC assay is carried out by first seeding the wells/plates with a fixed amount of target cells (tumor cells), then co-incubating with antibody and effector immune cells (usually isolated peripheral blood mononuclear cells (PBMCs). The cell viability is determined at the end of co-incubation. Cell death is significantly increased with the presence of the effector immune cells compared with the control (target cell plus antibody only).

Procedure:

Peripheral blood mononuclear cells (PBMCs) are prepared from the buffy coats of healthy blood donors. The buffy coats are first diluted in phosphate-buffered saline (PBS) and the PBMCs are prepared by Ficoll-Hypaque density gradient centrifugation according to the method of Boyum et al., (Scand. J. Clin. Lab. Invest. Suppl. 97, 77-89) (1968). The cells are suspended in medium containing heat-inactivated fetal calf serum (FCS) and 10% dimethylsulfoxide, then aliquoted and freeze-stored in liquid nitrogen until further use. PBMCs are thawed, washed 3 times in same medium and once in PBS, incubated with red membrane dye PKH-26 (Sigma Chemical Co.) at 2 $\mu$M for 4 min. The reaction tube is agitated slightly at room temperature.

Lymphoma cell lines, e.g., RAJI and DUADI (DSMZ, Braunschweig, Germany) are maintained in exponential growth conditions in 12.5 ml medium in plastic 25-cm$^2$ culture flasks (Greiner, Solingen, Germany). The cells are harvested, washed in PBS and incubated with PKH-2 (green fluorescence) at 2 $\mu$M for 10 min. Staining is stopped by addition of FCS and the labelled cells washed 3 times with medium. Cell counts are performed to determine the number of viable cells surviving the staining process. Cell counts are performed using trypan blue stain in a Neubauer chamber and uniform cell labeling is ascertained by UV fluorescence microscopy. Lymphoma cells and PBMCs are seeded in a 96-well flat-bottom microtiter plates (Nunc, Denmark). Next, the antibody of choice is added, along with fresh drawn human serum (as a source of complement), and cytokines. The plates are then incubated for 3 days at 37° C. and 5% $CO_2$ in a humidified atmosphere. After incubation, the plates are washed in PBS. Following the wash step, 50 $\mu$l of PBS supplemented with warm EDTA (to 0.02% final concentration) and trypsin (to 0.05% final concentration), are added to each well. After incubation for 10 minutes, the plates are agitated on a plate shaker for 1 minute. A 200 $\mu$l aliquot of PBS containing 45% FCS are added (to block trypsin activity), propidium iodide (12.5 $\mu$g/ml) is added for labeling of dead cells, and FITC-labelled chronic lymphocyte leukemia lymphocytes (150,000 cells/ml, i.e., 30,000 cells per 200 $\mu$l) are added as standards for cell count determination. All sample analysis is performed by flow cytometry in a FACScan (Becton Dickinson, San Jose, Calif., USA) flow cytometer using identical gates and instrument settings. The number of viable tumor cells in each well is calculated using the formula:

Viable Tumor Cells=30,000×(Events(tumor cell gate)/ Events(standard Cell gate)), where 30,000 is the number of standard cells added to each well.

Example 19

Soluble Protein Sample Preparation

For comparison to the its native, soluble counterpart, the protein component of SPPs, spherical nanocrystalline composite particles or crystalline SPPs produced in Examples 1-9 is prepared by dissolving (resuspending) the SPPs, spherical nanocrystalline composite particles or crystalline SPPs to a final concentration of about 10 to about 20 mg/ml in 0.1% Tween 80 and 25 mM Tris-HCl, pH 7.0 at 37° C.

Example 20

Stability of SPPs, Spherical Nanocrystalline Composite Particles or Crystalline SPPs The stability Rituximab or Trastuzumab SPPs, prepared according to Examples 2 and 3, was compared to the stability of their native, soluble counterpart proteins.

FIG. 5 shows a comparison of the stability of Rituximab SPPs and native, soluble Rituximab, stored at 4° C. for the same period of time. The Rituximab SPPs were dissolved according to the method in Example 19. The analysis was performed by SEC-HPLC. The results show that the Rituximab SPPs were not degraded while in storage.

FIG. 7 is a picture of an SDS-PAGE gel when Trastuzumab and Rituximab SPPs, made according to Examples 3 and 2, respectively, were stored at 4° C. under the same conditions and for the same length of time as native, soluble Trastuzumab and Rituximab. After being stored, the native, soluble Trastuzumab and Rituximab, and dissolved Trastuzumab and Rituximab SPPs (dissolved according to Example 19), were electrophoresed using SDS-PAGE. FIG. 7 demonstrates that Trastuzumab and Rituximab SPPs are stable when stored under the same conditions as their native, soluble counterparts.

The stability of any SPP, spherical nanocrystalline composite particle or crystalline SPP, or composition or formulation thereof, according to this invention may be tested versus their native, soluble counterparts using the methods of this example.

Example 21

Formulation of SPPs, Spherical Nanocrystalline Composite Particles or Crystalline SPPs Using Polyethylene Oxide (PEO) as Excipient In order to enhance the stability of SPPs, spherical nanocrystalline composite particles or crystalline SPPs during drying and storage, the SPPs, spherical nanocrystalline composite particles or crystalline SPPs may be formulated with excipients. SPPs, spherical nanocrystalline composite particles or crystalline SPPs may be formulated using 0.1% polyethylene oxide in water as follows. The SPPs, spherical nanocrystalline composite particles or crystalline SPPs are separated from the preparation buffer by centrifugation at 1000 rpm in a Beckman GS-6R bench top centrifuge equipped with swinging bucket rotor. Next, the SPPs, spherical nanocrystalline composite particles or crystalline SPPs are suspended in 0.1% polyethylene oxide for 3 hrs (Sigma Chemical Co., St. Louis, Mo.) and then separated by centrifugation.

Example 22

Formulation of SPPs, Spherical Nanocrystalline Composite Particles or Crystalline SPPs Using Sucrose as Excipient In this example, sucrose (Sigma Chemical Co., St. Louis, Mo.) is added as an excipient to SPPs, spherical nanocrystalline composite particles or crystalline SPPs in preparation buffer. Sufficient sucrose is added to SPPs, spherical nanocrystalline composite particles or crystalline SPPs to reach a final sucrose concentration of 10% (w/v). The resulting suspension is then tumbled at room temperature for 3 hr. After treatment with sucrose, the SPPs, spherical nanocrystalline composite particles or crystalline SPPs are separated from the liquid by centrifugation, as described in Example 21.

Example 23

Formulation of SPPs, Spherical Nanocrystalline Composite Particles or Crystalline SPPs Using Trehalose as Excipient SPPs, spherical nanocrystalline composite particles or crystalline SPPs are formulated as in Example 22, by adding trehalose instead of sucrose, (Sigma Chemical Co., St. Louis, Mo.), to a final concentration of 10% (w/v) in preparation buffer. The resulting suspension is then tumbled at room temperature for 3 hr and the SPPs, spherical nanocrystalline composite particles or crystalline SPPs are separated from the liquid by centrifugation, as described in Example 21.

Example 24

Formulation of SPPs, Spherical Nanocrystalline Composite Particles or Crystalline SPPs Using Methoxypolyethylene Glycol (MOPEG) as Excipient SPPs, spherical nanocrystalline composite particles or crystalline SPPs are formulated as in Example 22, by adding methoxypolyethylene glycol (Sigma Chemical Co., St. Louis, Mo.) instead of sucrose, to a final concentration of 10% (w/v) in preparation buffer and separating after 3 hrs by centrifugation, as described in Example 21.

Example 25

Making Stable Rituximab and Trastuzumab SPPs that are Particularly Suitable for Parenteral Injection The high ammonium sulfate content (2.1 M) of the mother liquor used in making Rituximab and Trastuzumab SPPs according to the methods of Examples 2 and 3, respectively, is disadvantageous when the SPPs are intended for delivery to a human, or another animal, via parenteral injection. The following method was used to reduce the ammonium sulfate content of SPP solutions intended for parenteral delivery to animals including, inter alia, humans.

Rituximab and Trastuzumab SPPs were made according to Examples 2 and 3, respectively. The mother liquor was removed from the Rituximab and Trastuzumab SPP solutions by centrifugation at 2000 rpm for 10 minutes at room temperature. Rituximab SPPs were resuspended in a solution consisting of 16% PEG 1500, 9% ethanol, 4.5% glycofurol, 4.5% Pluronic F127 and 0.09 M trehalose. Trastuzumab SPPs were resuspended in a solution consisting of 16% PEG 1500, 9% ethanol, 4.5% glycofurol, 4.5% Pluronic F127, 0.09 M trehalose and 4.5% propylene glycol. The centrifugation step was repeated twice and the Rituximab and Trastuzumab SPPs were resuspended in the same respective solutions at a final concentration (protein in solution) of 10 mg/ml.

Results:

The Rituximab and Trastuzumab SPP solutions made according to this example, and their soluble counterparts, were stored for two weeks at 26° C. At weeks 1 and 2, the stability of the Rituximab and Trastuzumab SPPs was found to be comparable to that of their native, soluble counterparts. See FIG. 16.

Example 26

Methods of Drying SPPs, Spherical Nanocrystal Composite Particles or Crystalline SPPs, or Compositions or Formulations Thereof Method 1. $N_2$ Gas Drying at Room Temperature:

SPPs, spherical nanocrystalline composite particles or crystalline SPPs, or compositions and formulations thereof, are separated from the preparation buffer containing excipient by centrifugation at 1000 rpm in a Beckman GS-6R bench top centrifuge equipped with swinging bucket rotor in a 50 ml Fisher brand Disposable centrifuge tube (Polypropylene). The SPPs, spherical nanocrystalline composite particles or crystalline SPPs are then dried by passing a stream of nitrogen at approximately 10 psi pressure into the tube overnight.

Method 2. Vacuum Oven Drying:

SPPs, spherical nanocrystalline composite particles or crystalline SPPs, or compositions and formulations thereof, are first separated from the preparation buffer/excipient solution using centrifugation at 1000 rpm in a Beckman GS-6R bench top centrifuge equipped with swinging bucket rotor in a 50 ml Fisher brand Disposable polypropylene centrifuge tube. The wet SPPs, spherical nanocrystalline composite particles or crystalline SPPs are then placed in a vacuum oven at 25 mm pressure in Hg (VWR Scientific Products) at room temperature and dried for at least 12 hours.

Method 3. Lyophilization:

SPPs, spherical nanocrystalline composite particles or crystalline SPPs, or compositions and formulations thereof, are first separated from the preparation buffer/excipient solution using centrifugation at 1000 rpm in a Beckman GS-6R bench top centrifuge equipped with swinging bucket rotor in a 50 ml Fisher brand Disposable polypropylene centrifuge tube. The wet SPPs, spherical nanocrystalline composite particles or crystalline SPPs are then freeze dried using a Virtis Lyophilizer Model 24 in semistoppered vials. The shelf temperature will be slowly reduced to −40° C. during the freezing step. This temperature will be held for 16 hrs. Secondary drying may then be then carried out for another 8 hrs.

Method 4. Organic Solvent and Air Drying:

SPPs, spherical nanocrystalline composite particles or crystalline SPPs, or compositions and formulations thereof, are first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The SPPs, spherical nanocrystalline composite particles or crystalline SPPs are then suspended in an organic solvent like ethanol or isopropanol or ethyl acetate or other suitable solvents, and centrifuged. The supernatant is then decanted and the SPPs are air dried or dried under a gentle stream of nitrogen at room temperature in the fume hood for about 30 minutes to about two days (depending on SPP sample size), until the SPPs are completely dry.

Method 5. Air Drying at Room Temperature:

SPPs, spherical nanocrystalline composite particles or crystalline SPPs, or compositions and formulations thereof, are separated from the preparation buffer containing excipient by centrifugation at 1000 rpm in a Beckman GS-6R bench top centrifuge equipped with swinging bucket rotor in a 50 ml Fisher brand Disposable centrifuge tube (Polypropylene). Subsequently, the SPPs, spherical nanocrystalline composite particles or crystalline SPPs are then allowed to air dry in the fume hood for two days.

Method 6. Spray Drying:

SPPs, spherical nanocrystalline composite particles or crystalline SPPs, or compositions and formulations thereof, are spray dried using a Buchi Mini Spray Dryer Model B-191. The SPPs, spherical nanocrystalline composite particles or crystalline SPPs, at a concentration of 30 to 50 mg/ml, are used for spray drying.

Example 27

Drying Rituximab SPPs

Rituximab crystals were made according to the method of Example 6, and dried according to method 4 of Example 26.

Drying Rituximab SPPs:

A solution containing 1.5 mg of Rituximab SPPs in mother liquor was centrifuged at 1000 rpm for 10 minutes at room temperature. The mother liquor was then removed from the Rituximab SPPs, and the Rituximab SPPs were resuspended in 6% Pluronic F127 (a surfactant) (gift from the BASF corporation) in 70% 2-Propanol (isopropanol). This solution was then centrifuged at 1000 rpm until the solvent could be removed (10 minutes at room temperature). The solvent was removed and the Rituximab SPPs were resuspended in solution of 25% Propylene glycol/75% 2-Propanol. This solvent was then removed from this solution by centrifugation at 1000 rpm (10 minutes at room temperature), and the Rituximab SPPs were resuspended in 100% 2-propanol. The 2-propanol was then removed from this solution by centrifugation at 1000 rpm (10 minutes at room temperature). The Rituximab SPPs were then dried in a gentle stream of nitrogen. Because the sample size was small (1.5 mg), the SPPs were completely dried after 45 minutes.

Example 28

Dimethyl 3,3'-dithiobispropionimidate.HCl (DTBP) Crosslinking

Dimethyl 3,3'-dithiobispropionimidate HCl (DTBP) solution is prepared by dissolving 27.9 mg of DTBP in 60 ml of water. A 40 ml aliquot of this solution is then added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of DTBP is added (20 ml) and crosslinking is continued for another 24 hours. The crosslinking is terminated by washing off excess reagent five times, with 1 ml each time of 10 mM sodium acetate buffer, pH 4.8 containing 10 mM calcium chloride and 20% MPD.

Example 29

Dithiobis(succinimidylpropionate) (DSP) Crosslinking

Dithiobis(succinimidylpropionate) (DSP) solution is prepared by dissolving 36 mg of DSP in 60 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of DSP is added (20 ml) and crosslinking is continued for another 24 hours. The crosslinking is terminated by washing off (five times with 1 ml of buffer each time) excess reagent with 10 mM sodium acetate buffer, pH 4.8 containing 10 mM calcium chloride and 20% MPD.

Example 30

Bis Maleimidohexane (BMH) Crosslinking

Bis maleimidohexane (BMH) solution is prepared by dissolving 12 mg of BMH in 40 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 7.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of BMH is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 31

Bis[Sulfosuccinimidyl]suberate (BS) Crosslinking

Bis[Sulfosuccinimidyl]suberate (BS) solution is prepared by dissolving 29 mg of BS in 50 ml of water. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of BS is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 32

1,5-Difluoro-2,4-dinitrobenzene (DFDNB) Crosslinking 1,5-Difluoro-2,4-dinitrobenzene (DFDNB) solution is prepared by dissolving 10 mg of DFDNB in 40 ml of acetone. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of DFDNB is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 33

Dimethylsuberimidate.2HCl (DMS) Crosslinking

Dimethylsuberimidate.2HCl (DMS) solution is prepared by dissolving 33 mg of DMS in 40 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of DMS is added (20 ml) and crosslinking is continued for another 24 hours. The crosslinking reaction is terminated by washing off excess reagent with 10 mM sodium acetate buffer, pH 4.8 containing 10 mM calcium chloride and 20% MPD (×5 with 1 ml of buffer).

Example 34

Disuccinimidyl Glutarate (DSG) Crosslinking

Disuccinimidyl glutarate (DSG) solution is prepared by dissolving 17 mg of DSG in 50 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. After that, the slurry is centrifuged at 3000 rpm and the supernatant is discarded. The pellet is then suspended in 10 mM HEPES buffer, pH 7.5 containing 10 mM calcium chloride and 20% MPD. An additional amount of DSG is added (20 ml) and crosslinking is continued for another 24 hours. The crosslinking is terminated by washing excess reagent with 10 mM sodium acetate buffer, pH 4.8 containing 10 mM calcium chloride and 20% MPD (×5 with 1 ml of buffer).

Example 35

Disulfosuccinimidyl Tartarate (Sulfo-DST) Crosslinking

Disulfosuccinimidyl tartarate (Sulfo-DST) solution is prepared by dissolving 27 mg of Sulfo-DST in 50 ml of water. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. After that, the slurry is centrifuged at 3000 rpm and the supernatant is discarded. The pellet is then suspended in 10 mM HEPES buffer, pH 7.5 containing 10 mM calcium chloride and 20% MPD. An additional amount of Sulfo-DST is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 36

1-Ethyl-3-[3-Dimethylaminopropyl]carbodiimide hydrochloride (EDC) Crosslinking 1-Ethyl-3-[3-Dimethylaminopropyl]carbodiimide hydrochloride (EDC) solution is prepared by dissolving 10 mg of EDC in 1 ml of water. A 200 ml aliquot of this solution and 5 mg of solid Sulfo-NHS is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. After 24 hours, the slurry is centrifuged at 3000 rpm and the supernatant is discarded. The pellet is then suspended in 50 mM MES buffer, pH 6 containing 10 mM calcium chloride and 20% MPD. An additional amount of EDC+Sulfo-NHS is added (200 ml+5 mg Sulfo-NHS) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 37

Ethylene Glycolbis[sulfosuccinimidylsuccinate] (Sulfo-EGS) Crosslinking

Ethylene glycolbis[sulfosuccinimidylsuccinate] (Sulfo-EGS) solution is prepared by dissolving 33 mg of Sulfo-EGS in 40 ml water. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of Sulfo-EGS is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 38

N-[g-maleimidobutyryloxy]succinimide ester (GMBS) Crosslinking

N-[g-maleimidobutyryloxy]succinimide ester (GMBS) solution is prepared by dissolving 23 mg of GMBS in 50 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours, with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of GMBS is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 39

N-hydroxysulfosuccinimidyl-4-Azidobenzoate (Sulfo-HSAB) Crosslinking

N-hydroxysulfosuccinimidyl-4-azidobenzoate (Sulfo-HSAB) solution is prepared by dissolving 5 mg of Sulfo-HSAB in 40 ml of water. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours, with tumbling. Then, the slurry is centrifuged at 3000 rpm and the supernatant is discarded. The pellet is then suspended in 10 mM HEPES buffer, pH 8.5 containing 10 mM calcium chloride and 20% MPD, and a second crosslinking is carried out at ambient temperature for 10 minutes with shaking using 254 nm UV light (by keeping the UV lamp 2.5 cm away from the sample). After 10 minutes, the slurry is centrifuged at 3000 rpm and the supernatant is discarded. The crosslinking is terminated by washing off excess reagent with 10 mM sodium acetate buffer, pH 4.8 containing 10 mM calcium chloride and 20% MPD (×5 with 1 ml of buffer).

Example 40

Sulfosuccinimidyl-6-[a-methyl-a-(2-pyridyldithio)toluamido]hexanoate (Sulfo-LC-SMPT) Crosslinking Sulfosuccinimidyl-6-[a-methyl-a-(2-pyridyldithio)toluamido]hexanoate (Sulfo-LC-SMPT) solution is prepared by dissolving 12 mg of Sulfo-LC-SMPT in 60 ml of water. A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 24 hours with tumbling. Then, the slurry is centrifuged at 3000 rpm and the supernatant is discarded. The pellet is then suspended in 10 mM HEPES buffer, pH 7.5 containing 10 mM calcium chloride and 20% MPD. An additional amount of Sulfo-LC-SMPT is added (20 ml) and crosslinking is continued for another 24 hours. The crosslinking is terminated by washing off excess reagent with 10 mM sodium acetate buffer, pH 4.8 containing 10 mM calcium chloride and 20% MPD (×5 with 1 ml of buffer).

Example 41

Bis-[b-(4-azidosalicylamido)ethyl]disulfide (BASED) Crosslinking

Bis-[b-(4-azidosalicylamido)ethyl]disulfide (BASED) solution is prepared by dissolving 3 mg of BASED in 40 ml of dimethyl sulfoxide (DMSO). A 40 ml aliquot of this solution is added to SPPs, spherical nanocrystalline composite particles or crystalline SPPs (21 mg in 1.5 ml of 10 mM HEPES buffer, pH 8.5 containing 10 mM calcium chloride and 20% MPD). Crosslinking is carried out at ambient temperature for 30 minutes with shaking using 365 nm UV light (by keeping the UV lamp 2.5 cm away from the sample). After 30 minutes, the slurry is centrifuged at 3000 rpm and the supernatant is discarded. The crosslinking is terminated by washing off excess reagent with 10 mM sodium acetate buffer, pH 4.8 containing 10 mM calcium chloride and 20% MPD (×5 with 1 ml of buffer).

Example 42

Glutaraldehyde Crosslinking

Rituximab SPPs, prepared according to the method of Example 2, were crosslinked by adding untreated neat glutaraldehyde (Sigma) to a final crosslinker concentration of 0.1%. Crosslinking was allowed to proceed for 1 hour. The SPPs or crystalline SPPs were recovered by low speed centrifugation and were washed with 10 mM Tris buffer, pH 7.0.

Example 43

Reversible Crosslinkers—Disulfide Crosslinked SPPs, Spherical Nanocrystalline Composite Particles or Crystalline SPPs SPPs, spherical nanocrystalline composite particles or crystalline SPPs may be crosslinked using one of the following crosslinkers:
1) Dimethyl 3,3'-dithiobispropionimidate.HCl—(DTBP) (Pierce)
2) Dithiobis(succinimidylpropionate)—(DSP) (Pierce)

Crosslinking is carried out in 1.5 ml microcentrifuge tubes (USA/Scientific) by placing 250 ml of SPP, spherical nanocrystalline composite particle or crystalline SPP solution (21 mg) in 500 ml of buffer (10 mM HEPES, pH 8.5 containing 10 mM calcium acetate and 20% MPD). One crosslinker is added to each tube as follows: A) DTBP (60 mM) (27.9 mg of DTBP is dissolved in 60 ml of water and add 20 ml of the solution); and B) DSP (14.84 mM) (36 mg of DSP is dissolved in 120 ml of DMSO and add 10 ml of the solution).

The tubes are tumbled at ambient temperature (24-26° C.) until all samples are determined to be insoluble in 32 mM NaOH (2 days) (using 50 ml sample in 150 ml of NaOH). Uncrosslinked samples are readily soluble in 32 mM NaOH at the same concentrations. Crosslinking is stopped by centrifuging the sample at 3000 rpm for 5 minutes, and discarding the supernatant and by the addition of 1 ml of 10 mM Tris.HCl buffer, pH 7.0 containing 10 mM calcium chloride and 20% MPD and repeating the washing procedure three times.

Example 44

Dissolution of Disulfide Bond-Containing Crosslinked SPPs or SPP Crystals

A 200 mM solution of cysteine is prepared by dissolving 242 mg of cysteine in 10 ml of 10 mM Tris HCl buffer, pH 7 containing 10 mM calcium chloride and 20% MPD. A 200 ml sample of crosslinked SPP, spherical nanocrystalline composite particles or crystalline SPPs is taken and centrifuged at 3000 rpm for 5 minutes and the supernatant is discarded. The pellet is suspended in 200 ml of cysteine containing Tris buffer. Another 200 ml of crosslinked sample is taken and centrifuged at 3000 rpm for 5 minutes and the supernatant is discarded. The pellet is then suspended in 200 ml of Tris buffer without any cysteine. All samples are incubated at 37° C. for 1 hour and monitored for dissolution in 32 mM NaOH (direct visual and microscopic observation).

After incubation for 1 hour at 37° C., the DTBP sample is fully soluble in the presence of cysteine and insoluble in its absence. The DSP sample is barely soluble in the presence of cysteine and insoluble in its absence.

Example 45

Characterization of pH Solubility of Crosslinked SPPs, Spherical Nanocrystalline Composite Particles or Crystalline SPPs at 37° C.

The solubility of various SPPs, spherical nanocrystalline composite particles or crystalline SPPs, crosslinked with Dimethyl 3,3'-dithiobispropionimidate.HCl (DTBP), Dithiobis (succinimidylpropionate) (DSP), Bis maleimido hexane (BMH), Bis[Sulfosuccinimidyl]suberate (BS), 1,5-Difluoro-2,4-dinitrobenzene (DFDNB), Dimethylsuberimidate.2 HCl (DMS), Disuccinimidyl glutarate (DSG), Disulfosuccinimidyl tartarate (Sulfo-DST), 1-Ethyl-3-[3-Dimethylaminopropyl]carbodiimide hydrochloride (EDC), Ethylene glycolbis [sulfosuccinimidylsuccinate] (Sulfo-EGS), N-[g-maleimidobutyryloxy]succinimide ester (GMBS), N-hydroxysulfosuccinimidyl-4-azidobenzoate (Sulfo-HSAB), Sulfosuccinimidyl-6-[a-methyl-a-(2-pyridyldithio) toluamido]hexanoate (Sulfo-LC-SMPT), Bis-[b-(4-azidosalicylamido) ethyl]disulfide (BASED) or glutaraldehyde (GA), may be studied using this method.

In 1.5 ml Eppendorf tubes, samples of uncrosslinked SPPs, spherical nanocrystalline composite particles or crystalline SPPs, and crosslinked SPPs, spherical nanocrystalline composite particles or crystalline SPP preparations, equal to 2.8 mg protein, are microfuged at 3000 rpm for 5 minutes and the supernatant liquid is removed. Two pHs are tested: a) pH 7.4 and b) pH 2.0.

For pH 7.4, a 200 ml aliquot of PBS buffer (0.01 M phosphate, 0.0027 M potassium chloride, 0.137 M sodium chloride, pH 7.4) is added to each sample, bringing the concentration of protein to 14 mg/ml. The samples are incubated at 37° C. for 24 hours.

For pH 2.0, a 200 ml aliquot of glycine.HCl buffer pH 2.0 is added to each sample, bringing the concentration of protein to 14 mg/ml. The samples are incubated at 37° C. for 5 hours. Initially, the samples are treated with 10 mM glycine.HCl buffer, pH 2.0 containing 10 mM calcium chloride and 20% MPD overnight at 25° C. with tumbling; then proceeding with glycine.HCl buffer alone.

Samples are studied for dissolution by centrifuging the samples at 14,000 rpm for 5 minutes after 24 hours/5 hours and the supernatant is passed through 0.22 mm filter. The protein is estimated by removing 2 ml of the aliquot and placing it in 798 ml of deionized water. A 200 ml aliquot of Bio-Rad Protein assay reagent is added to this sample and the sample is then incubated at ambient temperature for 5 minutes and measured at 595 nm wavelength (Bio-Rad micro protein assay by Bradford's method). As a standard, bovine serum albumin from Pierce is used in the range of about 0-20 mg protein.

Example 46

Tertiary Structure Characterization by FTIR

The following method is useful for measuring the tertiary structure of a protein being assayed. In this way, the tertiary structure of proteins derived from dissolving SPPs, spherical nanocrystalline composite particles or crystalline SPPs may be compared to their native, soluble counterparts. In this way, the effect of, e.g., 1) forming SPPs, spherical nanocrystalline composite particles or crystalline SPPs, 2) short- or long-term storage, and 3) generating compositions or formulations of SPPs, spherical nanocrystalline composite particles or crystalline SPPs, on the native, biologically active protein, may be determined.

The fourier transform infrared (FTIR) spectra are collected on a Nicolet model 550 Magna series spectrometer, as described by Dong et al. [Dong, A., Caughey, B., Caughey, W. S., Bhat, K. S. and Coe, J. E. *Biochemistry*, 1992; 31:9364-9370; Dong, A. Prestrelski, S. J., Allison, S. D. and Carpenter, J. F. *J. Pharm. Sci.*, 1995; 84: 415-424.]

For the solid samples, 1 to 2 mg of the protein are lightly ground with 350 mg of KBr powder and filled into small cups used for diffuse reflectance accessory.

Alternatively, for solution analysis, attenuated total reflectance (ATR) is used instead of diffuse reflectance.

The spectra are collected and then processed using Grams 32 (from Galactic Software), for the determination of relative areas of the individual components of secondary structure using second derivative and curve-fitting program under amide I region (1600-1700 cm$^{-1}$).

The correlation coefficient is calculated using protein analysis software from Nicolet, which easily allows the determination of the correlation coefficient between the previously saved reference spectrum and that of the current protein spectrum (Garland, B, *FT-IR Studies of Protein Secondary Structure in Aqueous and Dried States*. Nicolet application note # AN 9479). The second derivative spectrum of the native aqueous protein is used as a reference spectrum and dried SPPs, spherical nanocrystalline composite particles or crystalline SPPs and lyophilized solid protein can be used as samples. The proteins will have an increasingly similar tertiary conformational structure as the correlation coefficient approaches unity. Denaturation is indicated by a correlation coefficient of less than 0.8, which indicates that 1) the β-sheet content of the native protein has either increased or decreased, or 2) the α-helical content of the native protein has decreased only (i.e., whereas the β-sheet content of a protein could increase or decrease upon denaturation, the α-helical content of a protein always decreases upon denaturation). Therefore, a correlation coefficient of less than 0.8 indicates a change of tertiary structure due to denaturation of the protein being assayed, relative to the native, biologically active form of the protein.

Example 47

Secondary Structure Characterization by Circular Dichroism Spectroscopy

Circular Dichroism (CD) is an optical characteristic of a molecule, which reflects asymmetric features of the molecular structure. CD spectroscopy is a method for measuring CD and is useful for the rapid determination of a molecule's structural features. CD spectra allow characterization of the secondary structure of a protein, including the β-sheet content, the α-helical content, the β-turn content and the random coil content of a protein being assayed. CD spectra further allow characterization of the type of structure of a nucleic acid including, inter alia, whether the nucleic acid molecule is in the A-form (A-DNA or A-RNA), B-form (B-DNA) or Z-form (Z-DNA). In this way, the secondary structure of proteins or nucleic acids derived from dissolving SPPs, spherical nanocrystalline composite particles, crystalline SPPs, or spherical nucleic acid particles or spherical nanocrystalline composite nucleic acid particles or crystalline spherical nucleic acid particles may be compared to their soluble counterparts. In this way, the effect of, e.g., 1) forming SPPs, spherical nanocrystalline composite particles or crystalline SPPs, or spherical nucleic acid particles or spherical nanocrystalline composite nucleic acid particles or crystalline spherical nucleic acid particles 2) short- or long-term storage, and 3) generating compositions or formulations of SPPs, spherical nanocrystalline composite particles or crystalline SPPs, or spherical nucleic acid particles or spherical nanocrystalline composite nucleic acid particles crystalline spherical nucleic acid particles, on the native, biologically active protein or nucleic acid, may be determined.

Circular Dichroism (CD) is displayed when an optically active substance absorbs left or right handed circularly polarized light preferentially. CD can define the secondary structure characteristics of proteins and peptides, including alpha helix, beta sheet, turn, and coil. CD spectroscopy has been used to monitor: 1) secondary structure, 2) conformational changes, 3) environmental effects, 4) protein folding and denaturation, and 5) dynamics.

Method:

Infliximab SPPs, Rituximab SPPs and Trastuzumab SPPs were made according to the methods of Examples 1-3, respectively. Infliximab SPPs, Rituximab SPPs and Trastuzumab SPPs were dissolved according to the method of Example 19. The secondary structures of the antibodies obtained from dissolved SPPs were determined with a Jasco-810 circular dichroism spectrometer and were compared with the counterpart soluble protein obtained commercially. The protein SPP samples were dissolved and diluted with deionized water to a final concentration of 0.17-0.33 mg/ml. The spectra were taken from 260 to 195 nm (wavelength in nanometers), using a standard 0.1 cm pathlength cuvette (200 µl sample size). For all three sets of samples (both dissolved SPPs and soluble proteins of Trastuzumab, Rituximab and Infliximab), the spectra demonstrated dominating β-sheet structure and showed no significant differences between the spectra of dissolved SPP and soluble protein samples.

Results: See FIGS. 11, 12 and 13.

Example 48

Conformation Characterization by ELISA

ELISAs measure the ability of a monoclonal antibody to recognize and bind to a specific epitope on a protein. Monoclonal antibodies bind primarily on the global conformation of the epitope and the local conformation of the amino acids that make up the epitope. If a native protein becomes denatured, or its conformation is somehow altered, a monoclonal antibody will no longer recognize it and bind to it. Thus, by using a monoclonal antibody that specifically binds a native, soluble counterpart to a protein component of an SPP, spherical nanocrystalline composite particle or crystalline SPP, an ELISA is useful to compare the antigenic structure of a protein from a dissolved SPP, spherical nanocrystalline composite particle or crystalline SPP with that of its native, soluble counterpart.

Method:

Protocol for Trastuzumab ELISA:

Corning Costar 96-well plates (Corning, Life Sciences Division, Acton, Mass.) were coated with 50 µl of goat anti-human IgG (Pierce Biotechnology, Rockford, Ill.) at a concentration of 10 µg/ml in 50 mM carbonate buffer, pH 9.6. The plates were coated overnight at 4° C.

The next day, the anti-human antibody was aspirated off of the plates, after which the plates were washed 3 times with Tris-buffered saline with 0.05% Tween 20 (Sigma, St. Louis, Mo.) (TBST).

Then, the plates were blocked by adding 200 µl blocking buffer (3% non-fat dry milk reconstituted in TBST) to each well of the plates. The plates were incubated in a dark room at room temperature (21-25° C.) for 2 hours.

While the plates were being blocked, the Trastuzumab samples (either Trastuzumab obtained from dissolving Trastuzumab SPPs (made according to the method of Example 3 and dissolved according to the method of Example 19), or native, soluble Trastuzumab) were diluted to a final concentration of 10 ng/ml in dilution buffer (blocking buffer plus 1% normal mouse serum), and serially diluted 6 times, performing a 1:1 dilution each time. The final concentrations of the Trastuzumab samples were 10 ng/ml, 5 ng/ml, 2.5 ng/ml, 1.25 ng/ml, 0.625 ng/ml, 0.3125 ng/ml and 0.15625 ng/ml.

After the plates were blocked for 2 hours, they were washed 3 times with 200 µl/well TBST. Then, 100 µl of the appropriate diluted sample was added to the appropriate well of the plates. Wells containing blocking buffer only (without Trastuzumab) were used as a control. The plates were then incubated in a dark room at room temperature (21-25° C.) for 1 hour.

After the incubation period, the plates were washed 3 times with 200 µl/well TBST. Then, 100 µl of horseradish peroxidase-conjugated Fc-specific anti-human IgG (Sigma, St. Louis, Mo.) was added to each well of the plates. The plates were then incubated in a dark room at room temperature (21-25° C.) for 1 hour.

After the incubation period, the plates were washed 3 times with 200 µl/well TBST. Then, 100 µl of the substrate 3,3',5,5'-tetramethylbenzidine (TMB) (in the presence of hydrogen peroxide ($H_2O_2$)) was added to each well. The plates were then incubated in a dark room at room temperature (21-25° C.) for 30 minutes to allow the color to develop. The color reaction was then stopped by adding 100 µl of 1 N (Normal) sulfuric acid ($H_2SO_4$) to each well. The optical density (OD) of the solution in each well was measured at a wavelength of 450 nm ($OD_{450}$) using a Molecular Devices "SpectraMAX plus" automatic plate reader with Softmax Pro software Molecular Devices, Sunnyvale, Calif.). The $OD_{450}$ measured for each well was directly proportional to the amount of Trastuzumab bound to the anti-human antibody coating the well.

Results:

The Trastuzumab obtained from dissolving Trastuzumab SPPs had the same conformation as its native, soluble counterpart, demonstrating that the process of forming Trastuzumab SPPs did not alter the conformation of the native Trastuzumab antibody. See FIG. 14.

Example 49

Trastuzumab Animal Models

Trastuzumab may be used in the treatment of breast cancer [Pietras R. J., Poen J. C., Gallardo, D., Wongvipat P. N., Lee H. J. and Slamon D. J., Cancer Res, vol. 59, pp. 1347-55 (1999); Baselga, J., Norton L., Albanell J., Kim Y. M., Mendelsohn J., Cancer Research, vol. 58, pp. 2825-31 (1998)].

Procedure:

Trastuzumab SPPs were made according to the method of Example 3.

Procedure of Tumor Formation in Nude Mice:

Human breast cancer SK-BR3 or BT-474 cells (American Type Culture Collection (ATCC) (Manassas, Va., USA)) were cultured in BRMI 1640 medium supplemented with 10% fetal bovine serum (FBS), 2 mM glutamine and 1% penicillin G/streptomycin/fungizone solution. After a few cell passages, the human breast cancer cells were inoculated subcutaneously (s.c.) ($5 \times 10^7$ cells/animal) in the hind thighs of 3-month-old female athymic mice.

Prior to inoculation, mice were primed for 10-14 days with 17β-estradiol applied subcutaneously in a biodegradable carrier-binder (1.7 mg of estradiol per pellet) to promote growth of the estrogen-dependent breast cancer cells. Tumor nodules were monitored by measuring their dimensions (in mm). Five to six animals were included in each treatment group. The animals were randomly chosen with respect to body weight and tumor nodule size at the start of each treatment. Antibody treatment was initiated when tumors grew to more than 20-30 mm³ in size in one set of animals or to more than 350 mm³ in size in a second set. Recombinant human (rhu) Mab HER-2 antibody (Trastuzumab) SPPs (in suspension) or "non-SPP" crystals (also in suspension) were given subcutaneously at a dose of 10 mg/kg animal body weight in three doses at 4-day intervals (over 12 days). Control injections were of human IgG1 (30 mg/kg), also given subcutaneously, using the same administration protocol. Mice were then sacrificed for pathological examination.

Figure 6:
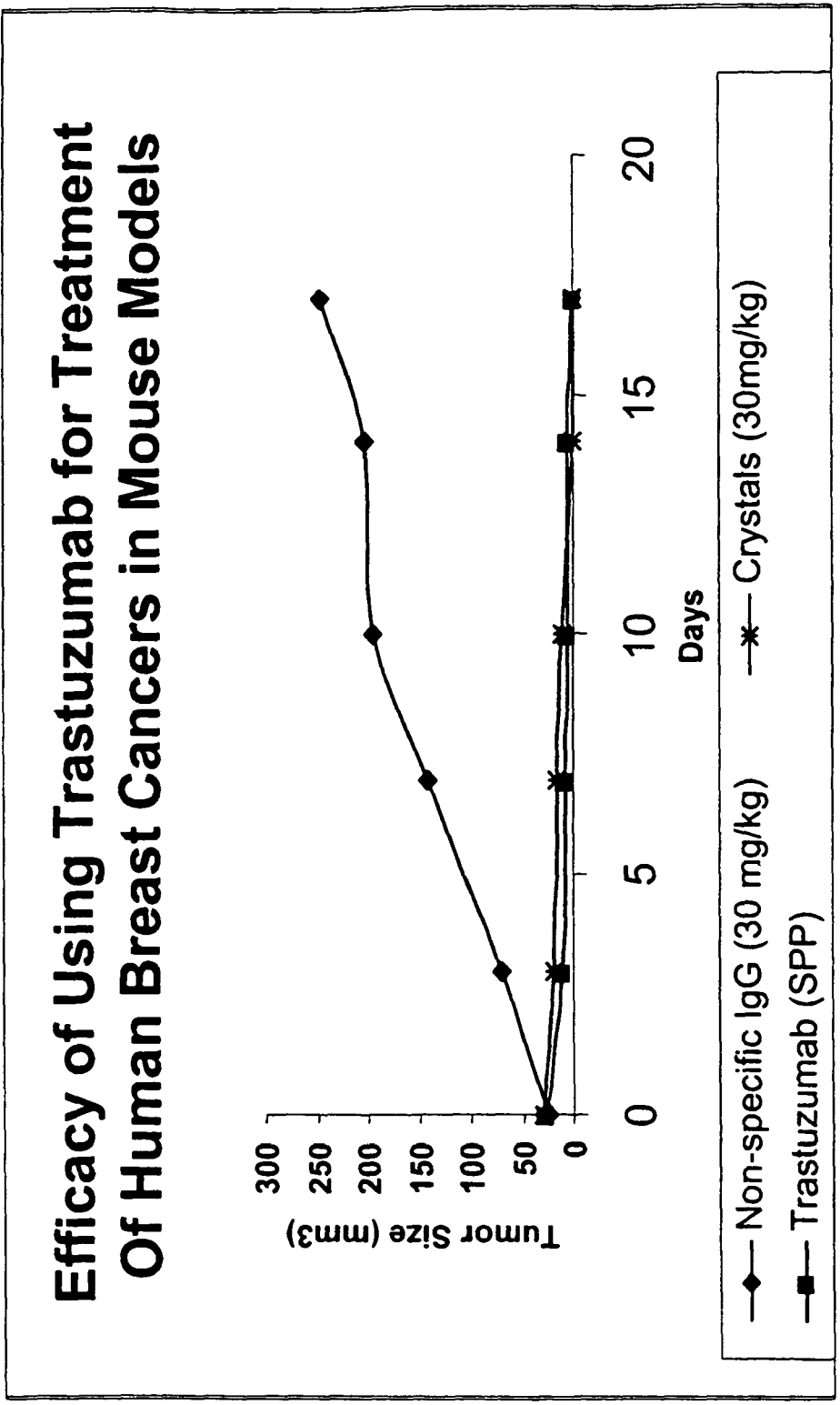
FIG. 6 is a plot comparing the efficacy of using Trastuzumab SPPs for treating a mouse model of human breast cancer with that of Trastuzumab crystals. Native, soluble, non-specific IgG was used as a control. See Example 49.

Results:

Both the Trastuzumab SPPs and the Trastuzumab "non-SPP" crystals eradicated most or all of the tumors formed by injecting BT 474 cells into mice, when compared to controls consisting of saline (which was used as the cell delivery vehicle) or non-specific IgG, clearly indicating that the Trastuzumab SPPs are efficacious in mice animal models for human breast cancer. See FIG. 6, which shows the results when the efficacy of using Trastuzumab SPPs against human breast cancers in a mouse model was compared to that of Trastuzumab crystals.

The animal studies described above are suitable for other antibody SPPs, antibody spherical nanocrystalline composite particles and crystalline antibody SPPs according to this invention, including, inter alia, Infliximab and Rituximab.

Example 50

Oligosaccharide Profiling of Native (Soluble) and Dissolved Rituximab and Trastuzumab Oligosaccharide profiles were performed to compare the carbohydrate constituents of native, soluble Rituximab and Trastuzumab with Rituximab and Trastuzumab obtained from dissolving Rituximab SPPs (made according to the method of Example 2) and Trastuzumab SPPs (made according to the method of Example 3). Rituximab and Trastuzumab SPPs were dissolved according to the method of Example 19.

Procedure:

Oligosaccharide profiling was done by Capillary Electrophoresis on a Beckman-Coulter P/ACE MDQ instrument, following carbohydrate labeling and analysis using a Beckman-Coulter E-CAP kit.

Trastuzumab and Rituximab SPPs (from Examples 2 and 3, respectively) were washed, dissolved, and dialyzed against ddH$_2$0, and samples of soluble Trastuzumab and Rituximab (as supplied by manufacturer) were dialyzed against ddH$_2$0. A 200 µg aliquot of each sample was reconstituted with 50 mM Phosphate buffer, pH 7.0. Sodium dodecyl sulfate (SDS), (2-mercaptoethanol (β-ME), and NP-40 (Tergitol) were added to improve N-linked oligosaccharide cleavage. Subsequently, PNGase (an enzyme that cleaves asparagine-linked oligosaccharides) was added to each sample, and samples were incubated overnight at 37° C. Protein was then precipitated with 3 volumes of cold ethanol, samples were spun, and the supernatants (containing oligosaccharides) were recovered and lyophilized. Oligosaccharide samples were reconstituted and fluorescently labeled with 1-aminopyrene-3,6, 8-trisulfonate (APTS) in the presence of NaBH$_3$CN (sodium cyanoborohydride, a reducing agent which reduces the imine linkage between the labelling reagent and the carbohydrate from reforming after the APTS treatment) at 37° C. overnight. The samples were incubated overnight, diluted in water and read with P/ACE MDQ capillary electrophoresis instrument using a laser-induced fluorescence (LIF) detector. The capillary used was a N—CHO coated capillary provided by Beckman-Coulter with the e-CAP carbohydrate analysis kit.

Results:

The results show that the antibodies obtained from dissolving antibody SPPs had the same carbohydrate content as their native, soluble counterparts, demonstrating that the process of forming Rituximab and Trastuzumab SPPs did not alter the carbohydrate content of the native Rituximab and Trastuzumab antibodies. See FIG. 15.

Example 51

Rituximab SPPs Viewed Using Transmission Electron Microscopy (TEM)

Transmission Electron Microscopy Method:

Samples of Rituximab SPPs, made according to the method of Example 2, were embedded in epoxy resin and allowed to harden. The Rituximab SPP specimens were microtomed and placed on Carbon electron microscopy grids. High magnification TEM images were obtained using a Phillips CM10 transmission electron microscope operating at 60 kV.

Results:

Electron micrographs showed the layered shell structure of a Rituximab SPP. The micrographs also exhibited a 4 nm lattice spacing in the crystalline areas of the Rituximab SPPs.

Example 52

Rituximab and Trastuzumab SPPs Viewed Using Scanning Electron Microscopy (SEM)

Scanning Electron Microscopy Method:

Samples of Rituximab or Trastuzumab SPPs, made according to the methods of Examples 2 and 3, respectively, were placed onto freshly prepared carbon-coated gold support grids. Excess buffer was blotted away using filter paper. The solid was coated with Palladium/Gold under vacuum. The coated specimens were analyzed using an ETEC autoscan scanning electron microscope.

Example 53

Electron Diffraction of Rituximab and Trastuzumab SPPs

Electron Diffraction Method:

The electron diffraction images were recorded at 640 mm camera length, at 60 Kv and the spot size set at 4.

Results:

The diffraction pattern obtained when an electron beam was focused on Rituximab or Trastuzumab SPPs made according to the methods of Examples 2 and 3, respectively, is indicative of the presence of crystallinity in the region of the SPPs that was analyzed. In contrast, when an electron beam was focused on an amorphous solid consisting of a formvar support polymer on a TEM sample grid, no diffraction pattern was obtained, which is indicative of an amorphous substance.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A crystalline spherical protein particle wherein said protein is an antibody or a single-chain Fv fragment of said antibody, wherein said protein has a conformation which is the same as that of the native, soluble counterpart of the protein, as indicated by an ELISA using a monoclonal antibody which specifically binds the native, soluble counterpart.

2. A crystalline spherical protein particle wherein said protein is an antibody or a single-chain Fv fragment of said antibody, wherein said protein has a β-sheet structural content that is less than about 20% different from the β-sheet structural content of the native, soluble counterpart of the protein, and has lost less than about 20% of the α-helical structural content of its native, soluble counterpart, as indicated by FTIR or Circular Dichroism (CD) spectroscopy.

3. The crystalline spherical protein particle according to claim 2, wherein said protein has a β-sheet structural content that is less than about 20% different from the β-sheet structural content of the native, soluble counterpart of the protein, as indicated by a correlation spectra as compared to its native, soluble counterpart, as indicated by FTIR.

4. The crystalline spherical protein particle according to claim 2, wherein said protein loses less than about 20% of its β-helical structural content after storage from about 4 days to about 180 days at from about 4° C. to about 50° C., as compared to its native, soluble counterpart after storage under identical conditions.

5. The crystalline spherical protein particle according to claim 2, wherein said protein has a β-sheet structural content that is less than about 20% different from the β-sheet structural content of the native, soluble counterpart of the protein, and has lost less than about 20% of the α-helical structural content of the native, soluble counterpart of the protein, as indicated by Circular Dichroism (CD) spectroscopy.

6. A crystalline spherical protein particle wherein said protein is an antibody or a single-chain Fv fragment of said antibody, wherein said protein has about 100% of the biological activity of the native, soluble counterpart of the protein.

7. The crystalline spherical protein particle according to claim 6, wherein said protein has about 100% of the biological activity of the native, soluble counterpart of the protein.

8. The crystalline spherical protein particle according to claim 6, wherein said protein has about 90% of the biological activity of the native, soluble counterpart of the protein.

9. The crystalline spherical protein particle according to claim 6, wherein said protein has about 80% of the biological activity of the native, soluble counterpart of the protein.

10. The crystalline spherical protein particle according to claim 6, wherein said protein has about 70% of the biological activity of the native, soluble counterpart of the protein.

11. The crystalline spherical protein particle according to claim 6, wherein said protein has about 60% of the biological activity of the native, soluble counterpart of the protein.

12. The crystalline spherical protein particle according to claim 6, wherein said protein has about 50% of the biological activity of the native, soluble counterpart of the protein.

13. A crystalline spherical protein particle wherein said protein is an antibody or a single-chain Fv fragment of said antibody, wherein said protein has greater than about 50% to about 100% of the biological activity of the native, soluble counterpart of the protein as determined by a bioimmunoassay.

14. The crystalline spherical protein particle according to claim 13, wherein said bioimmunoassay is a direct cytotoxicity bioimmunoassay.

15. The crystalline spherical protein particle according to claim 13, wherein said bioimmunoassay is a complement dependent cytotoxicity (CDC) bioimmunoassay.

16. The crystalline spherical protein particle according to claim 13, wherein said bioimmunoassay is an antibody-dependent cell-mediated cytotoxicity (ADCC) bioimmunoassay.

17. A crystalline spherical protein particle wherein said protein is an antibody or a single-chain Fv fragment of said antibody, wherein said antibody is a therapeutic antibody.

18. The crystalline spherical protein particle according to claim 17, wherein said antibody has a greater half life in vivo than the soluble counterpart of said antibody.

19. The crystalline spherical protein particle according to claim 17, wherein said antibody is a polyclonal antibody or a monoclonal antibody.

20. The crystalline spherical protein particle according to claim 17, wherein said antibody is selected from the group consisting of: Rituximab, Infliximab, Trastuzumab and Etanercept.

21. The crystalline spherical protein particle according to claim 17, wherein said antibody is selected from the group consisting of: Abciximab, Palivizumab, Murumonab-CD3, Gemtuzumab, Basiliximab, Daclizumab, and Zevalin.

22. The crystalline spherical protein particle according to claim 17, wherein said antibody is selected from the group consisting of: an antibody for treating cardiovascular disease, an antibody for treating respiratory disease, an antibody for treating tissue transplant rejection, an antibody for treating organ transplant rejection, an antibody for treating cancer, an antibody for treating inflammatory disease and an antibody used in radioimmunotherapy.

23. The crystalline spherical protein particle according to claim 17, wherein said crystalline spherical protein particle is a dried crystalline spherical protein particle.

24. The crystalline spherical protein particle according to claim 17, wherein said crystalline spherical protein particle is a carrier-free pharmaceutical controlled release crystalline spherical protein particle.

25. The crystalline spherical protein particle according to claim 17, wherein said antibody is selected from the group consisting of: a chimeric antibody, a humanized antibody, a non-glycosylated antibody, a bispecific antibody, a human antibody and a mouse antibody.

* * * * *